US012685545B2

(12) United States Patent
Wright

(10) Patent No.: US 12,685,545 B2
(45) Date of Patent: Jul. 21, 2026

(54) JOINT REVISION SURGERY OSTEOTOME BLADES AND SURGICAL CHISEL BLADES

(71) Applicant: MAP Medical Solutions, LLC, Twin Falls, ID (US)

(72) Inventor: Mark B. Wright, Jackson, ID (US)

(73) Assignee: MAP Medical Solutions, LLC, Twin Falls, ID (US)

( * ) Notice: Subject to any disclaimer, the term of this patent is extended or adjusted under 35 U.S.C. 154(b) by 223 days.

(21) Appl. No.: 18/083,215

(22) Filed: Dec. 16, 2022

(65) Prior Publication Data

US 2024/0180565 A1 Jun. 6, 2024

Related U.S. Application Data

(63) Continuation of application No. 18/075,574, filed on Dec. 6, 2022, now Pat. No. 12,478,389.

(51) Int. Cl.
*A61B 17/16* (2006.01)
*A61B 17/17* (2006.01)
(Continued)

(52) U.S. Cl.
CPC ........ *A61B 17/175* (2013.01); *A61B 17/1735* (2013.01); *A61F 2/4607* (2013.01);
(Continued)

(58) Field of Classification Search
CPC .............. A61B 17/1637; A61B 17/164; A61B 17/1659; A61B 17/1668; A61B 17/1675;
(Continued)

(56) References Cited

U.S. PATENT DOCUMENTS 1,379,973 A * 5/1921 Gillespie ................... B26B 9/02
                                                         30/353
2,215,125 A * 9/1940 Maltz ................. A61B 17/3213
                                                        D24/147
(Continued)

FOREIGN PATENT DOCUMENTS

EP          0695607 B1 *  3/1999  ........... B23D 61/006
WO     WO-9415538 A1 *  7/1994  ............. B23D 59/04

OTHER PUBLICATIONS

Innomed Orthopedic Instruments, Knee and Hip Revision/ Extraction Instruments, Oct. 2022. [Retrieved on May 4, 2023], Retrieved from the Internet: , URL: https://www.innomed.net/ literature/innomed_EN_RevisionExtraction_Oct2022.pdf>, entire document.

*Primary Examiner* — Anu Ramana
(74) *Attorney, Agent, or Firm* — Richard D. Clarke

(57) ABSTRACT

The present application is directed to a Joint Revision Surgery Osteotome Blades and Surgical Chisel Blades which includes a surgical osteotome blade guide block which has a plurality of rearward blade guide slots, a central cavity and a plurality of forward guide slots having a two-way adjustable L-shaped guide plate. The surgical osteotome blade guide block central cavity houses a stem trunnion securing and is secured to the prothesis to be extracted. The guide blade block is secured to the trunnion of the prosthesis to be extracted using a stem trunnion securing member housed within the guide block. Straight, curved, flexible and rigid and compound curved osteotome blades are guided by the blade guide slots to cut the implant free from the bone. The Joint Revision Surgery Osteotome Blades and Surgical Chisel Blades facilitates rapid, efficient and complete removal of an existing prosthesis during joint revision surgery, and significantly increases positive medical outcomes for joint revision procedures.

6 Claims, 46 Drawing Sheets

(51) Int. Cl.
_A61F 2/46_ (2006.01)
_A61B 17/00_ (2006.01)
(52) U.S. Cl.
CPC .............. _A61B 2017/00526_ (2013.01); _A61F 2002/4681_ (2013.01); _A61F 2002/4687_ (2013.01)
(58) Field of Classification Search
CPC ... A61B 17/154; A61B 17/155; A61B 17/157; A61B 17/158; A61B 5/150442; A61B 5/150458; A61B 17/14; A61B 17/142; A61B 17/144; A61B 2017/320074; A61B 2017/320075; A61B 2017/320077; A61B 2017/32116; A61B 2090/0817; A61B 17/320708; B27B 19/006; B27B 19/008
See application file for complete search history.

(56) References Cited

U.S. PATENT DOCUMENTS

| | | | | |
|---|---|---|---|---|
| 2,707,325 A * | 5/1955 | Cripps | ................... | A47G 21/06 |
| | | | | D7/395 |
| 3,448,741 A * | 6/1969 | Dennis | ........... | A61B 17/320016 |
| | | | | 606/159 |
| 3,798,688 A * | 3/1974 | Wasson | .............. | A61B 17/3213 |
| | | | | 30/353 |
| 4,069,824 A * | 1/1978 | Weinstock | ......... | A61B 17/1637 |
| | | | | 408/54 |
| 4,513,742 A * | 4/1985 | Arnegger | ............. | B23D 61/123 |
| | | | | 606/178 |
| 4,584,999 A * | 4/1986 | Arnegger | ............. | B23D 61/006 |
| | | | | 606/178 |
| 4,615,119 A * | 10/1986 | Johnson | ............... | B23D 61/021 |
| | | | | 30/263 |
| 5,306,285 A * | 4/1994 | Miller | .................. | B23D 61/123 |
| | | | | 606/177 |
| 5,468,247 A * | 11/1995 | Matthai | ................. | B27B 19/006 |
| | | | | 606/178 |

| | | | | |
|---|---|---|---|---|
| 6,267,594 B1 * | 7/2001 | Hugo | ................. | A61B 17/1637 |
| | | | | 433/119 |
| D450,844 S | 11/2001 | Lewis | | |
| 7,037,289 B2 * | 5/2006 | Dodge | ............. | B05C 17/00586 |
| | | | | 604/88 |
| 7,497,860 B2 * | 3/2009 | Carusillo | ............. | A61B 17/142 |
| | | | | 606/86 R |
| 7,744,616 B2 * | 6/2010 | O'Donoghue | ....... | A61B 17/142 |
| | | | | 606/177 |
| 7,998,158 B2 * | 8/2011 | Fletcher | .............. | B23D 61/006 |
| | | | | 178/79 |
| 8,454,610 B2 | 6/2013 | Skaggs | | |
| 8,696,673 B2 * | 4/2014 | Walen | .................. | A61B 17/142 |
| | | | | 606/82 |
| 8,734,450 B2 * | 5/2014 | Landon | ................. | A61B 17/142 |
| | | | | 30/337 |
| 8,888,783 B2 * | 11/2014 | Young | ................. | A61B 17/1637 |
| | | | | 606/177 |
| 9,072,526 B2 * | 7/2015 | Carusillo | ............... | A61B 17/14 |
| D793,556 S | 8/2017 | Sweitzer | | |
| 9,763,676 B2 * | 9/2017 | Motherway | .......... | A61B 17/142 |
| 9,867,628 B2 | 1/2018 | Macke | | |
| 10,085,761 B2 | 10/2018 | Cao et al. | | |
| 10,159,496 B2 * | 12/2018 | Anderson | .............. | A61B 50/33 |
| 10,687,824 B2 * | 6/2020 | Shiels | .................. | A61B 17/142 |
| 10,751,070 B2 | 8/2020 | Pendleton et al. | | |
| 11,154,380 B2 * | 10/2021 | Fatiny | ...................... | A61C 3/02 |
| 11,246,713 B2 * | 2/2022 | Pimenta | .............. | A61F 2/30771 |
| 11,844,727 B2 * | 12/2023 | Kahook | .................. | A61F 9/007 |
| 11,919,100 B2 * | 3/2024 | Novak | ................. | B23D 61/006 |
| 2003/0158603 A1 * | 8/2003 | Ebner | ........... | A61B 17/320016 |
| | | | | 623/16.11 |
| 2007/0083209 A1 * | 4/2007 | Schenberger | ........ | A61B 17/142 |
| | | | | 606/82 |
| 2015/0272593 A1 * | 10/2015 | Anderson | .............. | A61B 50/30 |
| | | | | 623/17.11 |
| 2021/0212838 A1 | 7/2021 | Wright | | |
| 2021/0276111 A1 * | 9/2021 | Novak | ................. | A61B 17/144 |
| 2025/0032102 A1 * | 1/2025 | Hacker | ............. | A61B 17/3211 |

\* cited by examiner

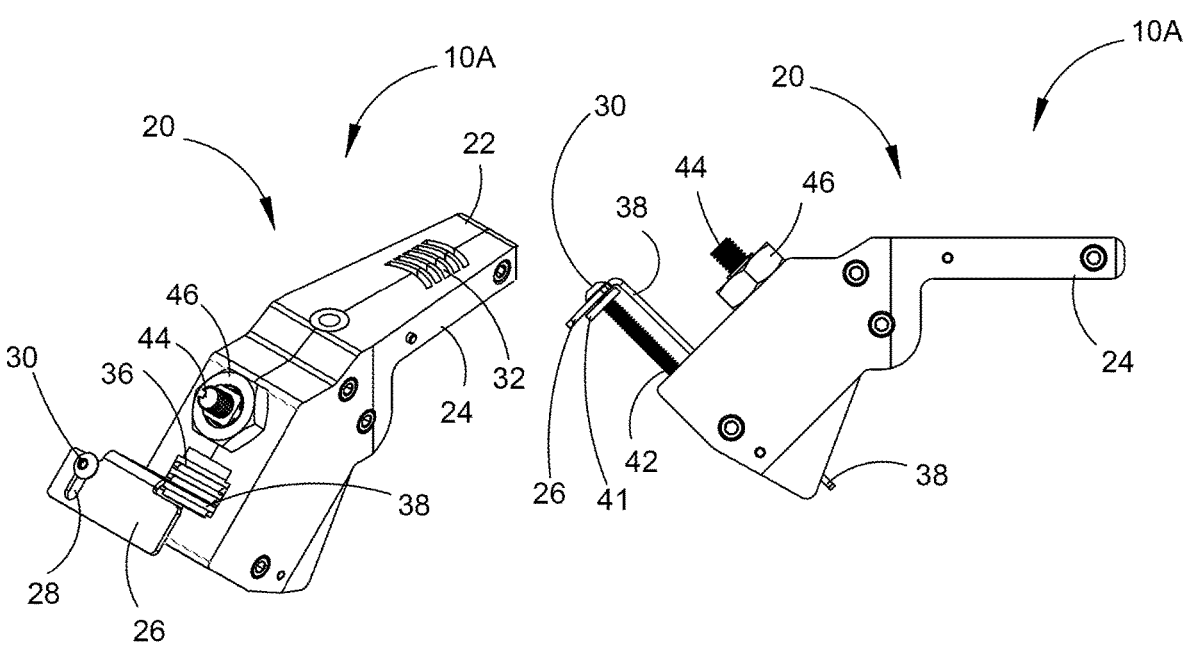
FIG. 11
FIG. 12
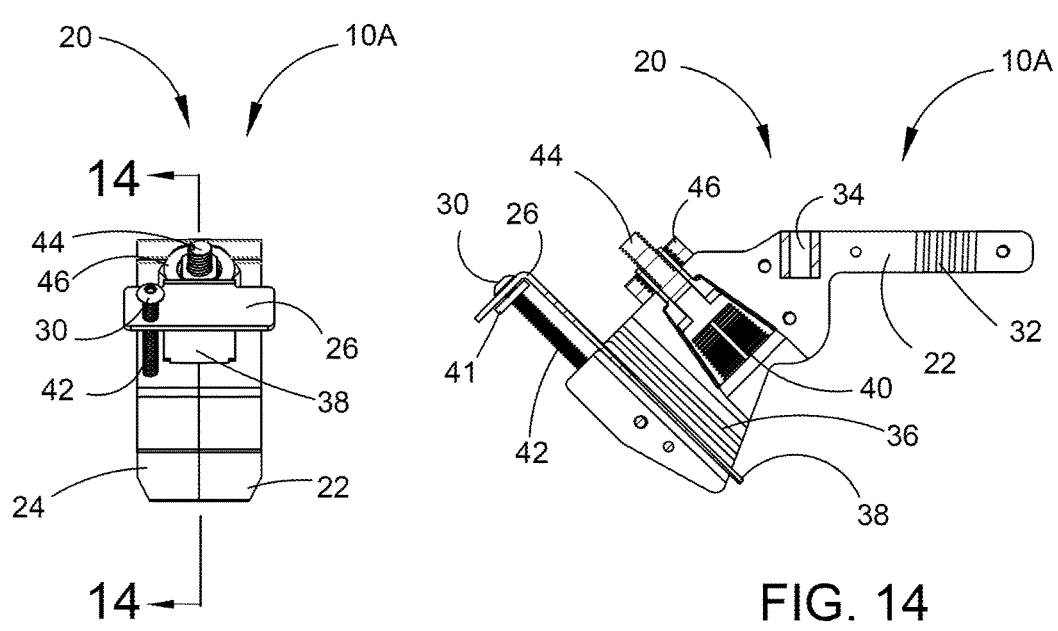
FIG. 13
FIG. 14

JOINT REVISION SURGERY OSTEOTOME BLADES AND SURGICAL CHISEL BLADES

CROSS-REFERENCE TO RELATED APPLICATIONS

The present non-provisional patent application is divisional of U.S. patent application Ser. No. 18/075,574 which application is a continuation-in-part of Applicant's patent application Ser. No. 17/899,521 filed on Aug. 30, 2022, which application is a continuation-in-part of Applicant's patent application Ser. No. 17/542,636 filed on Dec. 6, 2021, which application is a continuation-in-part of Applicant's patent application Ser. No. 17/218,000 filed on Mar. 30, 2021, which has matured into U.S. Pat. No. 11,992,422 issued on May 28, 2024, which application was a continuation-in-part of Ser. No. 16/398,564 filed on Apr. 30, 2019, and which application has matured into U.S. Pat. No. 11,116,525 issued on Sep. 14, 2021, which US Patent claims the benefit of U.S. provisional patent application Ser. No. 62/665,894 filed on May 2, 2018.

FIELD OF THE INVENTION

This application relates to a surgical apparatus used on joint replacement revision surgery in the areas of the hip joint, shoulder joint and knee joint. More particularly, the present application is directed to a Joint Revision Surgery Osteotome Blades and Surgical Chisel Blades for removal of an existing implant and includes a osteotome blade/surgical chisel guide block, a surgical slide hammer, a locking osteotome blade/surgical chisel handle and a plurality of uniquely shaped flexible medial calcar osteotome blades/surgical chisels, rigid anterior and posterior osteotome blades/surgical chisels and curved lateral shoulder release osteotome blades/surgical chisels. The osteotome blade/surgical chisel guide block has a plurality of rearward blade guide slots, a central cavity and a plurality of guide slots having a two-way adjustable L-shaped guide plate. The blade guide block central cavity is positioned over the trunnion end of the existing prosthesis to be removed and secured to the prothesis. Straight, curved and compound curved osteotome blades are guided by the blade guide slots to cut the prothesis free. The guide block is secured to the implant and can be adjusted to guide the direction and angle of the blades inserted therein, then the flexible and rigid blades cut the implant away from the bone to allow the implant to be removed by the action of a slide hammer. The adjustable guide blocks as well as the varying sizes and configurations of straight, curved and compound curved osteotome blades/surgical chisels and related accessories may be sold as a complete surgeon's hospital kit. The Joint Revision Surgery Osteotome Blades and Surgical Chisel Blades facilitates rapid, efficient and complete removal of an existing prosthesis during joint revision surgery.

BACKGROUND OF THE INVENTION

There is growing need to provide a new and refined method of performing delicate surgical operations including hip, shoulder and knee revisions. The similarity in these operations is that the implants have to be inserted into a major bone in the area and when there is a problem with them the prostheses has to be removed.

As with any other mechanical device, a total hip replacement can be subject to various forms of mechanical or biological failure. Such a failure may require a revision of the hip replacement to address the cause of failure and its consequences. A revision of a total hip replacement sometimes requires removal of the femoral implant.

The revision hip implant is comprised of four parts that work together to restore the original function of the ball-and-socket joint, namely, (1) A metal hip stem that is inserted into the top of the thighbone: (2) A metal cup which holds the cup liner; (3) A cup liner which holds the femoral head; and (4) The femoral head or ball which is attached to the top of the hip stem and is inserted into the cup liner to form the ball-and-socket joint.

The wearing down of the plastic component has an unfortunate side effect. The tiny plastic particles that wear off are attacked by your body's immune system, and this immune response also attacks the healthy bone around your implant. This leads to a condition called osteolysis, in which the bone in the area around the joint implant softens as it is absorbed by the body, thus making the implant unstable and in need of revision.

If the bone next to the primary implant is fractured in an accident, revision surgery may be required in order to provide a safe, stable joint. In this case, the original implant may need to be removed, the fracture addressed and a revision joint implanted.

In a low percentage of cases, the hip may become infected after surgery. Although it may be successfully treated with antibiotics, there are severe cases where a follow-up revision surgery may be required.

Hip revision operations are performed relatively infrequently. In the United States, there are approximately 18 revision hip replacements performed for every 100 hip replacements. The most common reasons for revision are: (1) Repetitive (recurrent) dislocation of a hip replacement; (2) Mechanical failure (implant wear and tear—loosening or breakage); and (3) Infection.

Numerous innovations for various joint revision surgery apparatuses have been provided in the prior art. Even though these innovations may be suitable for the specific individual purposes to which they address, they differ from the present Joint Revision Surgery Osteotome Blades and Surgical Chisel Blades as hereinafter contrasted. The following is a summary of those prior art patents most relevant to the Joint Revision Surgery Osteotome Blades and Surgical Chisel Blades at hand, as well as a description outlining the difference between the features of the present application and those of the prior art.

U.S. Pat. No. 10,959,738 issued to Sweitzer provides an osteotome that is designed for implanting and extracting medical device implants. The osteotome includes a handle, a blade attachment assembly about a first end of the handle for receiving a blade, and a wing assembly about a second end of the handle opposite the first end. The wing assembly further includes a wing extending outwardly from the handle.

U.S. Pat. No. 11,191,651 issued to Rivera, Jr. discloses and teaches an implant removal tool used to remove a femoral implant from a femur bone by providing a substantially U-shaped body having a substantially rectangular-shaped opening located thereon that allows the substantially U-shaped body to be placed over a neck of a femoral implant so a sharpened front edge of the substantially U-shaped body makes direct contact with an inner surface of the stein of the femoral implant. The U-shaped body may have front side edges that extend beyond a front edge to allow the front side edges to cut anterior and posterior surface of the implant.

US Published patent application No. 2022/0125591 A1 of Rivera, Jr. discloses and claims a tool and an associated method for removing a prosthetic implant. Although the tool can be used to remove a variety of different prosthetic implants, it finds particular application in the removal of femoral implants. In one embodiment, both lateral and medial tools are utilized. The lateral tool includes a generally arcuate shape with upstanding sidewalls that define an arcuate interior. The lateral tool is thus dimensioned to follow the contour of the lateral side of a femoral implant. The medial tool includes opposing side walls that define an interior opening. The opening is sized to receive the neck of the femoral implant, thereby allowing the tool to closely follow the medial bone/implant interface.

US Published patent application No. 2022/0240948 A1 of Amino teaches and describes a thin-blade chisel system, for separating an outer surface of an orthopedic implant and an inner surface of a bone from each other, includes a thin-blade chisel having a blade tip at a distal end portion in a longitudinal direction, and a hammering direction changing tool engaged with the thin-blade chisel to apply a force in an advancing direction of the blade tip. The thin-blade chisel includes a hammering blow-receiving part, preferably a through bole penetrating in a thickness direction, at a predetermined position on a proximal side closer to the surgeon. The hammering direction changing tool includes a hammering portion to be hammered, located at a proximal end portion, and a recess formed at a distal end portion, to be engaged with an inner circumferential surface of the through hole.

None of the foregoing prior art teaches or suggests the particular unique features and components of the Joint Revision Surgery Osteotome Blades and Surgical Chisel Blades and thus clarifies the need for further improvements in the types of surgical device systems which can be used for these purposes, namely, making extraction of existing prostheses and implants easier and revision surgery more efficient and more effective, leading to improved patient outcomes.

In this respect, before explaining at least one embodiment of the Joint Revision Surgery Osteotome Blades and Surgical Chisel Blades in detail, it is to be understood that the design is not limited in its application to the details of construction and to the arrangement of the components set forth in the following description or illustrated in the drawings. The Joint Revision Surgery Osteotome Blades and Surgical Chisel Blades disclosed herein is capable of other embodiments and of being practiced and carried out in various ways. Also, it is to be understood that the phraseology and terminology employed herein are for the purpose of description and should not be regarded as limiting.

SUMMARY OF THE INVENTION

The principle advantage of the of the Joint Revision Surgery Osteotome Blades and Surgical Chisel Blades is to enable the performance of a significantly quicker, safer and more successful joint revision surgery procedure, resulting in significantly less blood loss during the joint revision surgery procedure and much shorter operating room use times during the joint revision surgery procedure.

Another advantage of using the Joint Revision Surgery Osteotome Blades and Surgical Chisel Blades is to perform joint revision surgery with less instrumentation and tools, for example, cables and long stems during the procedure.

Another advantage of using the Joint Revision Surgery Osteotome Blades and Surgical Chisel Blades is to have quicker times to have full weight bearing capability after joint revision surgery, fewer complications during and after joint revision surgery, resulting in less morbidity and mortality following joint revision surgery.

Another advantage of using the Joint Revision Surgery Osteotome Blades and Surgical Chisel Blades is that it will accommodate the removal of collared femoral stems which are significantly more difficult to extract than non-collared femoral stems.

An advantage of the Joint Revision Surgery Osteotome Blades and Surgical Chisel Blades is to provide a surgical system having four primary components, including (1) an osteotome/surgical chisel blade guide block assembly; (2) a surgical slide hammer; (3) an osteotome blade/surgical chisel locking handle assembly; and (4) a variety of both flexible and rigid osteotome/surgical chisel cutting blades.

An advantage of the Joint Revision Surgery Osteotome Blades and Surgical Chisel Blades is that it provides a surgical slide hammer attachable to the guide block for rapid extraction of an implant during the joint revision surgery procedure.

Another advantage of using the Joint Revision Surgery Osteotome Blades and Surgical Chisel Blades is that it provides an osteotome blade/surgical chisel locking handle assembly which allows for the rapid insertion and removal of various osteotome blades/surgical chisels as required by the surgeon during joint revision surgery procedures.

Another advantage of the Joint Revision Surgery Apparatus is to provide flexible uniquely shaped medial calcar osteotome blades and surgical chisel blades, curved lateral shoulder release osteotome blades and surgical chisel blades, general purpose osteotome blades and surgical chisel blades and anterior and posterior osteotome blades and surgical chisel blades.

Another advantage of the Joint Revision Surgery Apparatus is to provide flexible uniquely shaped medial calcar osteotome blades having spoon-shaped and spork shaped sharpened cutting edges, as both osteotome blades which are beveled on both sides of the cutting edge, and surgical chisel blades which are beveled on one side of the cutting edge.

Another advantage of the Joint Revision Surgery Apparatus is to provide flexible and rigid osteotome blades and surgical chisel blades in the form of curved lateral shoulder release osteotome blades and surgical chisel blades.

Another advantage of the Joint Revision Surgery Apparatus is to provide rigid uniquely shaped anterior and posterior osteotome blades and surgical chisel blades.

Another advantage of the Joint Revision Surgery Apparatus is to provide flexible uniquely shaped medial calcar osteotome blades having spoon-shaped and spork shaped sharpened cutting edges, as both osteotome blades which are beveled on both sides of the cutting edge and surgical chisel blades which are beveled on one side of the cutting edge, having elongated blade shafts and narrower cutting edges.

In summary, the four primary components, namely: (1) the osteotome blade/surgical chisel guide block assembly; (2) the osteotome blade/surgical chisel locking handle assembly; (3) the surgical slide hammer; and (4) the various flexible medial calcar osteotome blades/surgical chisels, the lateral shoulder release blade, the anterior and posterior blades and the general purpose release chisel of the Joint Revision Surgery Osteotome Blades and Surgical Chisel Blades all work synergistically together to make extraction of an implant more efficient, less time consuming and with significantly less blood loss by the patient, all of which result in improved patient outcomes. Moreover, this system can be adjusted for any size and shape of implant to be extracted, including collared and non-collared prostheses. The guide block assembly embodiment of the joint revision surgery system and method wherein an assembled osteotome blade/ surgical chisel guide block having an adjustable L-shaped osteotome blade/surgical chisel guide plate having a lower portion and an upper portion, can be adjusted in two separate ways. First, the adjustment plate retaining screw can be threaded outwardly (lifted) or threaded inwardly (lowered) to retract or extend the lower adjustment plate towards or away from the stem. Second, the adjustment plate retaining screw can be removed altogether and the guide plate lower section shifted to a different guide slot within the plurality of blade guide slots, with that guide slot being closer or farther away from the stem to be extracted. One or both of the aforementioned guide plate adjustments can be made to successfully guide a cutting blade down to a stem of varying size, and in this way the guide block assembly can accommodate varying sized stems to be removed during revision surgery. Moreover, both a collared and non-collared stem can be extracted by making the appropriate adjustments to the length and distance of the adjustable guide plate.

A joint revision surgery system is provided comprising: (a) an osteotome blade and surgical chisel blade guide block assembly having a centrally located cavity and a plurality of forwardly located osteotome blade guide slots, a stem trunnion securing member mountable located within said central cavity and secured to said osteotome blade guide block, an L-shaped adjustable blade guide plate moveably located within said plurality of forwardly located osteotome blade/ surgical chisel guide slots, and a plurality of rearwardly located osteotome blade/surgical chisel guide slots for accepting osteotome blades and surgical chisels; (b) a surgical slide hammer assembly; (c) an osteotome blade/surgical chisel locking handle assembly; and (d) a plurality of osteotome blades and surgical chisel blades, including osteotome blades having flexible and rigid blade shafts; wherein said assembled osteotome blade/surgical chisel guide block is affixed to an implanted femoral stem for extraction by attaching said stem trunnion securing member to the trunnion of said stem, and then said L-shaped adjustable guide plate is adjusted upwardly and downwardly using said retaining screw and said L-shaped adjustable guide plate is adjusted forwardly and backwardly by extending said lower section of said adjustable guide plate into one or more of the plurality of guide slots defined by the guide block assembly, then extending said flexible osteotome blades down through said forwardly located osteotome blade guide slots containing the L-shaped adjustable guide plate and extending said rigid osteotome blades down through said rearward slots to reach the femoral stem and thereby cut the femoral stem free from the femur bone during revision surgery. What's the difference between a surgical chisel and an osteotome blade? An osteotome is an orthopedic instrument that is typically used for cutting bone. A surgical chisel is used for shaping bone. Functionally, the primary difference is that a chisel has one beveled edge, while an osteotome has two beveled edges. Additionally, the flexible medial calcar osteotome blade having a spoon-shaped and spork-shaped cutting edges can be configured to be an osteotome blade having two of the sharpened cutting edges beveled or configured to be a surgical chisel wherein only one side of the sharpened cutting edge is beveled. This is also an aspect of the present invention, wherein all of the blades disclosed and described herein can be configured as either osteotome blades or surgical chisels, can be flexible or rigid, and can be curved and compound curved (curved in two planes). Osteotomes and surgical chisels are collectively known as osteotomes, a group of surgical blades which includes the subgroup of surgical chisels.

With respect to the above description then, it is to be realized that the optimum dimensional relationships for the parts of the Joint Revision Surgery Osteotome Blades and Surgical Chisel Blades, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present design. Therefore, the foregoing is considered as illustrative only of the principles of the Joint Revision Surgery Osteotome Blades and Surgical Chisel Blades. Further, since numerous modifications and changes will readily occur to those skilled in the art, it is not desired to limit the Joint Revision Surgery Osteotome Blades and Surgical Chisel Blades to the exact construction and operation shown and described, and accordingly, all suitable modifications and equivalents may be resorted to, falling within the scope of this application.

While the apparatus and method has or will be described for the sake of grammatical fluidity with functional explanations, it is to be expressly understood that the claims, unless expressly formulated under 35 USC 112, or similar applicable law, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112, or similar applicable law. The Joint Revision Surgery Apparatus can be better visualized by turning now to the following drawings wherein like elements are referenced by like numerals.

BRIEF DESCRIPTION OF THE DRAWINGS

The accompanying drawings, which are incorporated in and form a part of this specification, illustrate embodiments of the Joint Revision Surgery Osteotome Blades and Surgical Chisel Blades and together with the description, serve to explain the principles of this application.

FIG. 11 depicts a top, side elevational and perspective view of an alternate embodiment of the joint revision surgery apparatus illustrating an assembled osteotome blade guide block having an adjustable L-shaped osteotome blade guide plate fully retracted upwardly.

FIG. 12 depicts a side elevational view of an alternate embodiment of the joint revision surgery apparatus illustrating an assembled osteotome blade guide block having an adjustable L-shaped osteotome blade guide plate fully retracted upwardly.

FIG. 13 depicts a front view of an alternate embodiment of the joint revision surgery apparatus illustrating an assembled osteotome blade guide block having an adjustable L-shaped osteotome blade guide plate fully retracted upwardly.

FIG. 14 depicts a cross-sectional view of an alternate embodiment of the joint revision surgery apparatus illustrating an assembled osteotome blade guide block having an adjustable L-shaped osteotome blade guide plate fully retracted upwardly of FIG. 13.

FIG. 59 depicts a top plan view of a surgical blade locking osteotome handle assembly having a surgical osteotome blade inserted therein and showing the locking lever in the outward locked position which secures the surgical osteotome blade therein.

FIG. 60 depicts a bottom view of a surgical blade locking osteotome handle assembly having a surgical osteotome blade inserted therein and showing the locking lever in the outward locked position which secures the surgical osteotome blade therein.

FIG. 61 depicts a front view of a surgical blade locking osteotome handle assembly having a surgical osteotome blade inserted therein and showing the locking lever in the outward locked position which secures the surgical osteotome blade therein.

FIG. 62 depicts a cross-sectional view of the surgical blade locking osteotome handle assembly having a surgical osteotome blade inserted therein and showing the locking lever in the outward locked position which secures the surgical osteotome blade therein, as shown in FIG. 61.

Figures 84, 85, 86:
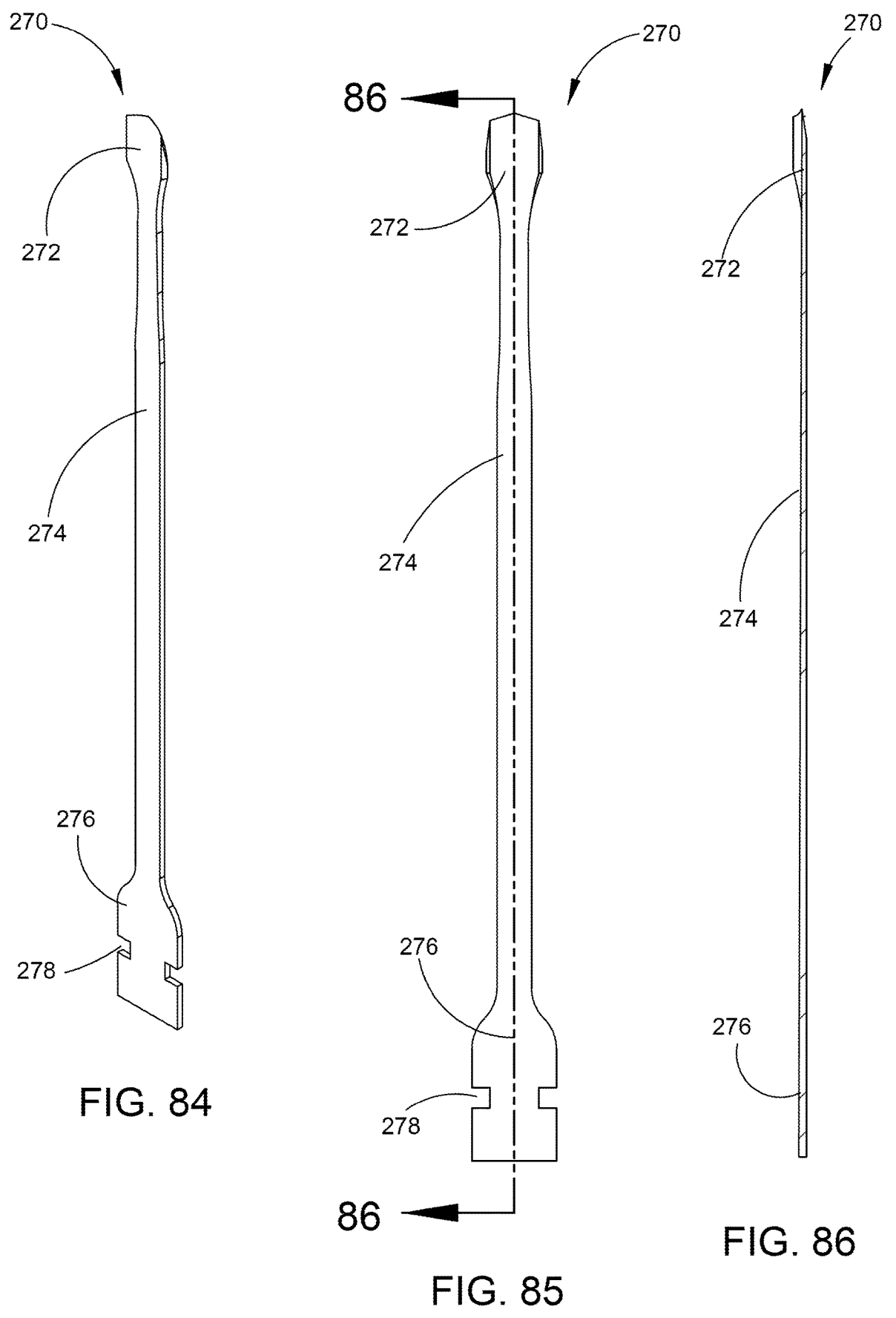

FIG. 84 depicts a top, side elevational and perspective view of a flexible medial calcar osteotome blade having a spoon-shaped cutting edge and an elongated blade shaft.

FIG. 85 depicts a front view of a flexible medial calcar osteotome blade having a spoon-shaped cutting edge and an elongated blade shaft.

FIG. 86 depicts a cross-sectional view of the flexible medial calcar osteotome blade having a spoon-shaped cutting edge and an elongated blade shaft, shown in FIG. 85.

FIG. 96 depicts a top, side elevational and perspective view of a flexible medial calcar osteotome blade having a spork-shaped cutting edge and an elongated blade shaft.

FIG. 97 depicts a front view of a flexible medial calcar osteotome blade having a spork-shaped cutting edge and an elongated blade shaft.

FIG. 98 depicts a cross-sectional view of the flexible medial calcar osteotome blade having a spork-shaped cutting edge and an elongated blade shaft, as shown in FIG. 97.

FIG. 119 depicts a left side elevational view of a curved lateral shoulder release osteotome blade having a protruding stop feature on the blade shaft.

FIG. 120 depicts a top, side elevational and perspective view of a curved lateral shoulder release osteotome blade having a protruding stop feature on the blade shaft.

FIG. 121 depicts a front view of a curved lateral shoulder release osteotome blade having a protruding stop feature on the blade shaft.

FIG. 122 depicts a cross-sectional view of the curved lateral shoulder release osteotome blade having a protruding stop feature on the blade shaft, as shown in FIG. 121.

FIG. 123 depicts a top, side elevational and perspective view of a general purpose release chisel osteotome blade.

FIG. 124 depicts a front view of a general purpose release chisel osteotome blade.

FIG. 125 depicts a cross-sectional view of the general purpose release chisel osteotome blade, as shown in FIG. 124.

FIG. 126 depicts a top plan view of a general purpose release chisel osteotome blade.

FIG. 127 depicts a bottom view of a general purpose release chisel osteotome blade.

FIG. 128 depicts a rear view of a general purpose release chisel osteotome blade.

FIG. 129 depicts a left side elevational view of a general purpose release chisel osteotome blade.

FIG. 130 depicts a front view of a general purpose release chisel osteotome blade.

Figures 126, 127, 128, 129, 130, 131:
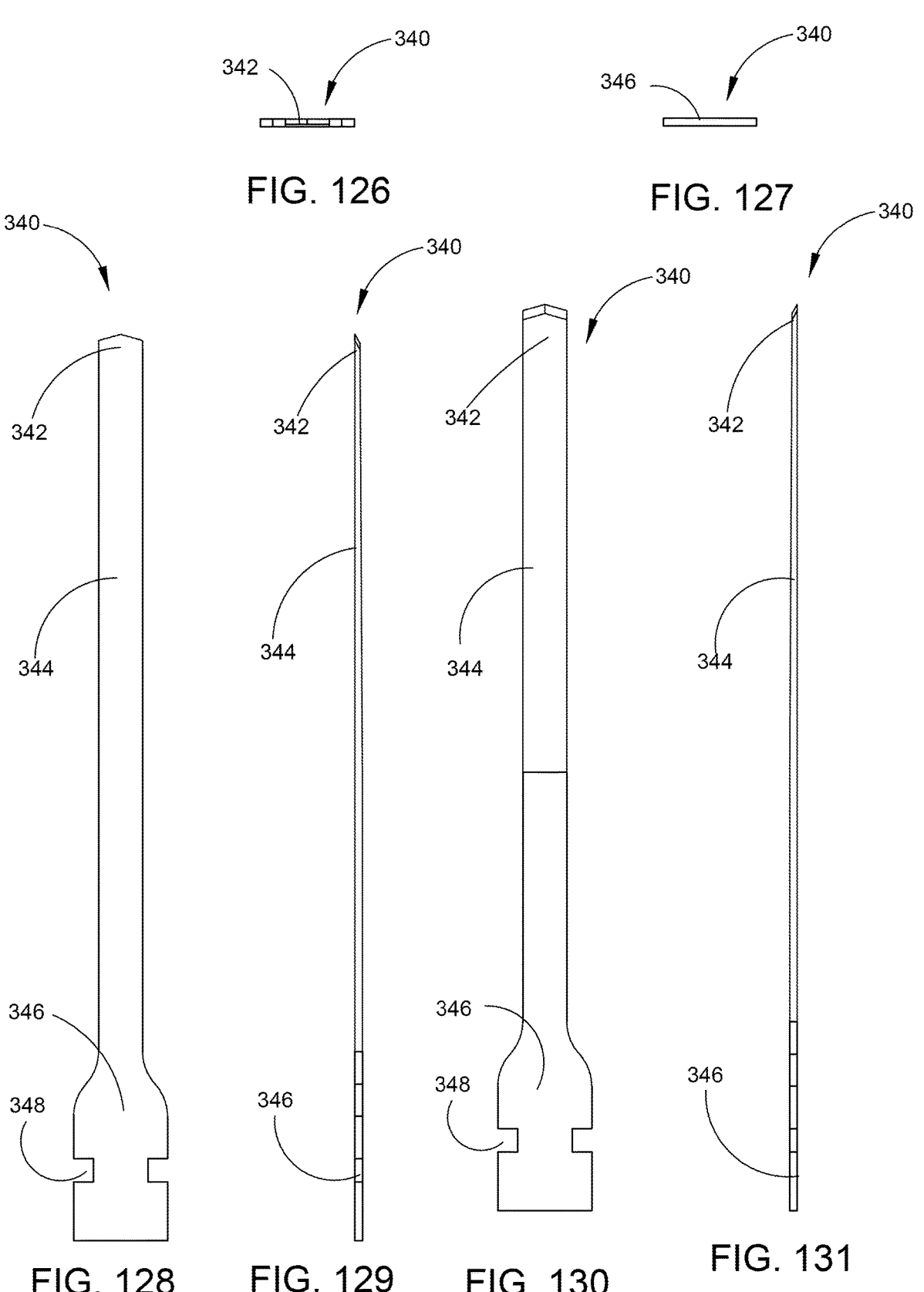

FIG. 131 depicts a right side elevational view of a general purpose release chisel osteotome blade.

Figures 132, 133, 134:
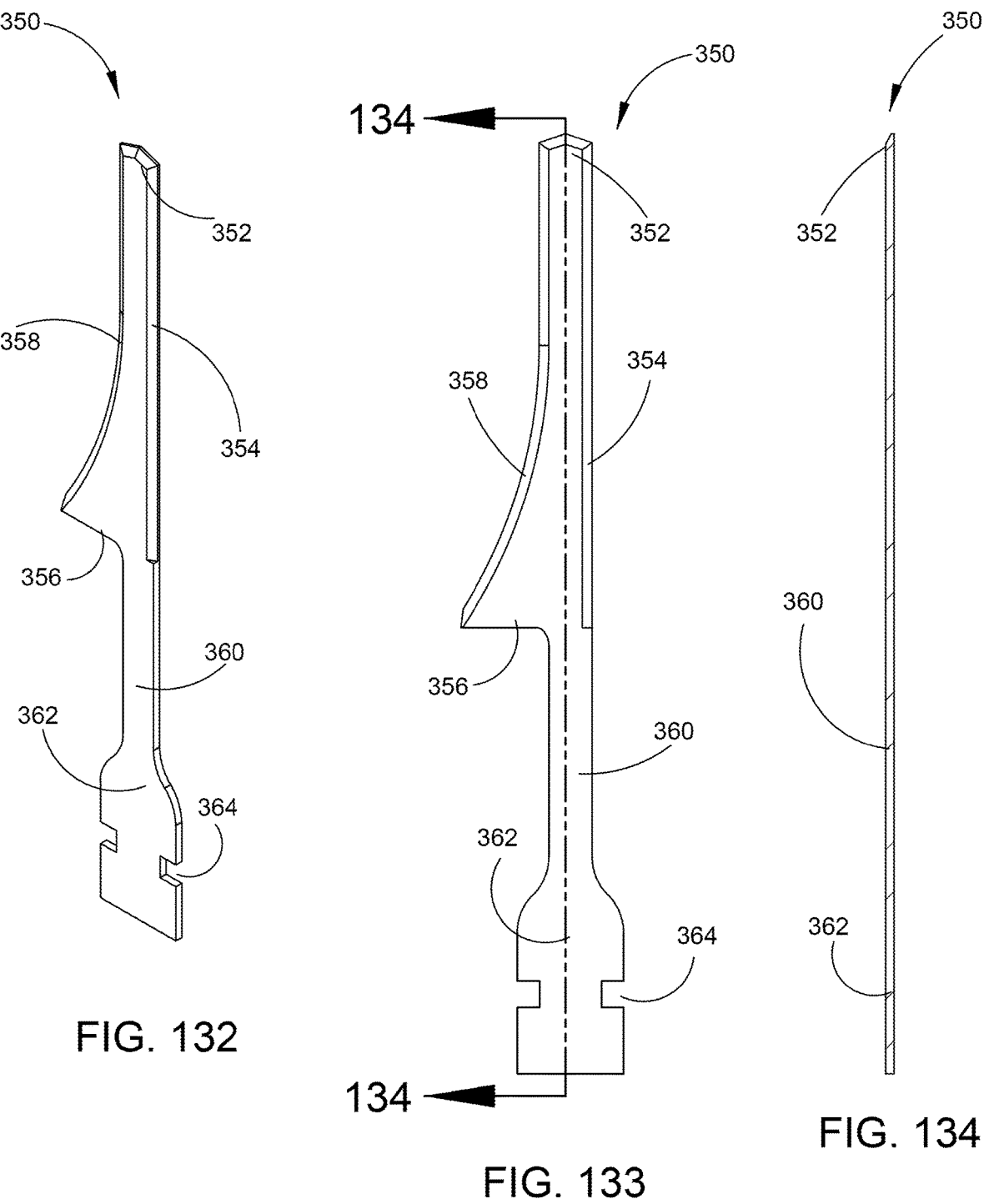

FIG. 132 depicts a top, side elevational and perspective view of an anterior and posterior osteotome blade having a left side curved cutting edge and a right side straight cutting edge.

FIG. 133 depicts a front view of an anterior and posterior osteotome blade having a left side curved cutting edge and a right side straight cutting edge.

FIG. 134 depicts a cross-sectional view of the anterior and posterior osteotome blade having a left side curved cutting edge and a right side straight cutting edge, shown in FIG. 133.

Figures 135, 136, 137, 138, 139, 140:
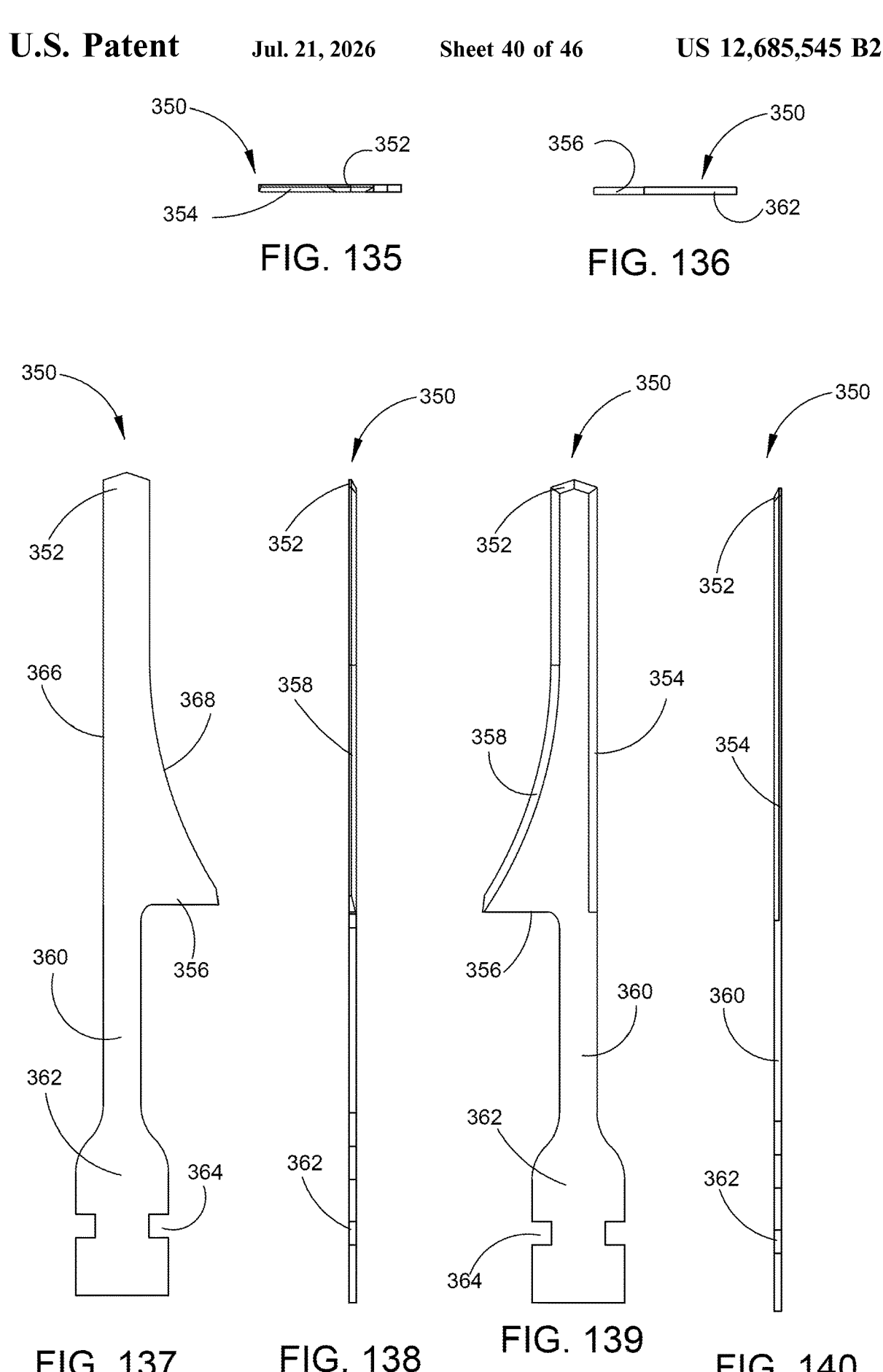

FIG. 135 depicts a top plan view of an anterior and posterior osteotome blade having a left side curved cutting edge and a right side straight cutting edge.

FIG. 136 depicts a bottom view of an anterior and posterior osteotome blade having a left side curved cutting edge and a right side straight cutting edge.

FIG. 137 depicts a rear view of an anterior and posterior osteotome blade having a left side curved cutting edge and a right side straight cutting edge.

FIG. 138 depicts a left side elevational view of an anterior and posterior osteotome blade having a left side curved cutting edge and a right side straight cutting edge.

FIG. 139 depicts a front view of an anterior and posterior osteotome blade having a left side curved cutting edge and a right side straight cutting edge.

FIG. 140 depicts a right side elevational view of an anterior and posterior osteotome blade having a left side curved cutting edge and a right side straight cutting edge.

Figures 141, 142, 143:
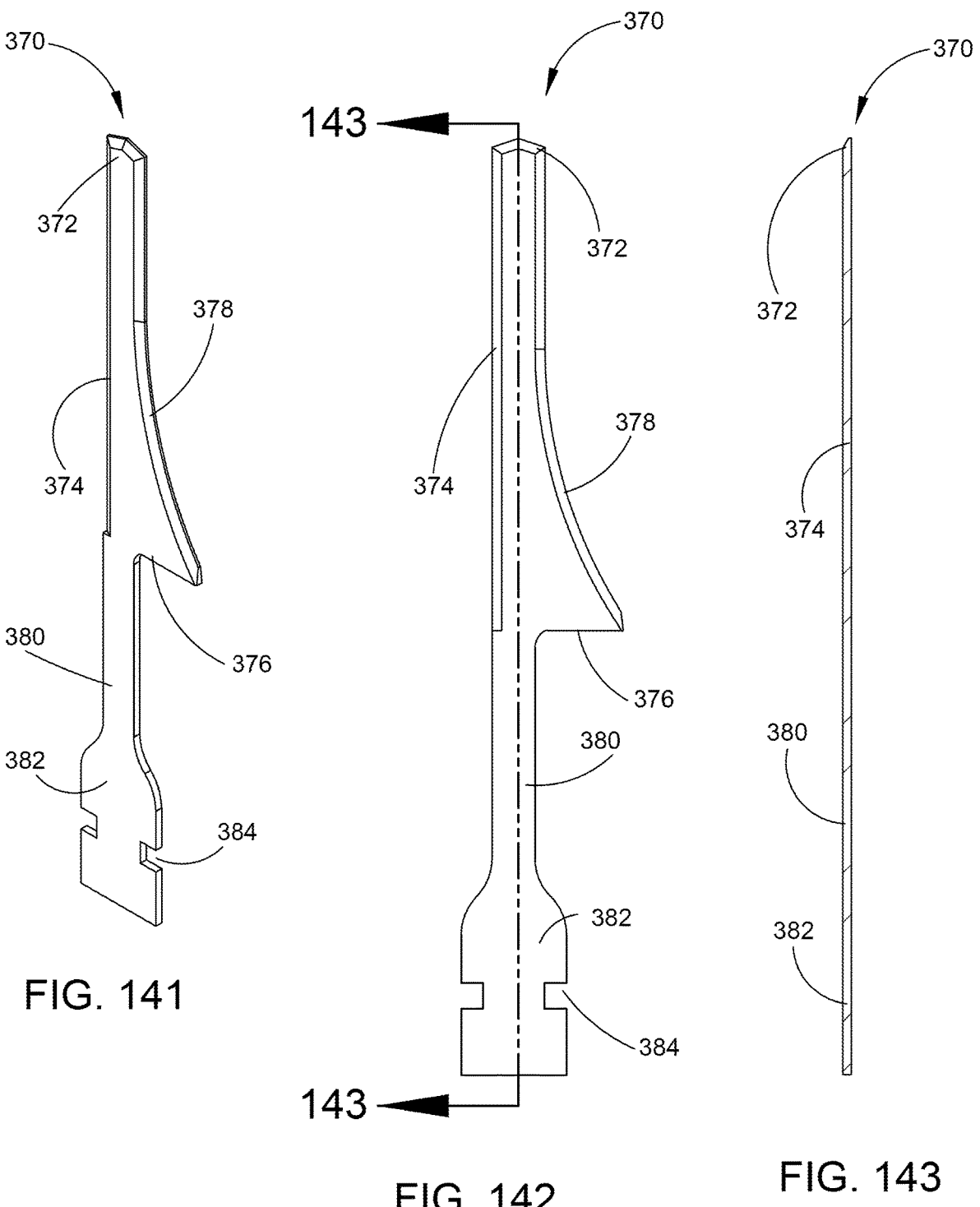

FIG. 141 depicts a top, side elevational and perspective view of an anterior and posterior osteotome blade having a right side curved cutting edge and a left side straight cutting edge, which is configured as the mirror image of the blades shown in FIGS. 132-140.

FIG. 142 depicts a front view of an anterior and posterior osteotome blade having a right side curved cutting edge and a left side straight cutting edge.

FIG. 143 depicts a cross-sectional view of the anterior and posterior osteotome blade having a right side curved cutting edge and a left side straight cutting edge, shown in FIG. 142.

Figures 144, 145, 146, 147, 148, 149:
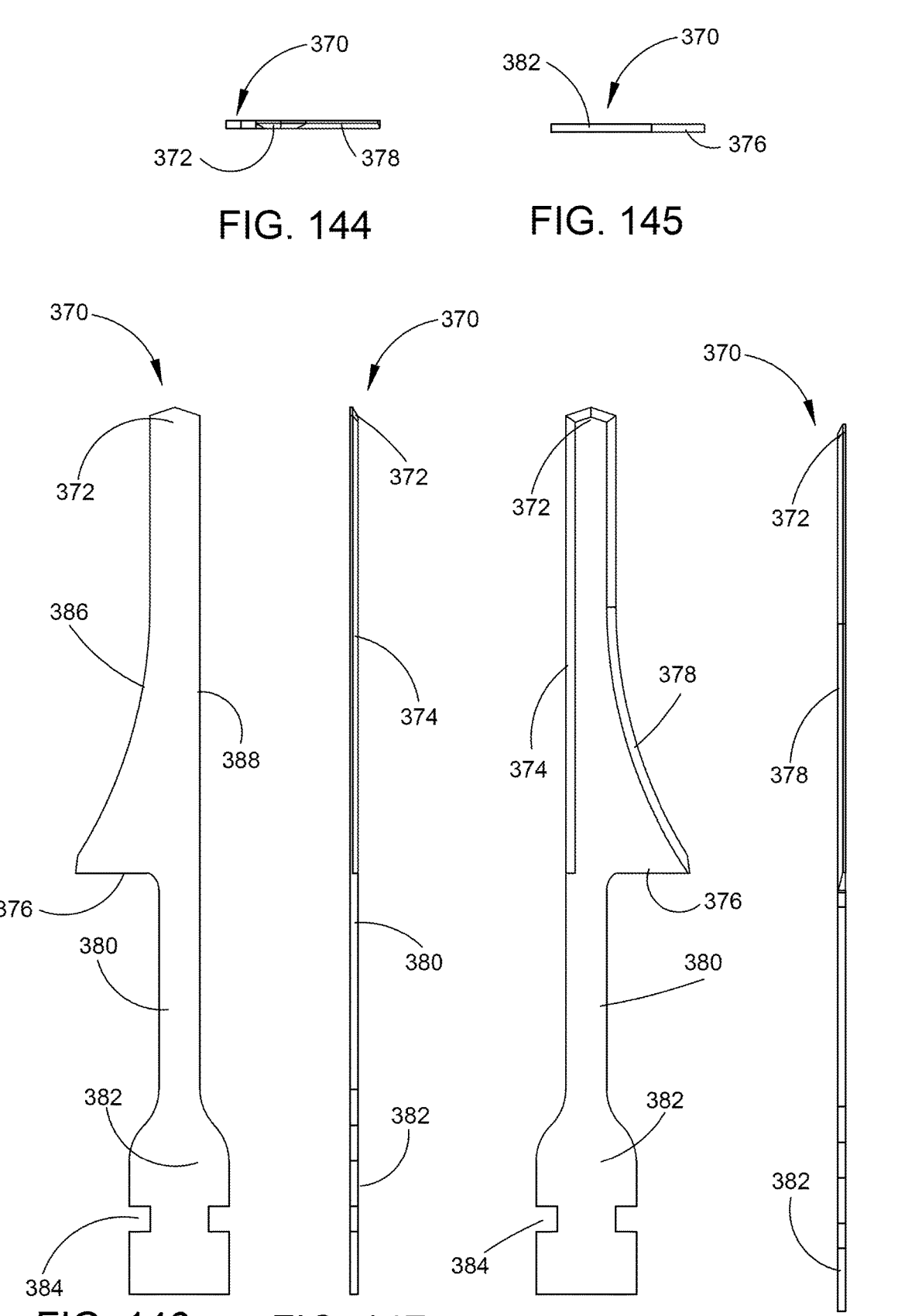

FIG. 144 depicts a top plan view of an anterior and posterior osteotome blade having a right side curved cutting edge and a left side straight cutting edge.

FIG. 145 depicts a bottom view of an anterior and posterior osteotome blade having a right side curved cutting edge and a left side straight cutting edge.

FIG. 146 depicts a rear view of an anterior and posterior osteotome blade having a right side curved cutting edge and a left side straight cutting edge.

FIG. 147 depicts a left side elevational view of an anterior and posterior osteotome blade having a right side curved cutting edge and a left side straight cutting edge.

FIG. 148 depicts a front view of an anterior and posterior osteotome blade having a right side curved cutting edge and a left side straight cutting edge.

FIG. 149 depicts a right side elevational view of an anterior and posterior osteotome blade having a right side curved cutting edge and a left side straight cutting edge.

Figures 150, 151:
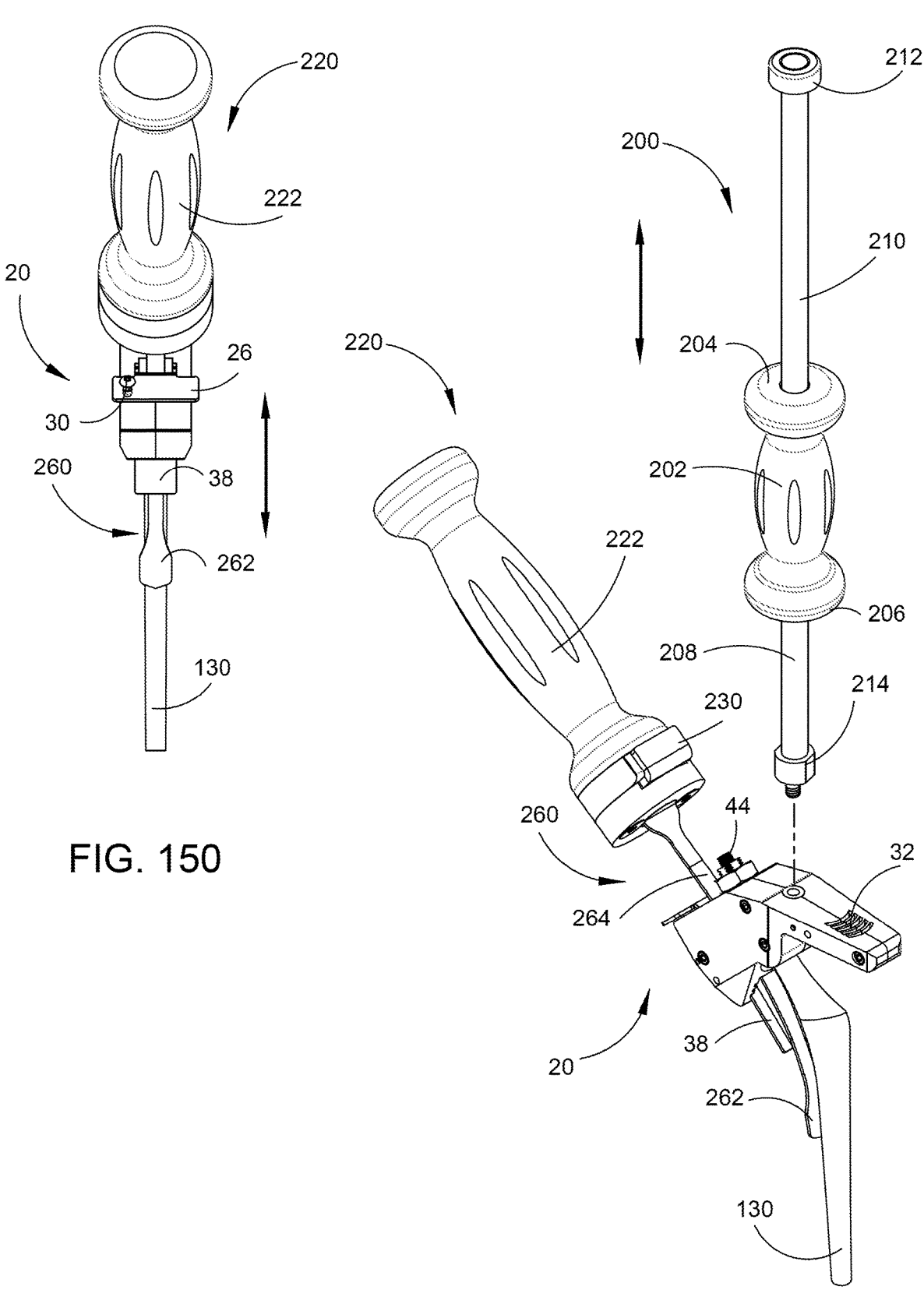

FIG. 150 depicts a front view of an osteotome handle having a flexible medial calcar spoon-shaped blade attached thereto, with the flexible medial calcar spoon-shaped blade extending through, and being guided by the guide block assembly and cutting the medial calcar from an implanted femoral stem.

FIG. 151 depicts a top, side elevational and perspective view of an osteotome handle having a flexible medial calcar spoon-shaped blade attached thereto, with the flexible medial calcar spoon-shaped blade extending through, and being guided by the guide block assembly and cutting the medial calcar from an implanted femoral stem.

Figures 152, 153:
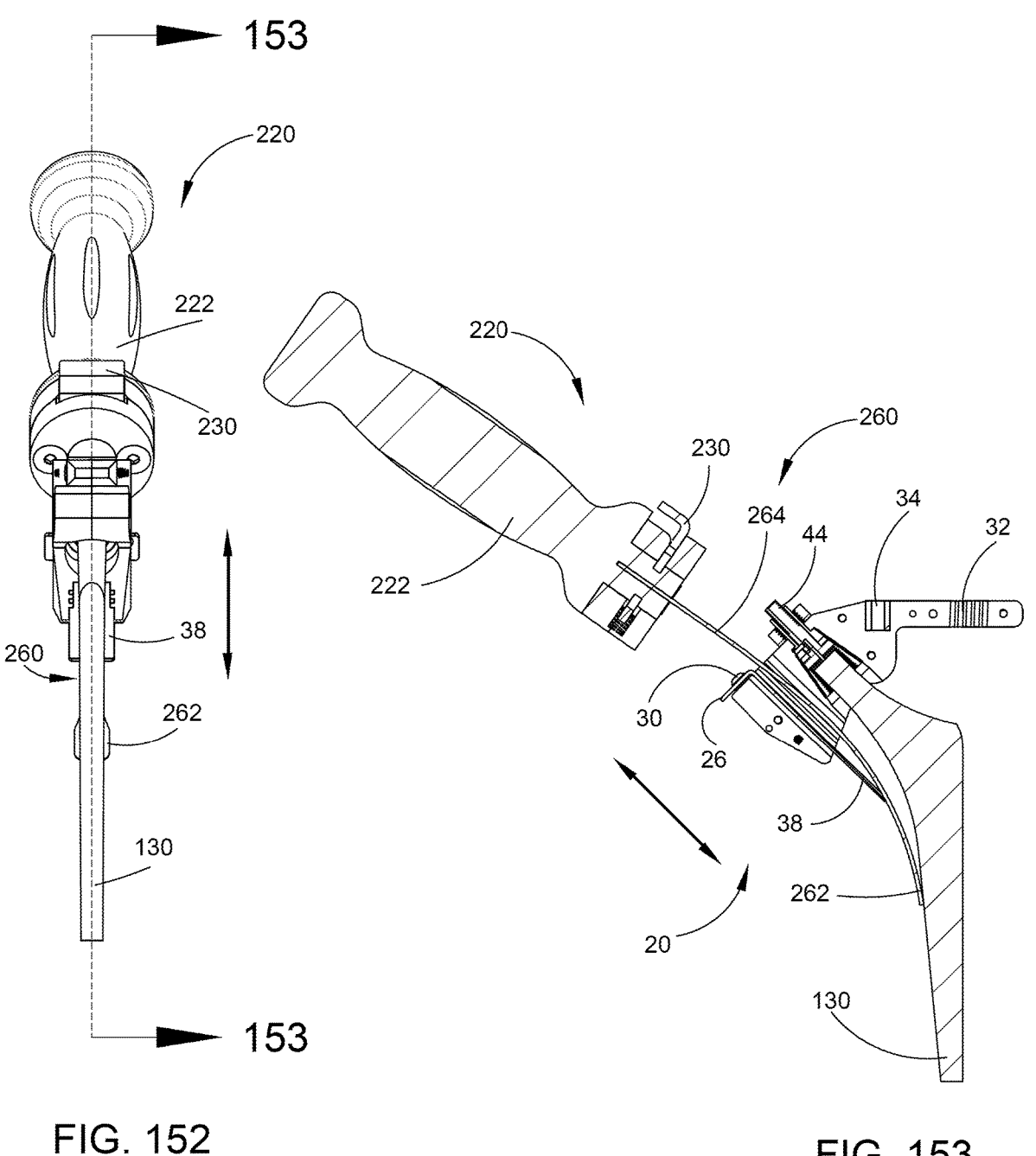

FIG. 152 depicts a rear view of an osteotome handle having a flexible medial calcar spoon-shaped blade attached thereto, with the flexible medial calcar spoon-shaped blade extending through, and being guided by the guide block assembly and cutting the medial calcar from an implanted femoral stem.

FIG. 153 depicts a cross-sectional view of the osteotome handle having a flexible medial calcar spoon-shaped blade attached thereto, with the flexible medial calcar spoon-shaped blade extending through, and being guided by the guide block assembly and cutting the medial calcar from an implanted femoral stem, as shown in FIG. 152.

Figures 154, 155:
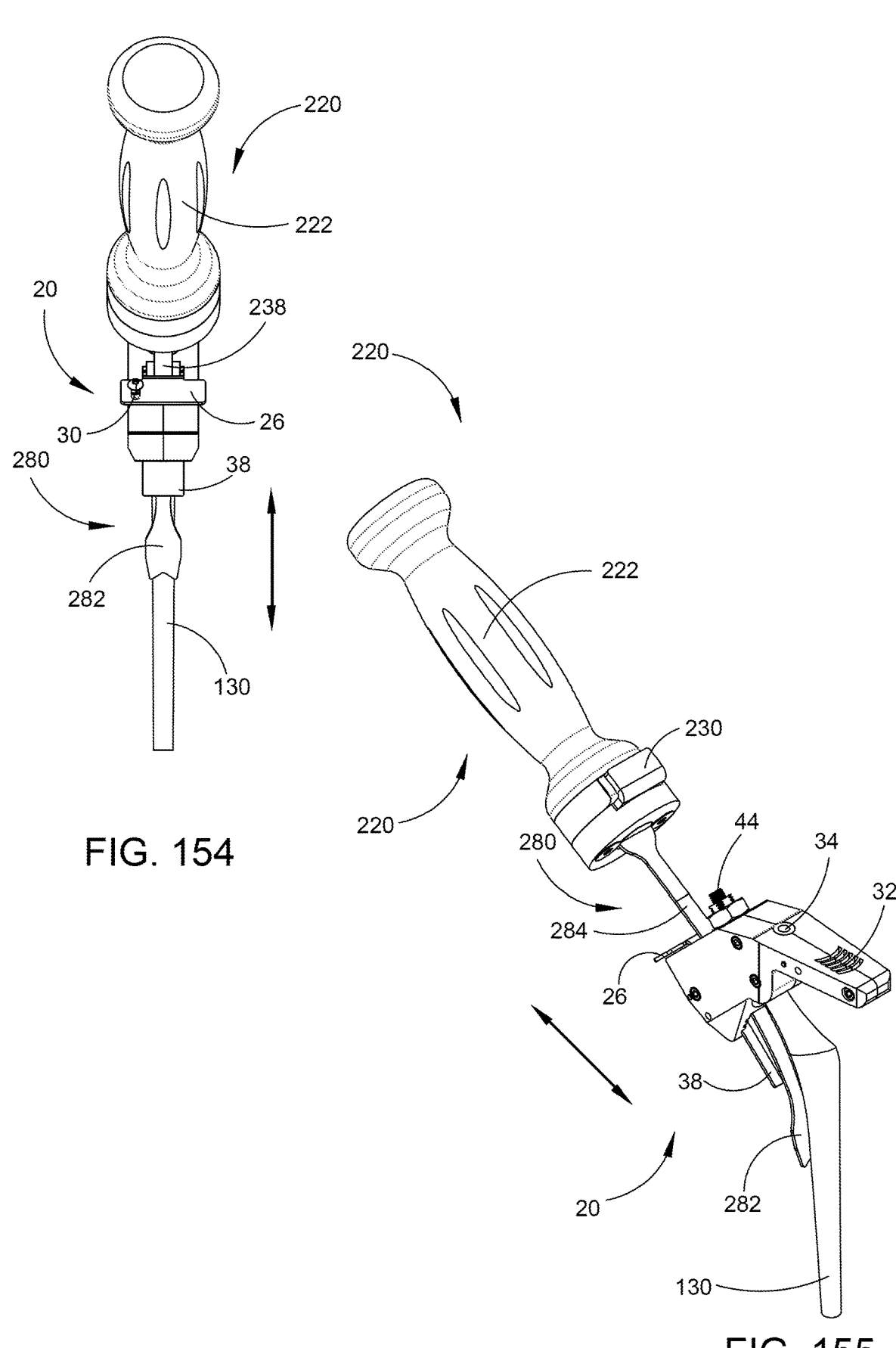

FIG. 154 depicts a front view of an osteotome handle having a flexible medial calcar spork-shaped blade attached thereto, with the flexible medial calcar spork-shaped blade extending through, and being guided by the guide block assembly and cutting the medial calcar from an implanted femoral stem.

FIG. 155 depicts a top, side elevational and perspective view of an osteotome handle having a flexible medial calcar spork-shaped blade attached thereto, with the flexible medial calcar spork-shaped blade extending through, and being guided by the guide block assembly and cutting the medial calcar from an implanted femoral stem.

Figures 156, 157:
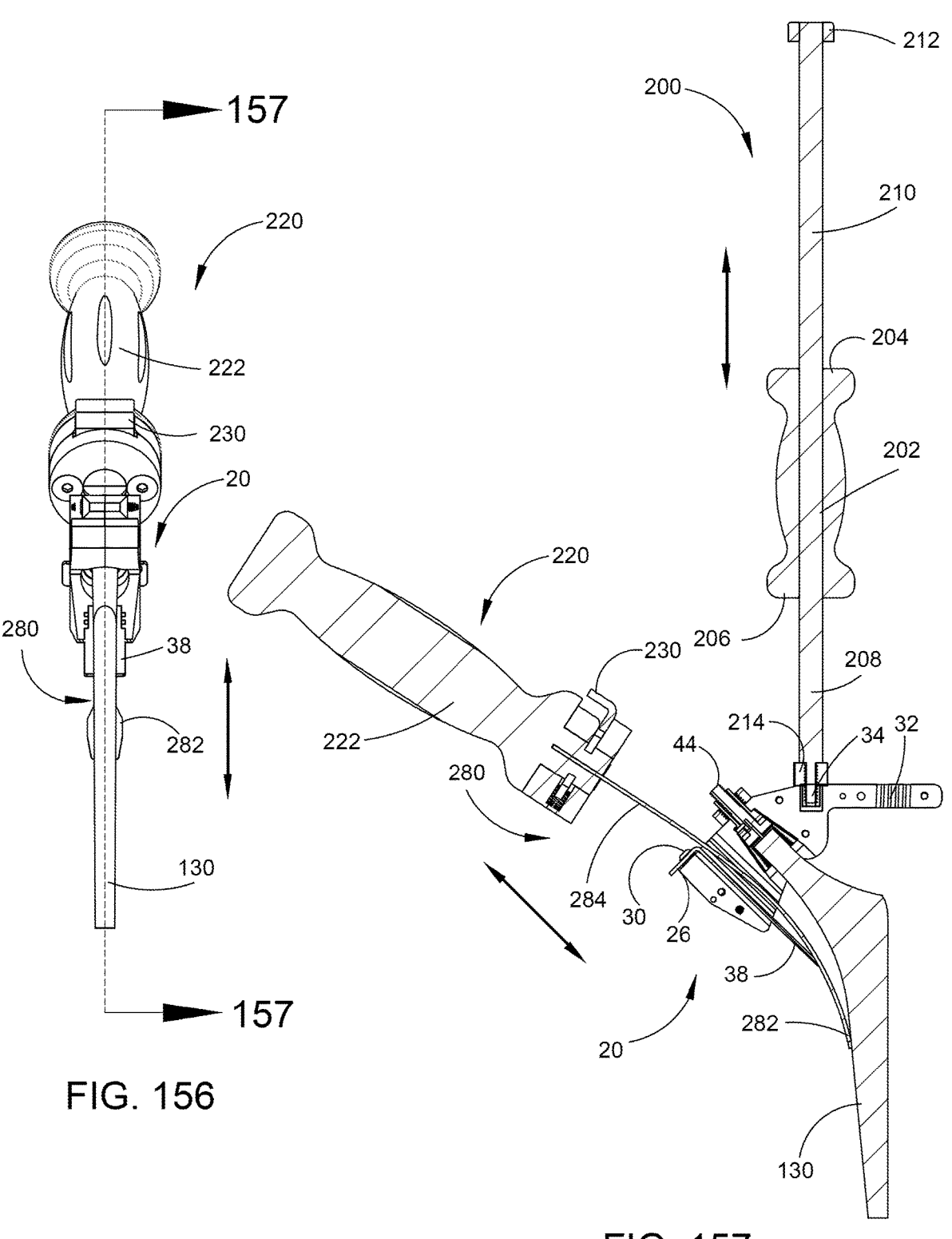

FIG. 156 depicts a rear view of an osteotome handle having a flexible medial calcar spork-shaped blade attached thereto, with the flexible medial calcar spork-shaped blade extending through, and being guided by the guide block assembly and cutting the medial calcar from an implanted femoral stem.

FIG. 157 depicts a cross-sectional view of the osteotome handle having a flexible medial calcar spork-shaped blade attached thereto, with the flexible medial calcar spork-shaped blade extending through, and being guided by the guide block assembly and cutting the medial calcar from an implanted femoral stem, as shown in FIG. 156.

DETAILED DESCRIPTION OF THE PREFERRED EMBODIMENTS

As required, the detailed embodiments of the present Joint Revision Surgery Osteotome Blades and Surgical Chisel Blades 10A, 20, 100, 140, 200, 220, 260, 270, 280, 290, 300, 320, 340, 350 and 370 are disclosed herein, however, it is to be understood that the disclosed embodiments are merely exemplary of the design that may be embodied in various forms. Therefore, specific functional and structural details disclosed herein are not to be interpreted as limiting, but merely as basic for the claims and as a representative basis for teaching one skilled in the art to variously employ the present design in virtually any appropriately detailed structure.

Figure 1:
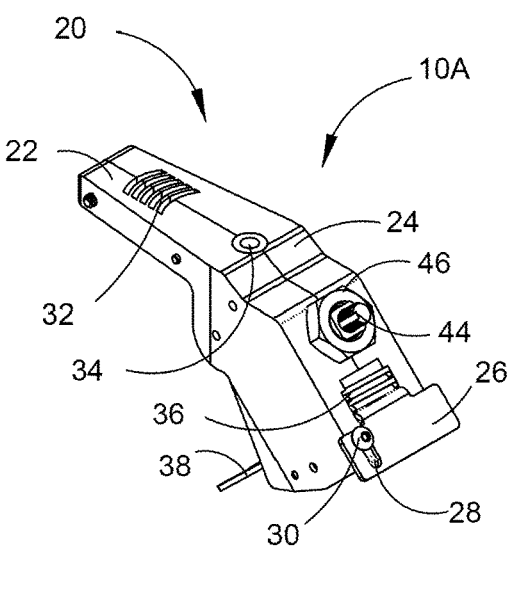
FIG. 1 depicts a top, side elevational and perspective view of an alternate embodiment of the joint revision surgery apparatus illustrating an assembled osteotome blade/surgical chisel guide block having an adjustable L-shaped osteotome blade guide plate fully extended downwardly.

FIG. 1 depicts a top, side elevational and perspective view of an embodiment of the joint revision surgery apparatus 10A illustrating an assembled osteotome blade/surgical chisel guide block 20 (hereinafter referred to as an osteotome blade guide block 20) having an adjustable L-shaped osteotome blade guide plate 38 fully extended downwardly and positioned in the frontmost blade guide slot within the plurality of blade guide slots 36. As previously described in U.S. patent application Ser. No. 17/899,521 and U.S. patent application Ser. No. 18/075,574 both of which US patent applications are hereby incorporated in their entirety herein, the guide block is made from two half sections 22 and 24 held together using Allen screws and alignment pins (see the exploded view in FIG. 23 below). The L-shaped osteotome blade guide plate has an upper portion 26 and a lower portion 38. The guide plate upper portion includes an adjustable guide plate retaining screw slot 28 in which the adjustable guide plate retaining screw 30 is threaded into an threaded orifice (not shown here) with in the guide block assembly 20. Integral to the guide block assembly 20 is a plurality of forward blade guide slots 36 for accepting the adjustable guide plate 38 and the osteotome blades (not shown, see below), and a central cavity 40. The central cavity 40 is configured to accept a trunnion securing member 44 (best seen in FIG. 5), and the trunnion securing member is secured using securing nut 46. Additionally, the assembled guide block 20 defines a plurality of rearward blade guide slots. In this way, the guide block can be adjusted for any size femoral stem implant encountered for removal during revision surgery. The various adjustments are described in greater detail below. This view clearly illustrates the position of the guide plate adjustment screw 30 and the adjustment screw slot 28 within the upper section of the L-shaped guide plate 26. The adjustment screw 30 can be adjusted upwardly and downwardly by threading in or out of the assembled guide block 20, and it can be placed in any of the plurality of blade guide slots 36 within the guide block 20. To move the lower section guide plate 38 to another guide slot in the plurality of guide lots 36, one must unthread and remove the adjustment screw 30 then replace it by sliding it to another position so the guide plate lower section 38 can be placed in a different guide slot 36.

Figure 2:
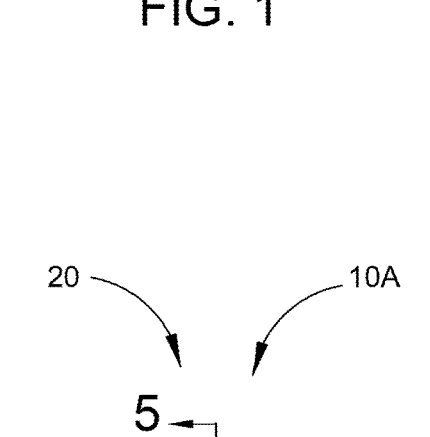
FIG. 2 depicts a side elevational view of an alternate embodiment of the joint revision surgery apparatus illustrating an assembled osteotome blade guide block having an adjustable L-shaped osteotome blade guide plate fully extended downwardly.

FIG. 2 depicts a side elevational view of an embodiment of the joint revision surgery apparatus 10A illustrating an assembled osteotome blade guide block 20 having an adjustable L-shaped osteotome blade guide plate 38 fully extended downwardly. This view better shows the lower guide plate 38 extending downward below the guide block assembly 20.

Figure 3:
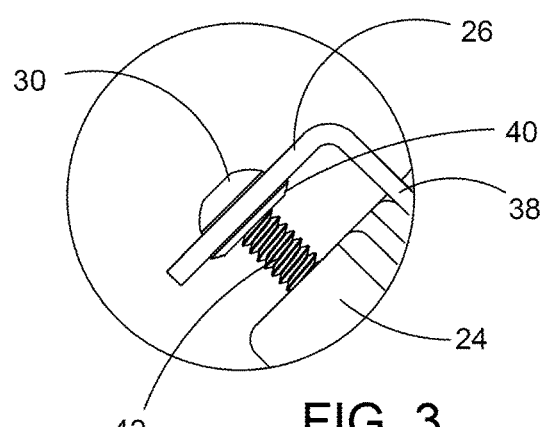
FIG. 3 depicts an enlarged side elevational view of the upper section guide plate and guide plate adjustment screw having an integral retaining washer welded to the underside of the upper section guide plate.

FIG. 3 depicts an enlarged side elevational view of the upper section guide plate 26 and guide plate adjustment screw 30 having an integral retaining washer 40 welded to the underside of the upper section guide plate 26. The guide plate retaining screw 30 here is partially threaded out exposing the threaded section 42. This retaining washer makes it possible for the guide plate upper section 26 to rise and be secured in an upward position when the adjustment plate retaining screw 30 is threaded upwardly or to be lowered when the retaining screw 30 is threaded in downwardly. It is anticipated that a free spinning retaining washer (see retaining washer 41 as shown in FIG. 14) can be used in place of this welded on retaining washer 40 to accomplish the same task of securing the adjustment plate 26 and 38.

Figure 4:
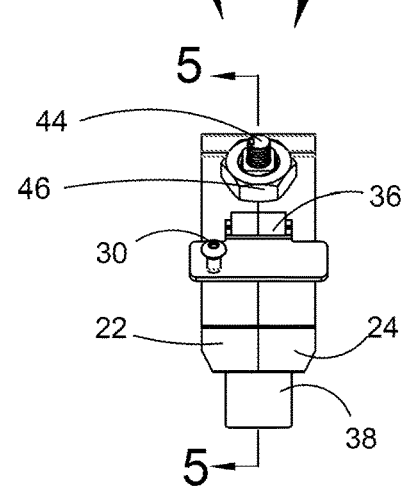
FIG. 4 depicts a front view of an alternate embodiment of the joint revision surgery apparatus illustrating an assembled osteotome blade guide block having an adjustable L-shaped osteotome blade guide plate fully extended downwardly.

FIG. 4 depicts a front view of an alternate embodiment of the joint revision surgery apparatus 10A illustrating an assembled osteotome blade guide block 20 having an adjustable L-shaped osteotome blade guide plate 38 fully extended downwardly. As previously described in U.S. patent application Ser. No. 17/899,521 which application is incorporated in its entirety herein, the guide block is made from two half sections 22 and 24. This view better shows the lower guide plate 38 extending downward into the plurality of forward blade guide slots 36 within the guide block assembly 20.

Figure 5:
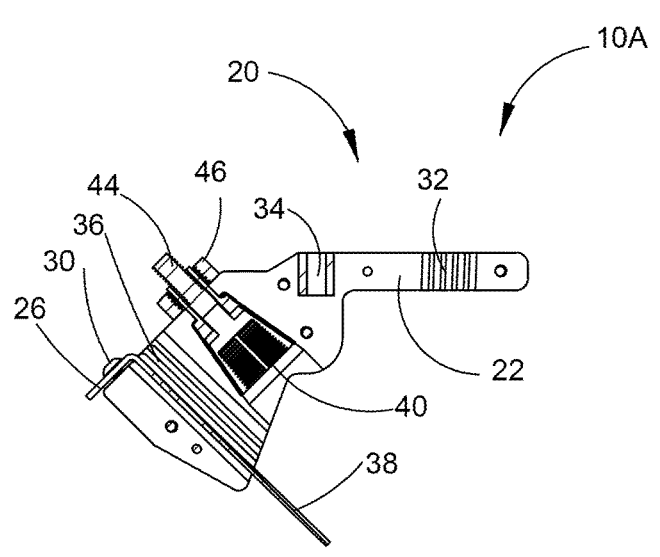
FIG. 5 depicts a cross-sectional view of an alternate embodiment of the joint revision surgery apparatus illustrating an assembled osteotome blade guide block having an adjustable L-shaped osteotome blade guide plate fully extended downwardly of FIG. 4.

FIG. 5 depicts a cross-sectional view of an embodiment of the joint revision surgery apparatus 10A illustrating an assembled osteotome blade/surgical chisel guide block 20 having an adjustable L-shaped osteotome blade guide plate upper section 26 and lower section 38 fully extended downwardly of FIG. 4. This view illustrates the position of the central cavity 40 and the trunnion securing member 44 within the central cavity 40 secured by the securing nut 46. It also clearly shows the plurality of blade guide slots 36 and the lower guide plate 38 extending down into the foremost of the plurality of guide slots 36. The lower guide plate 38 can be adjusted by being positioned in any one of the plurality of guide slots 36 by removing the retaining screw 30 and shifting the lower guide plate 38 to a different slot within the plurality of guide slots 36.

Figures 6, 7, 8, 9, 10:
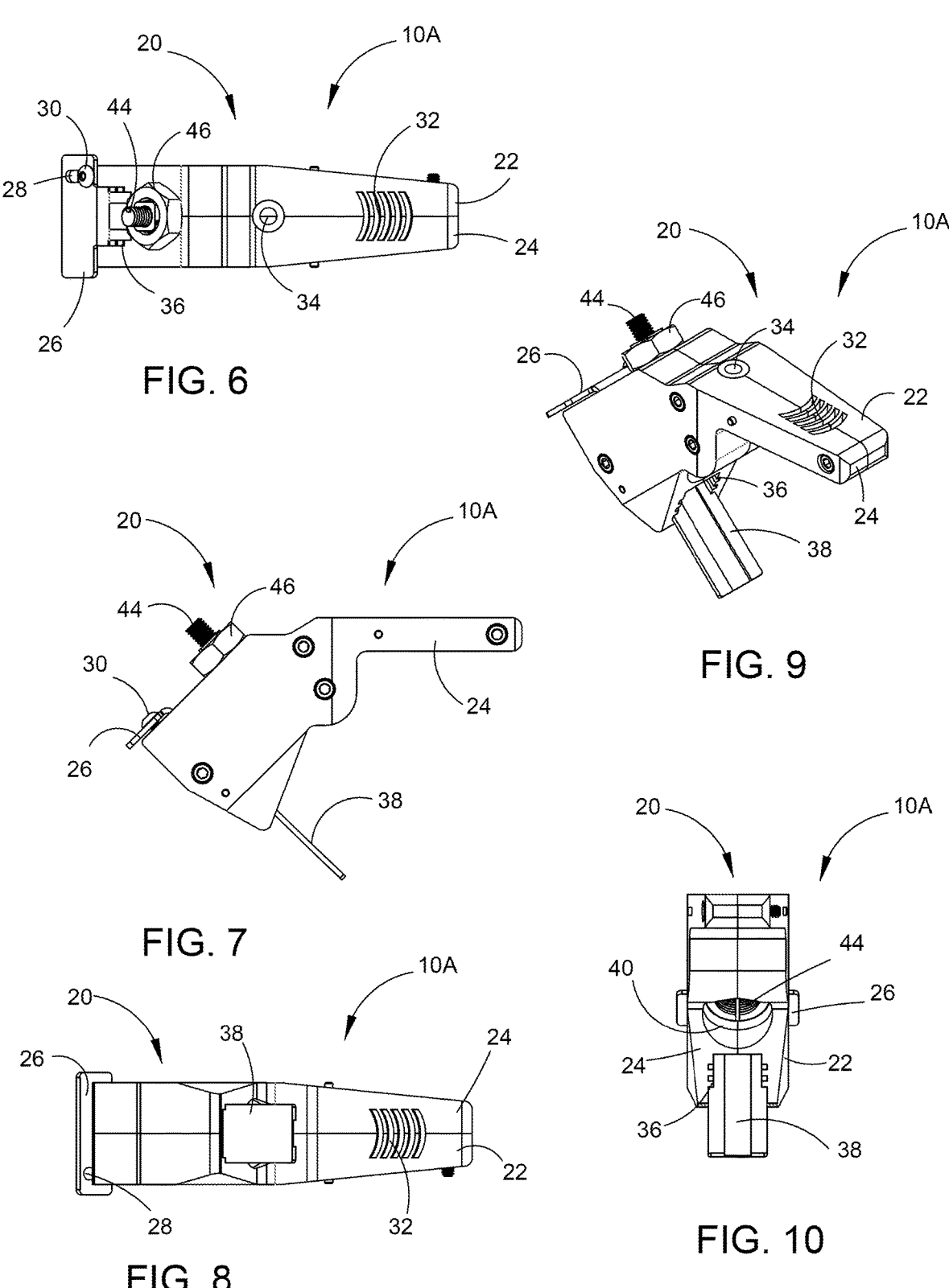
FIG. 6 depicts a top plan view of an alternate embodiment of the joint revision surgery apparatus illustrating an assembled osteotome blade guide block having an adjustable L-shaped osteotome blade guide plate.
FIG. 7 depicts a side elevational view of an alternate embodiment of the joint revision surgery apparatus illustrating an assembled osteotome blade guide block having an adjustable L-shaped osteotome blade guide plate.
FIG. 8 depicts a bottom view of an alternate embodiment of the joint revision surgery apparatus illustrating an assembled osteotome blade guide block having an adjustable L-shaped osteotome blade guide plate.
FIG. 9 depicts a top, side elevational and perspective view of an alternate embodiment of the joint revision surgery apparatus illustrating an assembled osteotome blade guide block having an adjustable L-shaped osteotome blade guide plate.
FIG. 10 depicts a bottom rear view of an alternate embodiment of the joint revision surgery apparatus illustrating an assembled osteotome blade guide block having an adjustable L-shaped osteotome blade guide plate.

FIG. 6 depicts a top plan view of an embodiment of the joint revision surgery apparatus 10A illustrating an assembled osteotome blade guide block 20 having an adjustable L-shaped osteotome blade guide plate. As before, the guide block is made from two half sections 22 and 24 held together using Allen screws and alignment pins (see FIG. 23 below). The L-shaped osteotome blade guide plate has an upper portion 26 and a lower portion 38. The guide plate upper portion includes an adjustable guide plate retaining screw slot 28 in which the adjustable guide plate retaining screw 30 is threaded into an threaded orifice (not shown here) with in the guide block assembly 20. Integral to the guide block assembly 20 is a plurality of forward blade guide slots 36 for accepting the adjustable guide plate 38 and the osteotome blades (not shown, see below), and a central cavity 40. The central cavity 40 is configured to accept a trunnion securing member 44 (best seen in FIG. 14), and the trunnion securing member is secured using securing nut 46. Additionally, the assembled guide block 20 defines a plurality of rearward blade guide slots. Forward of these guide blade slots 32 is a threaded orifice 34 which accepts a T-handle or eyebolt, not shown (see the exploded view in FIG. 23). In this way, the guide block can be adjusted for any size femoral stem implant encountered for removal during revision surgery. The various adjustments are described in greater detail below.

FIG. 7 depicts a side elevational view of an alternate embodiment of the joint revision surgery apparatus 10A illustrating an assembled osteotome blade guide block 20 having an adjustable L-shaped osteotome blade guide plate upper section 26 and lower section 38, which drawing figure includes the same parts. This view better shows the lower guide plate 38 extending downward below the guide block assembly 20.

FIG. 8 depicts a bottom view of an alternate embodiment of the joint revision surgery apparatus 10A illustrating an assembled osteotome blade guide block 20 having an adjustable L-shaped osteotome blade guide plate upper section 26 and lower section 38, which drawing figure includes the same parts. This view better shows the upper guide plate retaining screw slot 28 as well as the rearward blade guide slots 32 integral to the guide block assembly 20.

FIG. 9 depicts a top, side elevational and perspective view of an alternate embodiment of the joint revision surgery apparatus 10A illustrating an assembled osteotome blade guide block 20 having an adjustable L-shaped osteotome blade guide plate upper section 26 and lower section 38, which drawing figure includes the same parts. Forward of the guide blade slots 32 is a threaded orifice 34 which accepts a T-handle or eyebolt, not shown (see the exploded view in FIG. 23). This view better shows the lower guide plate 38 extending downward below the guide block assembly 20 as well as the trunnion securing member 44 retaining nut 46.

FIG. 10 depicts a bottom rear view of an alternate embodiment of the joint revision surgery apparatus 10A illustrating an assembled osteotome blade guide block 20 having an adjustable L-shaped osteotome blade guide plate upper section 26 and lower section 38, which drawing figure includes the same parts. This view better shows the position of the centrally located cavity 40, lower guide plate 38 extending downward below the guide block assembly 20, as well as the central cavity 40 and the plurality of guide blade slots 36.

FIG. 11 depicts a top, side elevational and perspective view of an alternate embodiment of the joint revision surgery apparatus 10A illustrating an assembled osteotome blade guide block 20 having an adjustable L-shaped osteotome blade guide plate upper section 26 and lower section 38 fully retracted upwardly. This view better shows the adjustment slot 28 in the guide plate upper section 26 which allows for the repositioning of the guide plate lower section 38 into differing slots within the plurality of guide slots 36. In this way, the lower guide plate 38 can be positioned in any one of the slots making up the plurality of guide slots 36 and thus, is adjustable forward (toward the femoral stem implant) and backward (away from the femoral stem implant) to accommodate differing sizes of femoral stem implants to be removed during revision surgery.

FIG. 12 depicts a side elevational view of an alternate embodiment of the joint revision surgery apparatus 10A illustrating an assembled osteotome blade guide block 20 having an adjustable L-shaped osteotome blade guide plate upper section 26 and lower section 38 having the lower section guide plate 38 fully retracted upwardly. Here, the retaining screw 30 has been rotated to extend outwardly along screw threads 42. Retaining washer 41 keeps the upper section guide plate 26 from falling back down toward the guide block assembly 20. In this way, the lower guide plate 38 is adjustable upwardly away from the femoral stem implant and downwardly toward the femoral stem implant to accommodate differing sizes of femoral stem implants to be removed during revision surgery.

FIG. 13 depicts a front view of an alternate embodiment of the joint revision surgery apparatus 10A illustrating an assembled osteotome blade guide block 20 having an adjustable L-shaped osteotome blade guide plate 26 and 38 partially retracted upwardly. This front view better shows the threaded portion 42 of retaining screw 30.

FIG. 14 depicts a cross-sectional view of an alternate embodiment of the joint revision surgery apparatus 10A illustrating an assembled osteotome blade guide block 20 having an adjustable L-shaped osteotome blade lower guide plate 38 and upper guide plate section 26 fully retracted upwardly as seen in FIG. 13. Here the guide plate retaining screw 30 has threaded portion 42 all the way out and the upper section guide plate 26 is being held up by retaining washer 41. Again, the lower section guide plate 38 is in the foremost guide slot position within the plurality of guide slots 36. This cross-sectional view also clearly shows the central cavity 40, the trunnion securing member 44 and securing nut 46, along with the rearward blade guide slots 32 and the threaded orifice 34 for accepting an eyebolt (not shown see FIGS. 23-30). This position, farthest from the medial calcar, would accommodate a larger or collared femoral stem implant.

Figures 15, 16, 17, 18:
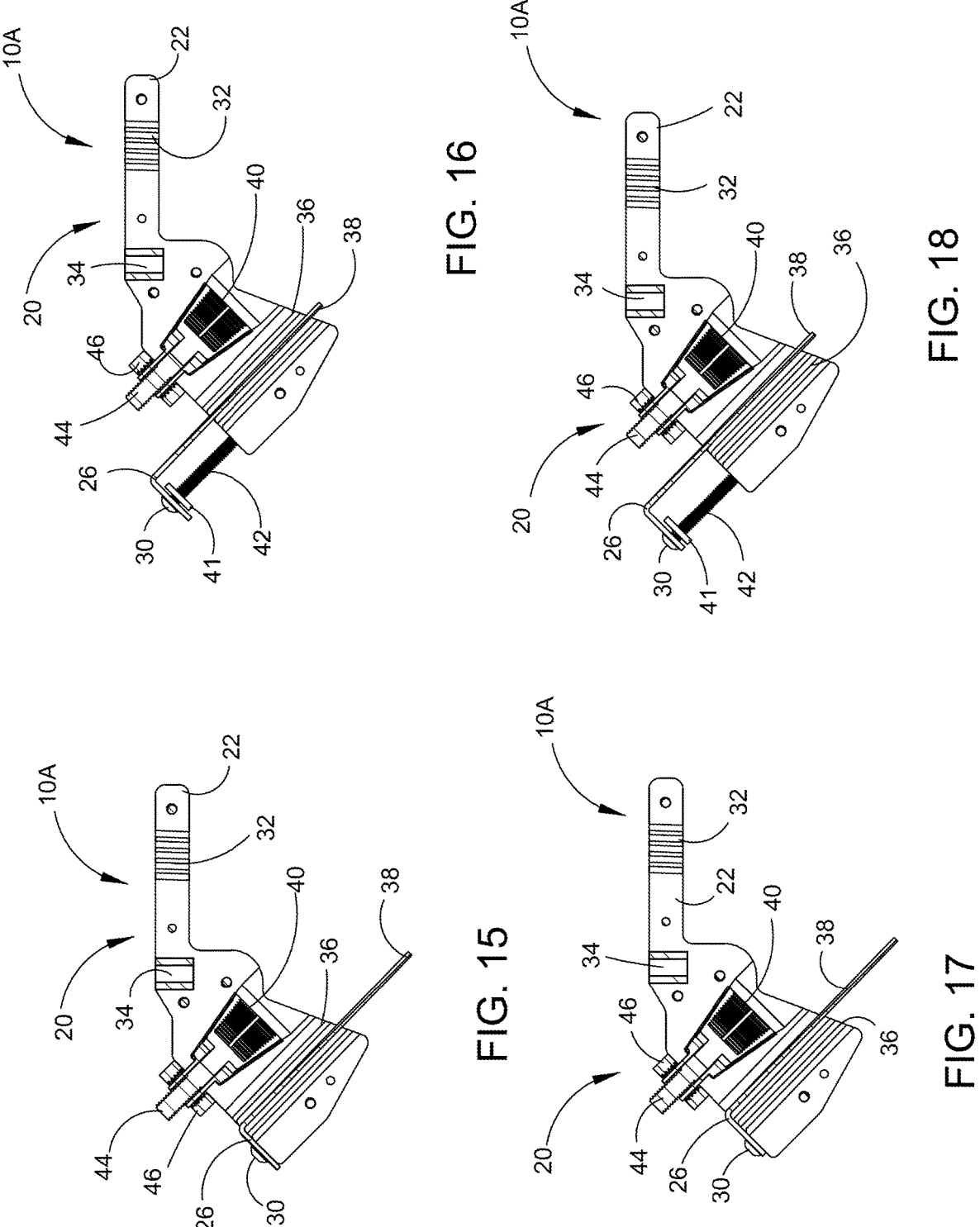
FIG. 15 depicts a cross-sectional view of an alternate embodiment of the joint revision surgery apparatus illustrating an assembled osteotome blade guide block having an adjustable L-shaped osteotome blade guide plate fully extended downwardly and positioned in the middle osteotome blade guide slot within the guide block.
FIG. 16 depicts a cross-sectional view of an alternate embodiment of the joint revision surgery apparatus illustrating an assembled osteotome blade guide block having an adjustable L-shaped osteotome blade guide plate fully retracted upwardly and positioned in the middle osteotome blade guide slot within the guide block.
FIG. 17 depicts a cross-sectional view of an alternate embodiment of the joint revision surgery apparatus illustrating an assembled osteotome blade guide block having an adjustable L-shaped osteotome blade guide plate fully extended downwardly and positioned in the upper most osteotome blade guide slot within the guide block.
FIG. 18 depicts a cross-sectional view of an alternate embodiment of the joint revision surgery apparatus illustrating an assembled osteotome blade guide block having an adjustable L-shaped osteotome blade guide plate fully retracted upwardly and positioned in the upper most osteotome blade guide slot within the guide block.

FIG. 15 depicts a cross-sectional view of an alternate embodiment of the joint revision surgery apparatus 10A illustrating an assembled osteotome blade guide block 20 having an adjustable L-shaped osteotome blade guide plate upper section 26 and lower section 38 fully extended downwardly and positioned in the middle osteotome blade guide slot within the guide block. This view clearly shows that the lower section guide plate 38 has been moved and repositioned in one of the middle guide slots within the plurality of guide slots 36. This position, a medium distance to the medial calcar, would accommodate a medium sized femoral stem implant.

FIG. 16 depicts a cross-sectional view of an alternate embodiment of the joint revision surgery apparatus 10A illustrating an assembled osteotome blade guide block 20 having an adjustable L-shaped osteotome blade guide plate lower section 38 fully retracted upwardly and positioned in the middle osteotome blade guide slot within the plurality of guide slots 36 integral to the guide block assembly 700. It also shows the retaining washer 41 which holds the upper section guide plate 26 in the upward position.

FIG. 17 depicts a cross-sectional view of an alternate embodiment of the joint revision surgery apparatus 10A illustrating an assembled osteotome blade guide block 20 having an adjustable L-shaped osteotome blade guide plate upper section 26 and lower section 38 fully extended downwardly and positioned in the osteotome blade guide slot closest to the central cavity 40 within the guide block. This view clearly shows that the lower section guide plate 38 has been moved and repositioned in the closest guide slot to the central cavity 40 and thereby, is now positioned closest to the femoral stem implant to be removed during revision surgery. This position, closest to the medial calcar, would accommodate a smaller femoral stem implant.

Figures 19, 20, 21, 22:
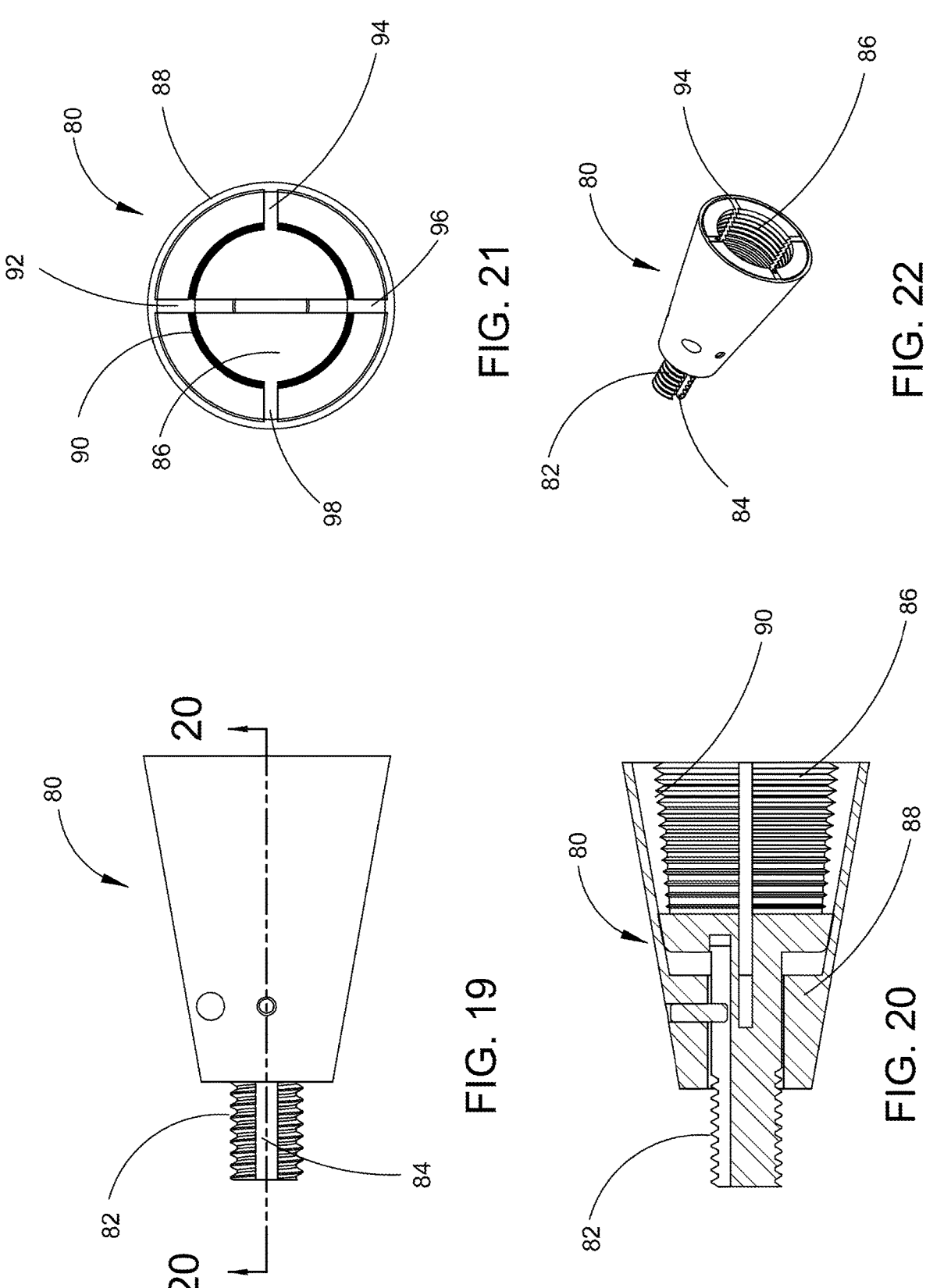
FIG. 19 depicts a side view of a stem trunnion securing piece.
FIG. 20 depicts a cross-sectional view of the stem trunnion securing piece, as shown in FIG. 19.
FIG. 21 depicts a bottom view of a stem trunnion securing piece.
FIG. 22 depicts a side perspective view of a stem trunnion securing piece.

FIG. 18 depicts a cross-sectional view of an alternate embodiment of the joint revision surgery apparatus 10A illustrating an assembled osteotome blade guide block 20 having an adjustable L-shaped osteotome blade guide plate lower section 38 fully retracted upwardly and positioned in the osteotome blade guide slot closest to the central cavity 40 within the plurality of guide slots 36 integral to the guide block assembly 20. It also shows the retaining washer 41 which holds the upper section guide plate 26 in the upward position. This position, closest to the medial calcar but fully retracted upwardly, would accommodate a smaller to medium sized femoral stem implant. Referring now to FIG. 19, this view in FIG. 19 depicts a side elevational view of a stem trunnion securing piece 80 having a threaded portion 82 and a groove 84 running the length of the threaded portion 82. The stem trunnion securing piece 80 is conical in shape and tapers from a large diameter to a small diameter towards the threaded portion 82. The groove 84 is used to orient mounting the stem trunnion securing piece 80 within the central cavity 40 of the assembly 20 and when mounted therein, to keep the stem trunnion securing piece 80 from rotating during a revision surgery operation.

FIG. 20 depicts a cross-sectional view of the stem trunnion securing piece 80, as shown in FIG. 19. The stem trunnion securing piece 80 has a partially hollow body 88, having a ribbed inner portion 86 running roughly half way from the large diameter to the small diameter proximal to the threaded portion 82. Within the outer body 88 of the stem trunnion securing piece 80 is a ribbed inner portion 86 having a plurality of circular ribs 90 thereon. The ribbed inner portion 86 is slidably affixed to the outer body. The ribbed inner portion 90 within the hollow section 86 also has exterior slots (not shown, see FIGS. 21 and 22 below). When the nut 46 is placed on the threaded portion 82 and tightened, this moves the inner ribbed portion 86 upwardly the outer body 88 of the stem trunnion securing piece 80 and tightens the stem trunnion securing piece 80 around the stem trunnion 132 (see FIG. 24), by decreasing the overall diameter of the inner ribbed portion 86. See further description of this operation below.

FIG. 21 depicts a bottom view of a stem trunnion securing piece 80 illustrating the outer body 88 and the inner ribbed portion 90 within the hollow section 86. Four slots 92, 94, 96 and 98 are located at 90 degrees from each other around the ribbed inner portion 86. In operation, the stem trunnion securing piece 80 is placed on the stem trunnion 132 and the plurality of circular ribs 90 make contact with the stem trunnion 132 upper section. When the nut 46 is placed on the threaded portion 82 and tightened, this moves the inner ribbed portion upwardly in the outer body 88 and tightens the stem trunnion securing piece 80 around the stem trunnion 132 by decreasing the overall diameter of the ribbed inner portion 86 around the stem trunnion. The four slots 92, 94, 96 and 98 pinch together and the slot gap distance decreases as the nut 46 is tightened and the inner ribbed portion 86 moves relative to the outer body 88. This effectively tightly and securely clamps the stem trunnion securing piece 80 to the stem trunnion 132. Once secured, the stem trunnion 80 cannot be released from the stem trunnion securing piece 80 until the nut 46 is loosened and the diameter of the ribbed inner portion 86 is increased to its original size. The nut 46 may be tightened and loosened using a standard wrench, such as a 10 mm box wrench.

FIG. 22 depicts a side perspective view of a stem trunnion securing piece 80 illustrating the threaded portion 82 having a slot 84 therein, and the inner ribbed portion 86 having four slots therein, here with one slot 94 shown labeled by a reference character. It is anticipated that varying sizes of the stem trunnion securing piece 80 will be made available to accommodate the varying sizes of the stem trunnions to be extracted. Different sizes of the stem trunnion securing piece 80 will be readily mounted by placing the stem trunnion securing piece 80 into the central cavity 40 then securing it in place using the nut 46. In this way, the stem trunnion securing piece 80 will also be replaceable and reusable as when the nut 46 is loosened the stem trunnion 132 is released after extraction of the stem.

Figure 23:
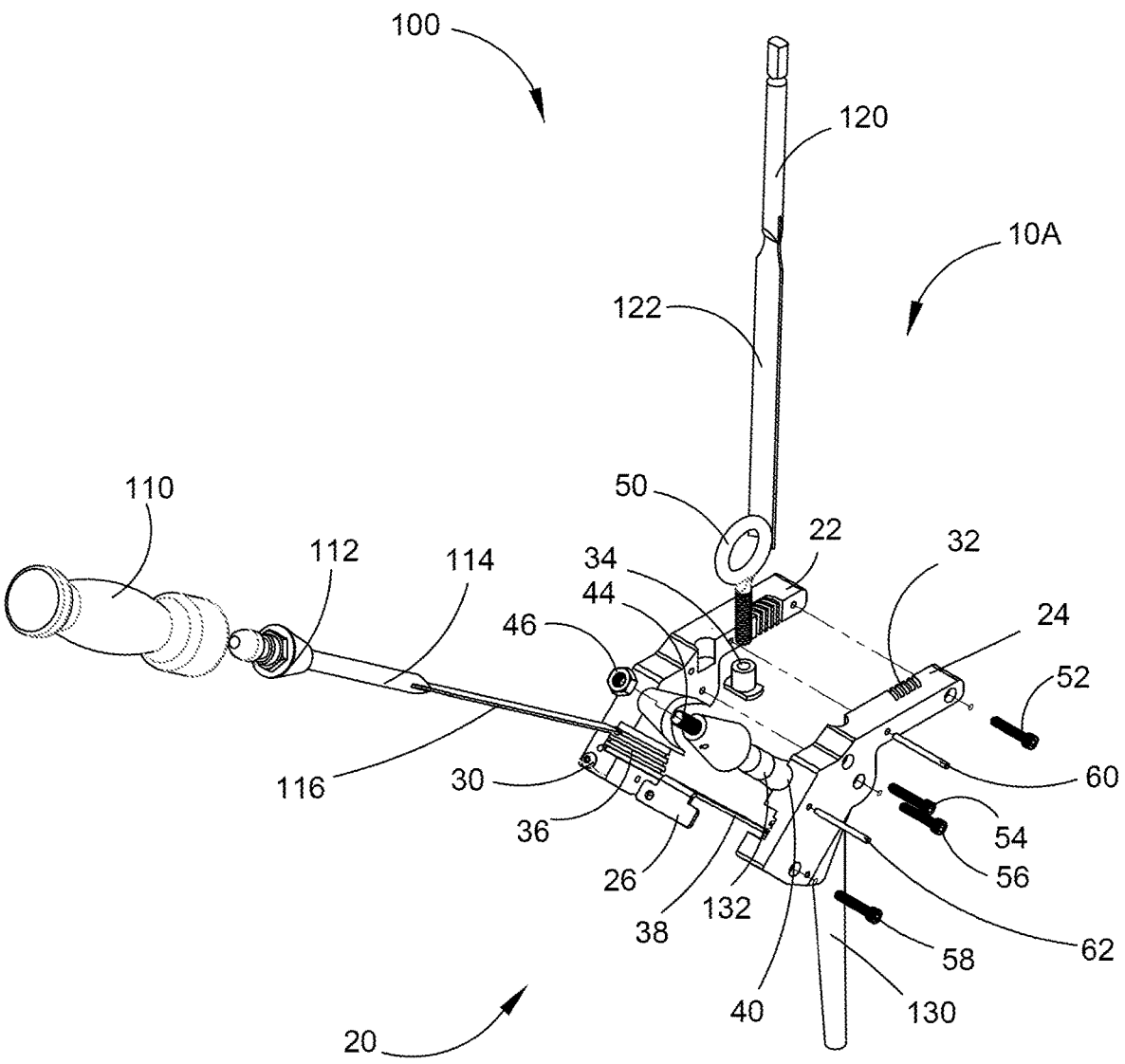
FIG. 23 depicts an exploded view of the alternate embodiment of the joint revision surgery apparatus illustrating an assembled osteotome blade guide block having an adjustable L-shaped osteotome blade guide plate, illustrating the position of the osteotome blades before insertion into the forward and rearward osteotome blade guide slots within the guide block.

FIG. 23 depicts an exploded view of the alternate embodiment of the joint revision surgery apparatus 10A illustrating a disassembled osteotome blade guide block assembly 20 having an adjustable L-shaped osteotome blade guide plate 26 and 38, and showing its use during revision surgery 100 with respect to the relative positions of the medial calcar osteotome blade 116 and posterior osteotome blade 122 before insertion into the forward osteotome blade guide slots 36 and rearward osteotome blade guide slots 32 within the guide block assembly 20, as its relative position to the femoral stem implant 130 and femoral stem implant trunnion portion 132. Assembly of the two half sections 22 and 24 is accomplished using Allen screws 52, 54, 56 and 58 along with alignment pins 60 and 62. Also shown is eyebolt 50 and female threaded orifice 34 to accept the male threaded eyebolt 50. The medial calcar blade 116 includes blade shaft 114 is attached to handle adapter 112 which allows for fastening to handle 110. The posterior blade 122 includes blade shaft 120.

Figure 24:
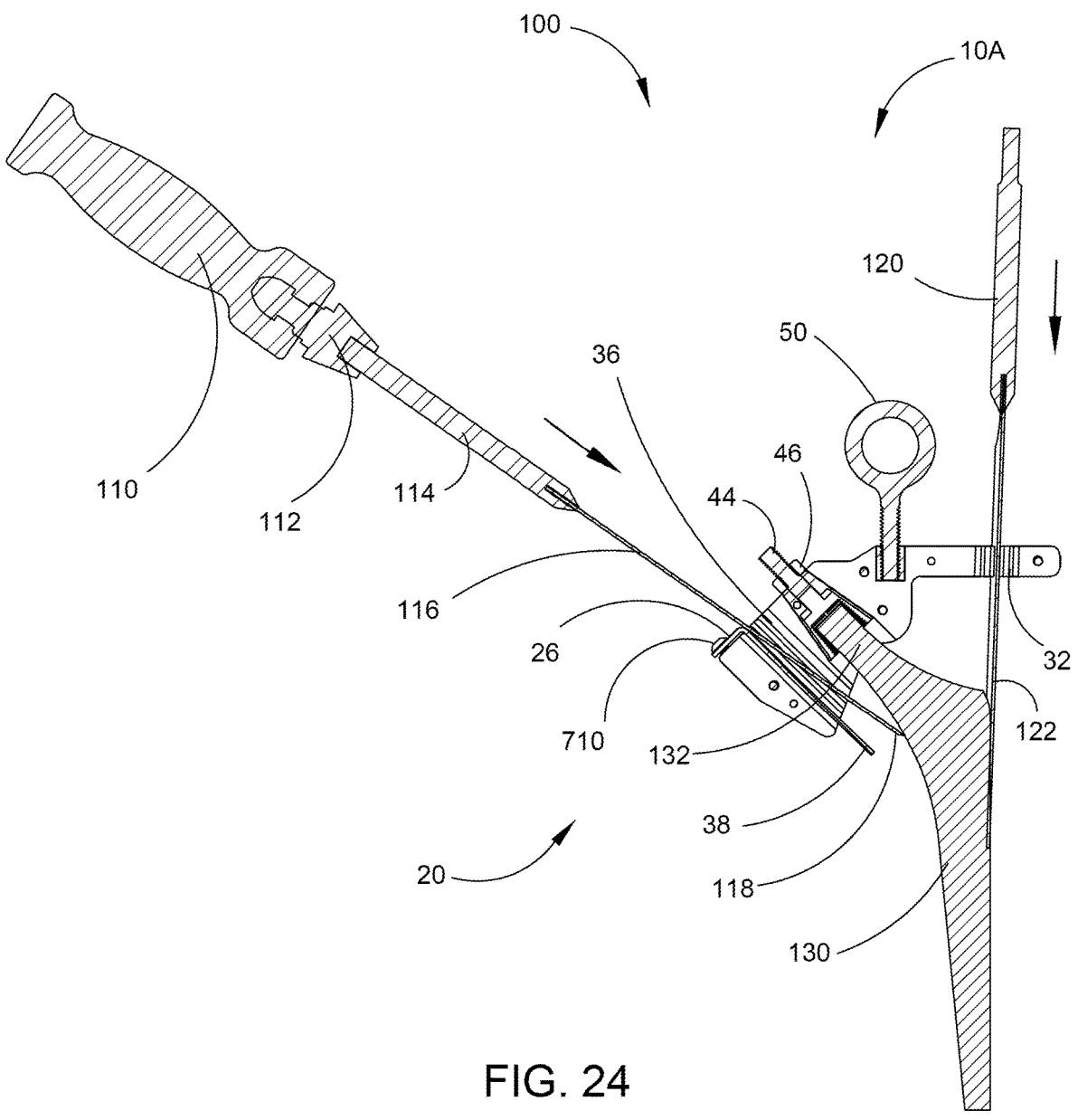
FIG. 24 depicts a cross-sectional view of the alternate embodiment of the joint revision surgery apparatus illustrating an assembled osteotome blade guide block having an adjustable L-shaped osteotome blade guide plate, showing the surgical osteotome blades inserted into the forward and rearward osteotome blade guide slots within the guide block, for removal of a non-collared implanted femoral stem.

FIG. 24 depicts a cross-sectional view of the alternate embodiment of the joint revision surgery apparatus 10A illustrating an assembled osteotome blade guide block 20 having an adjustable L-shaped osteotome blade guide plate, in use during revision surgery 100 showing the surgical osteotome blades 116 and 122 inserted into the forward 36 and rearward 32 osteotome blade guide slots within the assembled guide block 20, for removal of a non-collared implanted femoral stem 130. Note that the guide plate lower section 38 has been inserted into the farthest most guide slot (away from the femoral stem implant) within the plurality of guide slots 36. Also, note that the guide plate adjustment screw 30 is threaded all the way into the block such that the guide plate lower section 38 is farthest from the femoral stem implant to be removed. Trunnion securing member 44 is securely fastened to the trunnion portion 132 of the stem 130. Posterior blade shaft 120 and cutting blade 122 extend down through rearward guides slots 32 and cut the posterior portion of the non-collared implanted femoral stem 130. Medial calcar blade 116 runs down through the plurality of guide slots 36 and is guided by the position of the guide plate lower section 38. The blade 116 makes contact with the non-collared implanted femoral stem 130. This FIG. 24 represents Steps 1-4 of the procedure for revision surgery to remove a femoral stem implant, namely, Step 1: adjust the guide plate height and slot position for the type and size of the femoral stem implant to be removed; Step 2: secure the trunnion portion 132 to the trunnion securing member 44; Step 3: insert the posterior cutting blade through the rearward blade guide slots 32; Step 4: after all adjustments have been made to the guide plate, and the rearward or posterior cutting blade 122 has been inserted, then the medial calcar blade 116 insertion is initiated. In this way, the correct and appropriate adjustments have been made to accommodate the size and shape of the femoral stem implant 130 to be removed during the subsequent steps of the revision surgery procedure using the joint revision surgery apparatus 10A guide block assembly 20.

Figure 25:
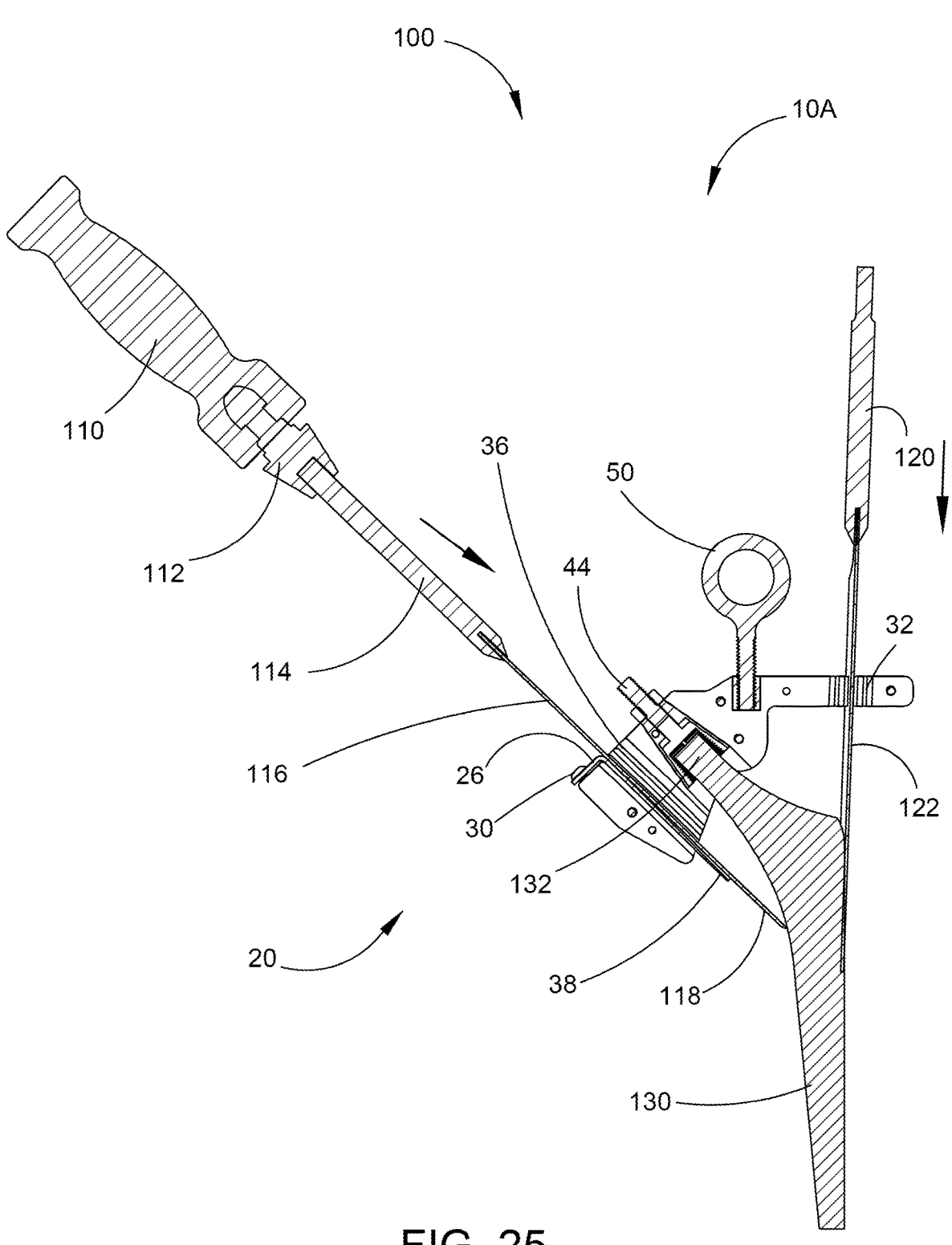
FIG. 25 depicts a cross-sectional view of the alternate embodiment of the joint revision surgery apparatus illustrating an assembled osteotome blade guide block having an adjustable L-shaped osteotome blade guide plate, showing the surgical osteotome blades inserted into the forward and rearward osteotome blade guide slots within the guide block, for removal of a non-collared implanted femoral stem.

FIG. 25 depicts a cross-sectional view of the alternate embodiment of the joint revision surgery apparatus 10A illustrating an assembled osteotome blade guide block 20 having an adjustable L-shaped osteotome blade guide plate 26 and 38, in use during revision surgery 100 showing the surgical osteotome blades 116 and 122 inserted into the forward 36 and rearward 32 osteotome blade guide slots within the assembled guide block 20, for removal of a non-collared implanted femoral stem. This FIG. 25 represents Step 5 of the procedure for revision surgery to remove a femoral stem implant, namely, Step 5: insert medial calcar cutting blade 116 until it makes contact with the femoral stem implant 130 to be removed.

Figure 26:
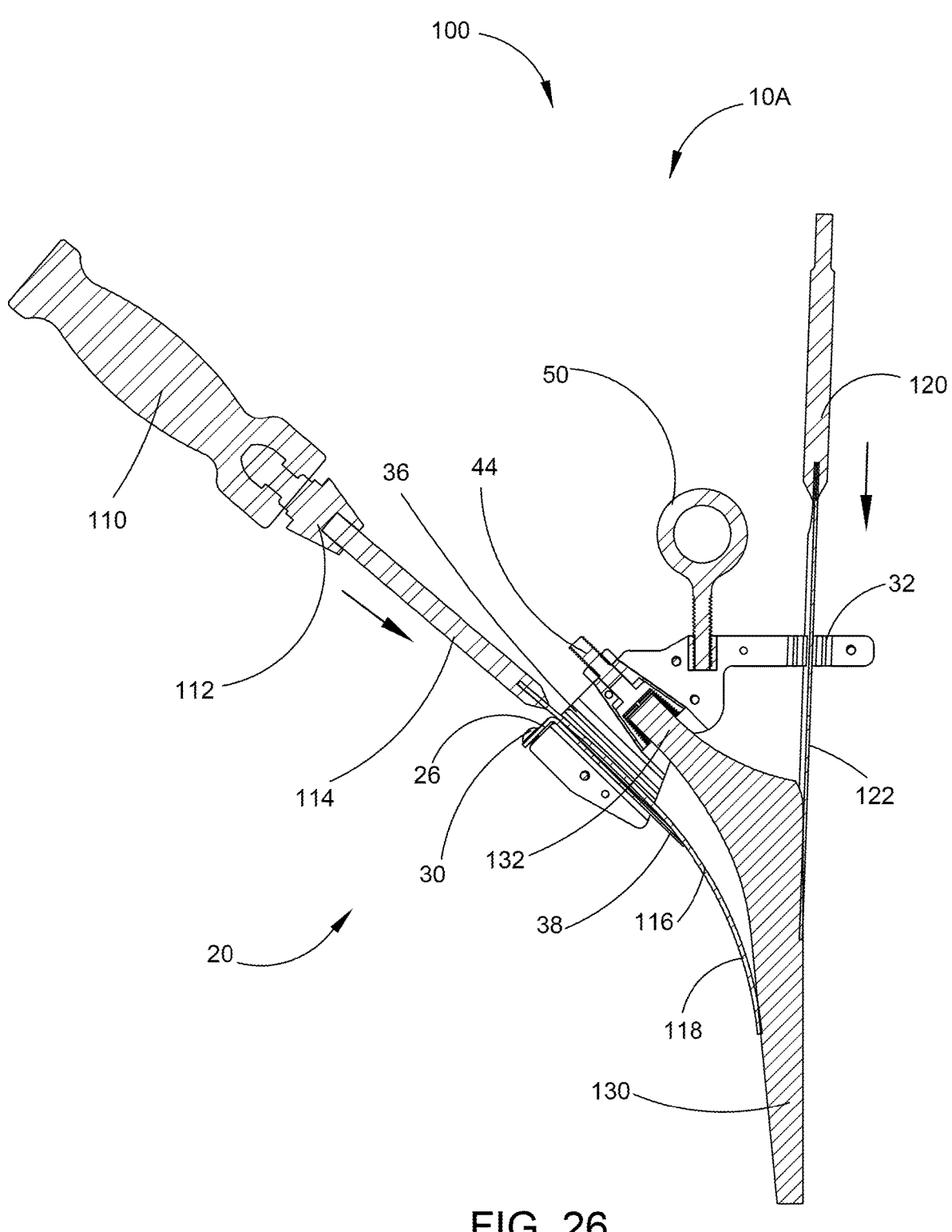
FIG. 26 depicts a cross-sectional view of the alternate embodiment of the joint revision surgery apparatus illustrating an assembled osteotome blade guide block having an adjustable L-shaped osteotome blade guide plate, showing the osteotome blades inserted into the forward and rearward osteotome blade guide slots within the guide block, for removal of a non-collared implanted femoral stem.

FIG. 26 depicts a cross-sectional view of the alternate embodiment of the joint revision surgery apparatus 10A illustrating an assembled osteotome blade guide block 20 having an adjustable L-shaped osteotome blade guide plate 26 and 38, in use during revision surgery 100 showing the surgical osteotome blades 116 and 122 inserted into the forward 36 and rearward 32 osteotome blade guide slots within the assembled guide block 20, for removal of a non-collared implanted femoral stem. This FIG. 26 represents Step 6 of the procedure for revision surgery to remove a non-collared implanted femoral stem implant 130, namely, Step 6: continue downward pressure and motion of the medial calcar cutting blade 116 until it advances past the point of initial contact with the femoral stem implant 130 to be removed, and begins cutting the femoral stem implant away from the femur bone. In this FIG. 26 note that the L-shaped guide plate 26 and 38 are positioned within the guide slot farthest away from the femoral stem implant 130. Also note that the guide plate lower section 38 is secured at its lowest point possible, closest to the femoral stem implant 130 to be removed during revision surgery.

Figure 27:
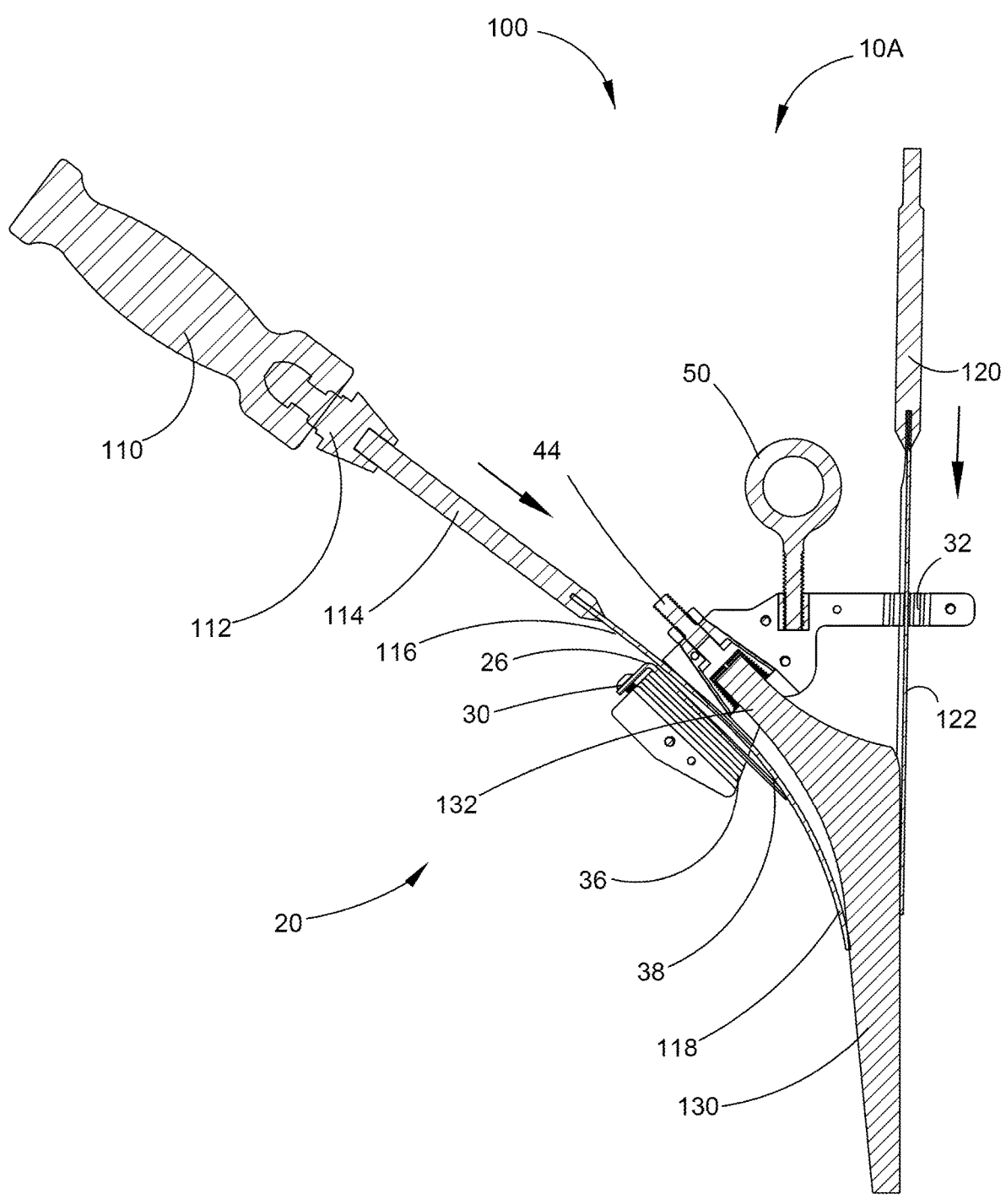
FIG. 27 depicts a cross-sectional view of the alternate embodiment of the joint revision surgery apparatus illustrating an assembled osteotome blade guide block having an adjustable L-shaped osteotome blade guide plate, showing the osteotome blades inserted into the forward and rearward osteotome blade guide slots within the guide block, for removal of a non-collared implanted femoral stem.

FIG. 27 depicts a cross-sectional view of the alternate embodiment of the joint revision surgery apparatus 10A illustrating an assembled osteotome blade guide block 20 having an adjustable L-shaped osteotome blade guide plate 26 and 38, in use during revision surgery 100 showing the surgical osteotome blades 116 and 122 inserted into the forward 36 and rearward 32 osteotome blade guide slots within the assembled guide block 20, for removal of a non-collared implanted femoral stem. This FIG. 27 again represents Step 6 of the procedure for revision surgery to remove a femoral stem implant 130, namely, Step 6: continue downward pressure and motion of the medial calcar cutting blade 116 until it advances past the point of initial contact with the femoral stem implant 130 to be removed, and begins cutting the femoral stem implant away from the femur bone. In this FIG. 27 note that the L-shaped guide plate 26 and 38 are positioned within the guide slot closest to the non-collared femoral stem implant 130. Also note that the guide plate lower section 38 is secured at a slightly raised position relative to its lowest point possible, a bit farther away from the non-collared femoral stem implant 130 to be removed during revision surgery.

Figure 28:
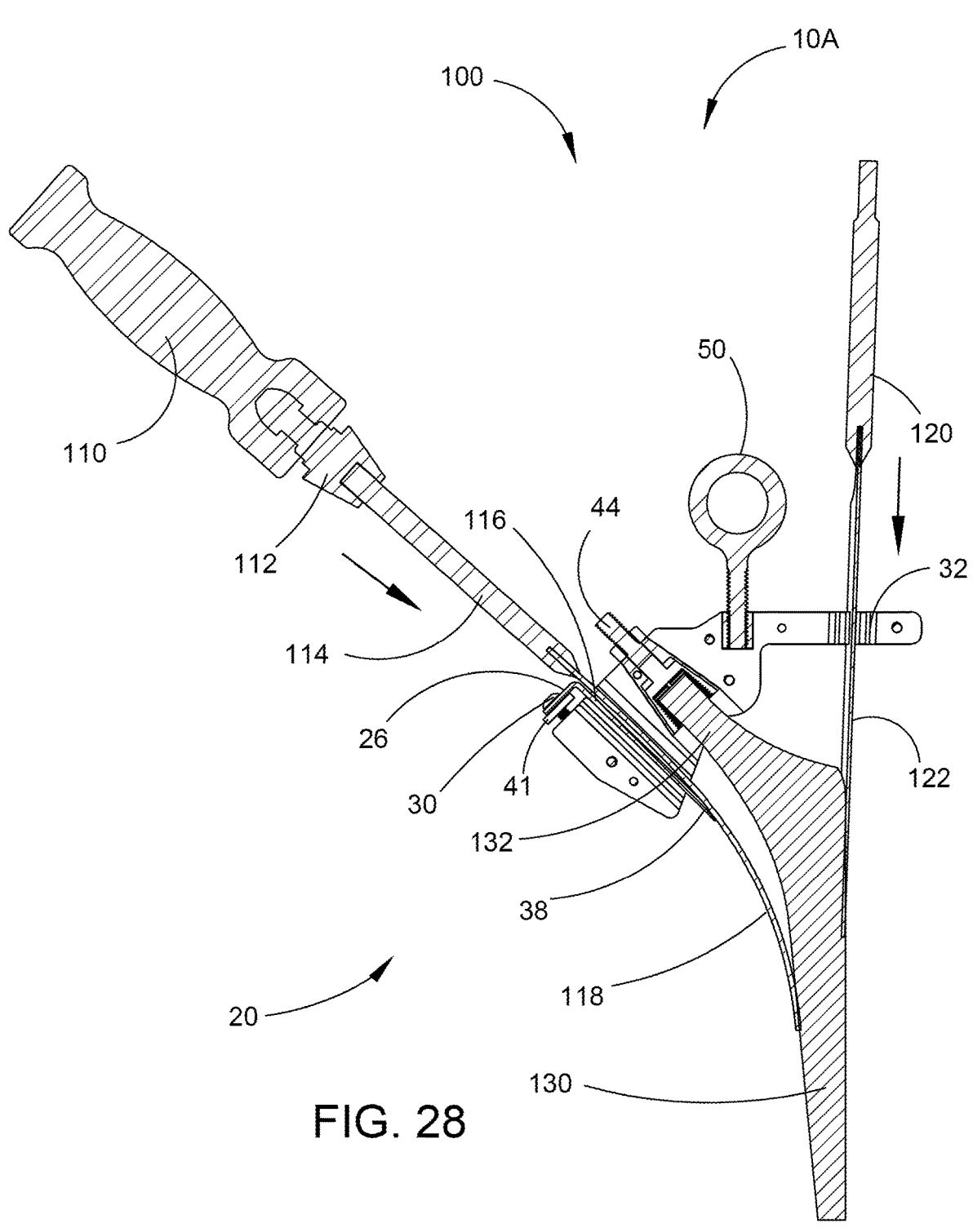
FIG. 28 depicts a cross-sectional view of the alternate embodiment of the joint revision surgery apparatus illustrating an assembled osteotome blade guide block having an adjustable L-shaped osteotome blade guide plate, showing the osteotome blades inserted into the forward and rearward osteotome blade guide slots within the guide block, for removal of a non-collared implanted femoral stem.

FIG. 28 depicts a cross-sectional view of the alternate embodiment of the joint revision surgery apparatus 10A illustrating an assembled osteotome blade guide block 20 having an adjustable L-shaped osteotome blade guide plate 26 and 38, in use during revision surgery 100 showing the surgical osteotome blades 116 and 122 inserted into the forward 36 and rearward 32 osteotome blade guide slots within the assembled guide block 20, for removal of a non-collared implanted femoral stem. This FIG. 28 again represents Step 6 of the procedure for revision surgery to remove a femoral stem implant 130, namely, Step 6: continue downward pressure and motion of the medial calcar cutting blade 116 until it advances past the point of initial contact with the femoral stem implant 130 to be removed, and begins cutting the femoral stem implant away from the femur bone. In this FIG. 28 note that the L-shaped guide plate 26 and 38 are positioned within the guide slot closest to the femoral stem implant 130. This view better shows the retaining washer 41 used to keep the guide plate upper section 26 up when the adjustment plate retaining screw 30 is raised. Also note that the guide plate lower section 38 is secured at a more raised position relative to its lowest point possible, a bit farther away from the femoral stem implant 130 to be removed during revision surgery.

Figure 29:
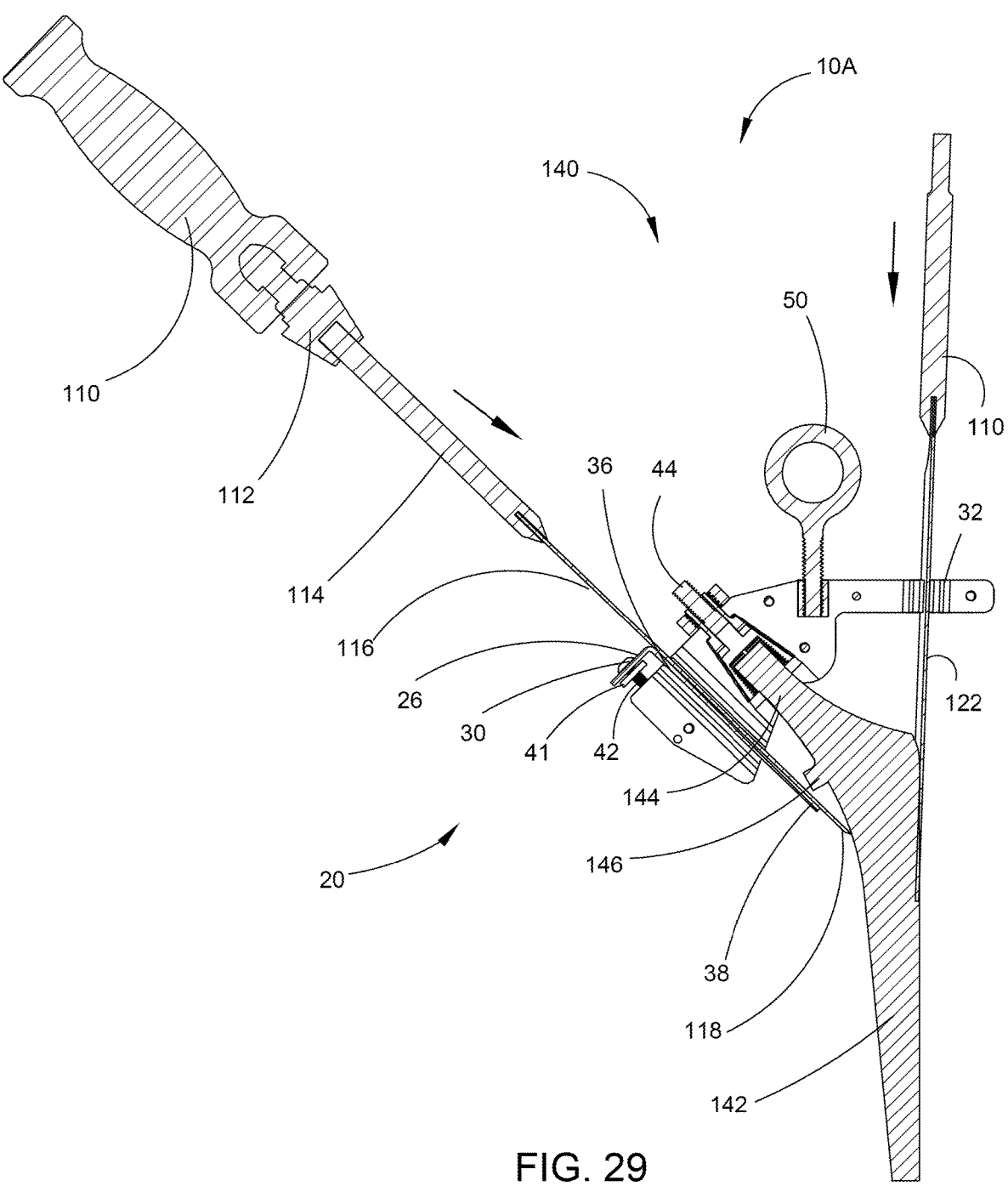
FIG. 29 depicts a cross-sectional view of the alternate embodiment of the joint revision surgery apparatus illustrating an assembled osteotome blade guide block having an adjustable L-shaped osteotome blade guide plate, showing the osteotome blades inserted into the forward and rearward osteotome blade guide slots within the guide block, for removal of a collared implanted femoral stem.

FIG. 29 depicts a cross-sectional view of the alternate embodiment of the joint revision surgery apparatus 10A illustrating an assembled osteotome blade guide block 20 having an adjustable L-shaped osteotome blade guide plate 26 and 38, in use during revision surgery 140 showing the surgical osteotome blades 116 and 122 inserted into the forward 36 and rearward 32 osteotome blade guide slots within the assembled guide block 20, for removal of a collared implanted femoral stem 142 including a collar 146. The femoral stem trunnion section 144 has been secured to the trunnion securing member 44. This FIG. 29 represents Step 5 of the procedure for revision surgery to remove a collared femoral stem implant, namely, Step 5: inserting the medial calcar cutting blade 116 until it makes initial contact with the collared femoral stem implant 140 to be removed, here bypassing the collar 146 on the collared stem 142. In this FIG. 29 note that the L-shaped guide plate 26 and 38 are positioned within the guide slot in the middle section of the plurality of guide slots 26 a medium distance from the collared femoral stem implant 142. Also note that the adjustment plate retaining screw 30 is slightly raised allowing the guide plate lower section 38 to guide a cutting blade 116 beneath the collar 146 on the collared stem 142. This view better shows the retaining washer 41 used to keep the guide plate upper section 26 up when the adjustment plate retaining screw 30 is raised. Also note that the guide plate lower section 38 is secured at a more raised position relative to its lowest point possible, a bit farther away from the collared femoral stem implant 142 to be removed during revision surgery.

Figure 30:
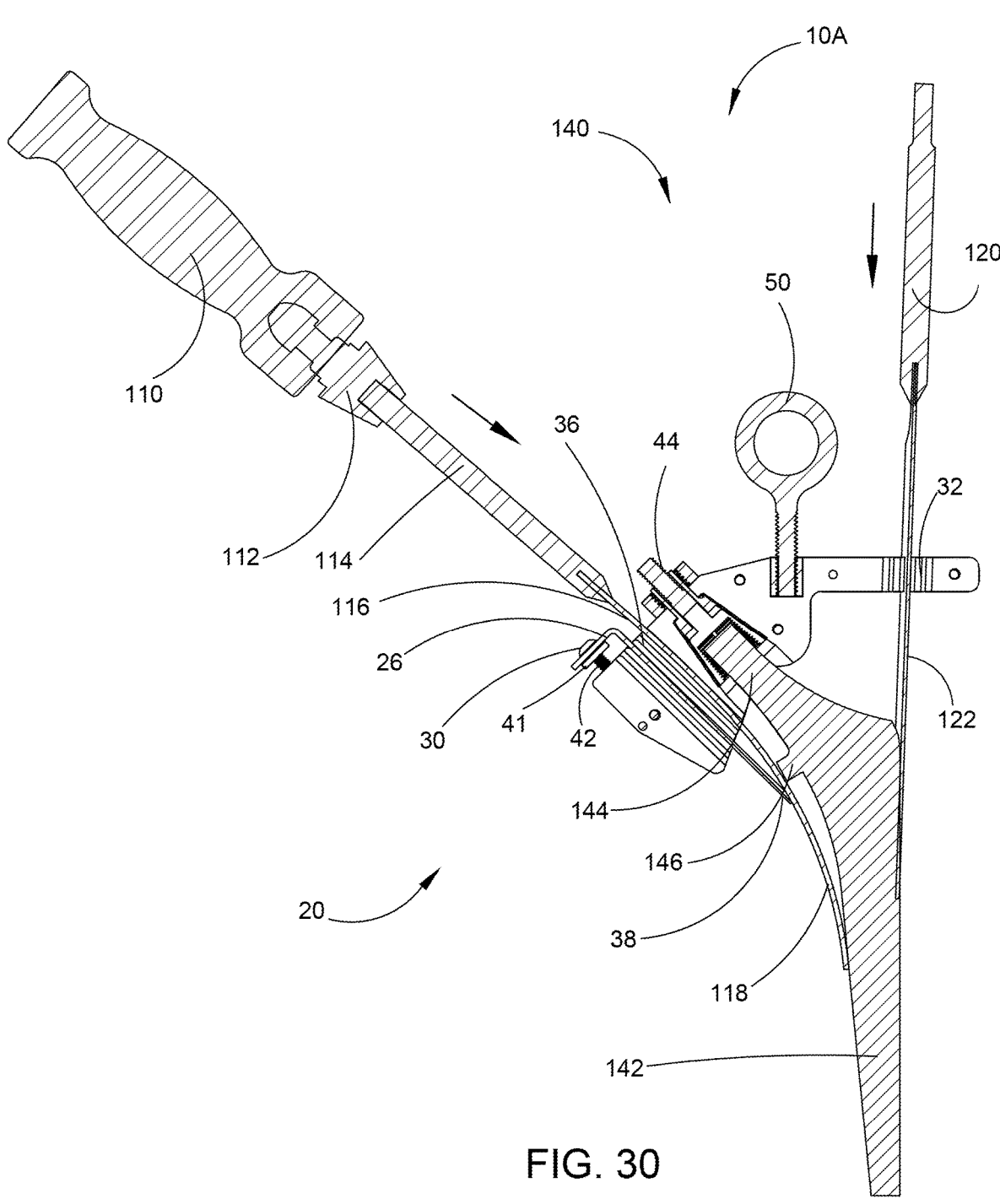
FIG. 30 depicts a cross-sectional view of the alternate embodiment of the joint revision surgery apparatus illustrating an assembled osteotome blade guide block having an adjustable L-shaped osteotome blade guide plate, showing the osteotome blades inserted into the forward and rearward osteotome blade guide slots within the guide block, for removal of a collared implanted femoral stem.

FIG. 30 depicts a cross-sectional view of the alternate embodiment of the joint revision surgery apparatus 10A illustrating an assembled osteotome blade guide block 20 having an adjustable L-shaped osteotome blade guide plate 26 and 38, in use during revision surgery 140 showing the surgical osteotome blades 116 and 122 inserted into the forward 36 and rearward 32 osteotome blade guide slots within the assembled guide block 20, for removal of a collared implanted femoral stem 142. The collared femoral stem trunnion section 144 has been secured to the trunnion securing member 44. This FIG. 30 again represents Step 6 of the procedure for revision surgery to remove a collared femoral stem implant 142, namely, Step 6: continue downward pressure and motion of the medial calcar cutting blade 116 until it advances past the point of initial contact with the collared femoral stem implant 142 to be removed, and begins cutting the collared femoral stem implant 142 away from the femur bone. In this FIG. 30 note that the L-shaped guide plate 26 and 38 are positioned within the guide slot closest to the collared femoral stem implant 142. Note that the guide plate lower section 38 is secured at a more raised position relative to its lowest point possible, a bit farther away from the collared femoral stem implant 142 to be removed during revision surgery. This allows the guide plate 38 to guide the cutting blade 116 down passed the collar 146 on the collared stem 142. These two aforementioned two-way distance adjustments allow the guide block 20 to be used with varying sized collared (as shown here in FIGS. 29 and 30) and non-collared femoral stem implants (as previously shown in FIGS. 24-28).

Figures 31, 32, 33, 34, 35, 36, 37, 38:
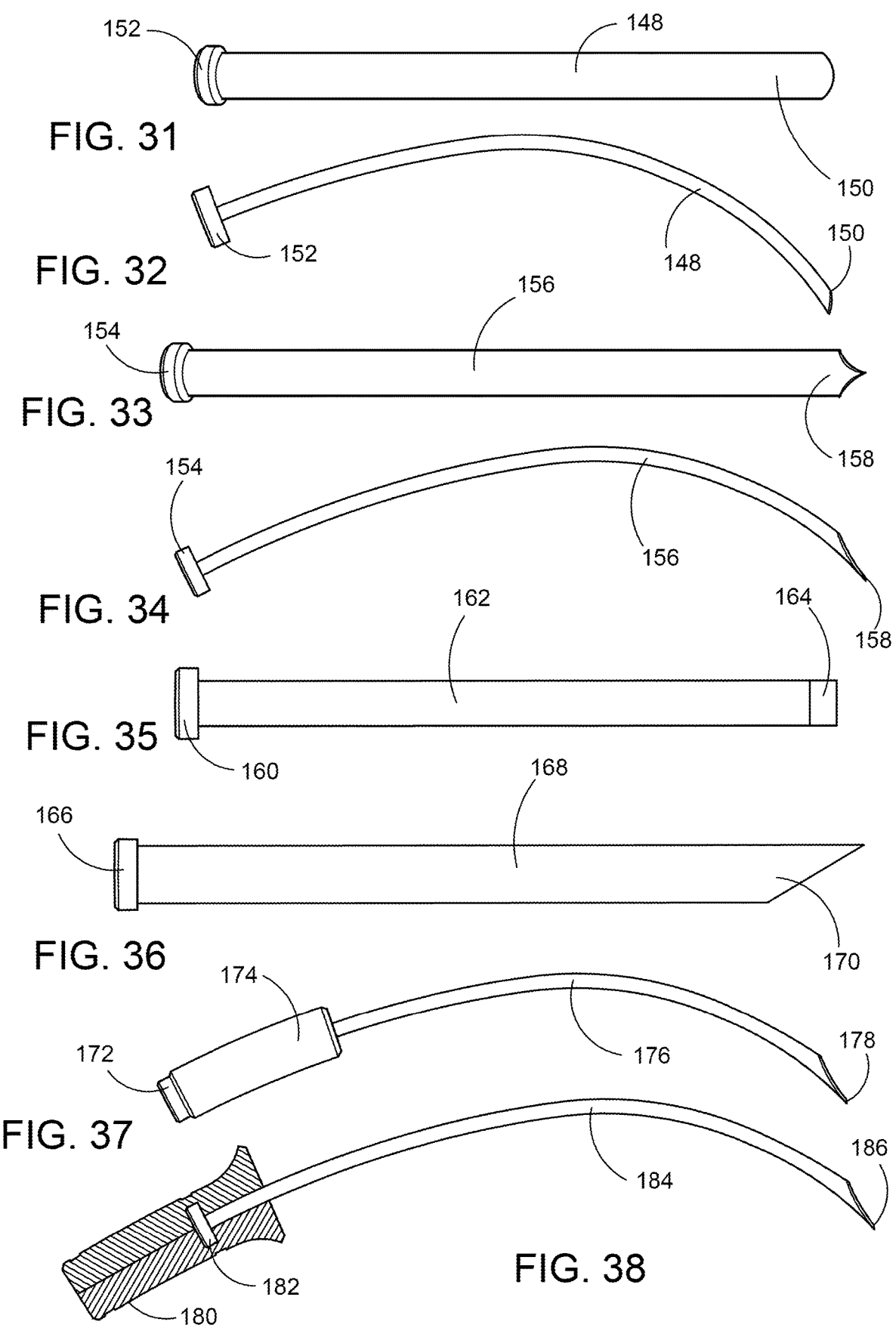
FIG. 31 depicts a top view of a heavy curved blade a curved sharp end and a metal end cap.
FIG. 32 depicts a side view of a heavy curved blade a curved sharp end and a metal end cap.
FIG. 33 depicts a top view of a thin curved blade a curved sharp end and a metal end cap.
FIG. 34 depicts a side view of a thin curved blade a curved sharp pointed end and a metal end cap.
FIG. 35 depicts a top view of a straight narrow flat blade with a chisel shaped sharp end and a metal end cap.
FIG. 36 depicts a top view of a straight wide flat blade with a triangular shaped sharp end and a metal end cap.
FIG. 37 depicts a side view of a thin curved blade a sharp pointed end, a straight handle and a metal end cap.
FIG. 38 depicts a side view of a thin curved blade a sharp pointed end, a two part handle with the metal end cap enclosed.

FIG. 31 depicts a top view of a heavy compound curved prosthesis blade 148 with a curved sharp end 150 and a metal end cap 152.

FIG. 32 depicts a side view of a heavy compound curved prosthesis blade 148, shown in FIG. 31 having a curved sharp end 150 and a metal end cap 152.

FIG. 33 depicts a top view of a thin compound curved prosthesis blade 156 with a curved sharp pointed end 158 and a metal end cap 154.

FIG. 34 depicts a side view of a thin compound curved prosthesis blade 156, shown in FIG. 33 having a with a curved sharp pointed end 158 and a metal end cap 154.

FIG. 35 depicts a top view of a straight narrow flat blade 162 with a chisel shaped sharp end 164 and a metal end cap 160.

FIG. 36 depicts a top view of a straight wide flat blade 168 with a triangular shaped sharp end 170 and a metal end cap 166.

FIG. 37 depicts a side view of a thin compound curved prosthesis blade 176 with a straight handle 174 and a metal end cap 172, having a compound curved pointed cutting edge 178.

FIG. 38 depicts side view of a thin compound curved prosthesis blade 184 with a two-part handle 180 and the metal end cap 182 here is enclosed within two-part handle 180. This thin compound curved prosthesis blade 184 has a compound curved pointed cutting edge 186.

Figures 39, 40, 41, 42, 43:
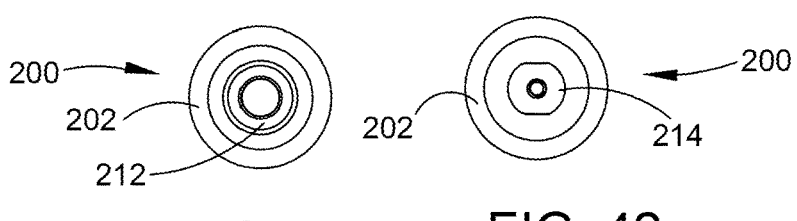
FIG. 39 depicts a top, side elevational and perspective view of a surgical slide hammer attachable to the assembled surgical osteotome blade guide block.
FIG. 40 depicts a top plan view of a surgical slide hammer attachable to the assembled surgical osteotome blade/surgical chisel guide block.
FIG. 41 depicts a side elevational view of a surgical slide hammer attachable to the assembled surgical osteotome blade/surgical chisel guide block.
FIG. 42 depicts a bottom view of a surgical slide hammer attachable to the assembled surgical osteotome blade/surgical chisel guide block.
FIG. 43 depicts a rotated side elevational view, rotated 90 degrees of a surgical slide hammer attachable to the assembled surgical osteotome blade/surgical chisel guide block, as shown in FIG. 41.

FIG. 39 depicts a top, side elevational and perspective view of a surgical slide hammer assembly 200 attachable to the assembled surgical osteotome blade guide block (not shown). The slide hammer assembly 200 comprises a slide hammer handle 202 having a slide hammer handle upper surface 204 and a slide hammer handle lower surface 206. The slide hammer handle 202 moves up and down on a handle shaft having a slide hammer handle shaft lower section 208 and a slide hammer handle shaft upper section 210. At the end of the slide hammer handle shaft lower section 208 there is a threaded attachment member nut 214 and this threaded attachment member nut 214 is wider in diameter than the slide hammer handle lower section 208. Likewise, at the top of the slide hammer handle shaft upper section 210 there is a slide hammer impact cap 212. This slide hammer impact cap 212 is also wider in diameter than the slide hammer handle shaft upper section 210.

FIG. 40 depicts a top plan view of a surgical slide hammer assembly 200 attachable to the assembled surgical osteotome blade guide block (not shown). In this top plan view of the slide hammer assembly 200, there is seen the slide hammer handle 202 and the slide hammer impact cap 212.

FIG. 41 depicts a side elevational view of a surgical slide hammer assembly 200 attachable to the assembled surgical osteotome blade guide block (not shown). In this side elevational view of the slide hammer assembly 200, there is seen the slide hammer handle 202 and the slide hammer threaded attachment member nut 214.

FIG. 42 depicts a bottom view of a surgical slide hammer assembly 200 attachable to the assembled surgical osteotome blade guide block (not shown). The slide hammer assembly 200 comprises a slide hammer handle 202 having a slide hammer handle upper surface 204 and a slide hammer handle lower surface 206. The slide hammer handle 202 moves up and down on a handle shaft having a slide hammer handle shaft lower section 208 and a slide hammer handle shaft upper section 210. At the end of the slide hammer handle shaft lower section 208 there is a threaded attachment member nut 214 and this threaded attachment member nut 214 is wider in diameter than the slide hammer handle lower section 208. Likewise, at the top of the slide hammer handle shaft upper section 210 there is a slide hammer impact cap 212. This slide hammer impact cap 212 is also wider in diameter than the slide hammer handle shaft upper section 210.

FIG. 43 depicts a rotated side elevational view, rotated 90 degrees of a surgical slide hammer assembly 200 attachable to the assembled surgical osteotome blade guide block, as shown in FIG. 41. Again, the slide hammer assembly 200 comprises a slide hammer handle 202 having a slide hammer handle upper surface 204 and a slide hammer handle lower surface 206. The slide hammer handle 202 moves up and down on a handle shaft having a slide hammer handle shaft lower section 208 and a slide hammer handle shaft upper section 210. At the end of the slide hammer handle shaft lower section 208 there is a threaded attachment member nut 214 and this threaded attachment member nut 214 is wider in diameter than the slide hammer handle lower section 208. Likewise, at the top of the slide hammer handle shaft upper section 210 there is a slide hammer impact cap 212. This slide hammer impact cap 212 is also wider in diameter than the slide hammer handle shaft upper section 210.

Figure 44:
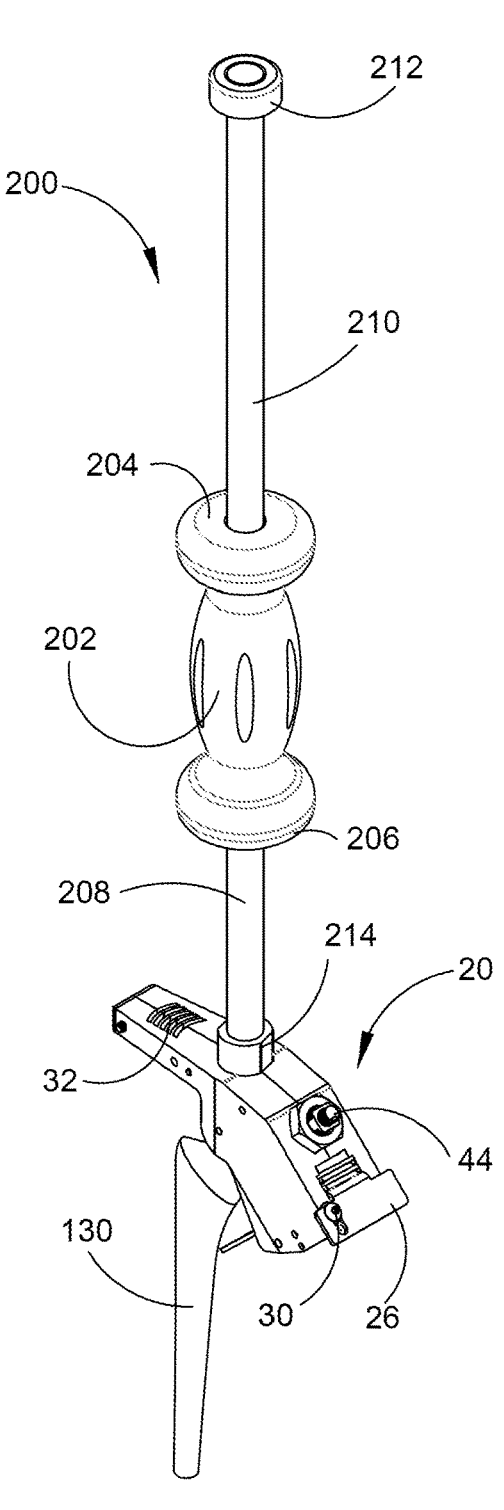
FIG. 44 depicts a top, side elevational and perspective view of a surgical slide hammer attachable to the assembled osteotome blade guide block, here shown in place attached to an assembled surgical osteotome blade guide block.

FIG. 44 depicts a top, side elevational and perspective view of a surgical slide hammer assembly 200 attachable to the assembled osteotome blade guide block, here shown in place attached to an assembled surgical osteotome blade guide block 20. The male threaded attachment member nut 214 is threaded into the female threaded orifice 34 located on the top surface of the assembled surgical osteotome blade guide block 20 (see FIG. 47).

Figure 45:
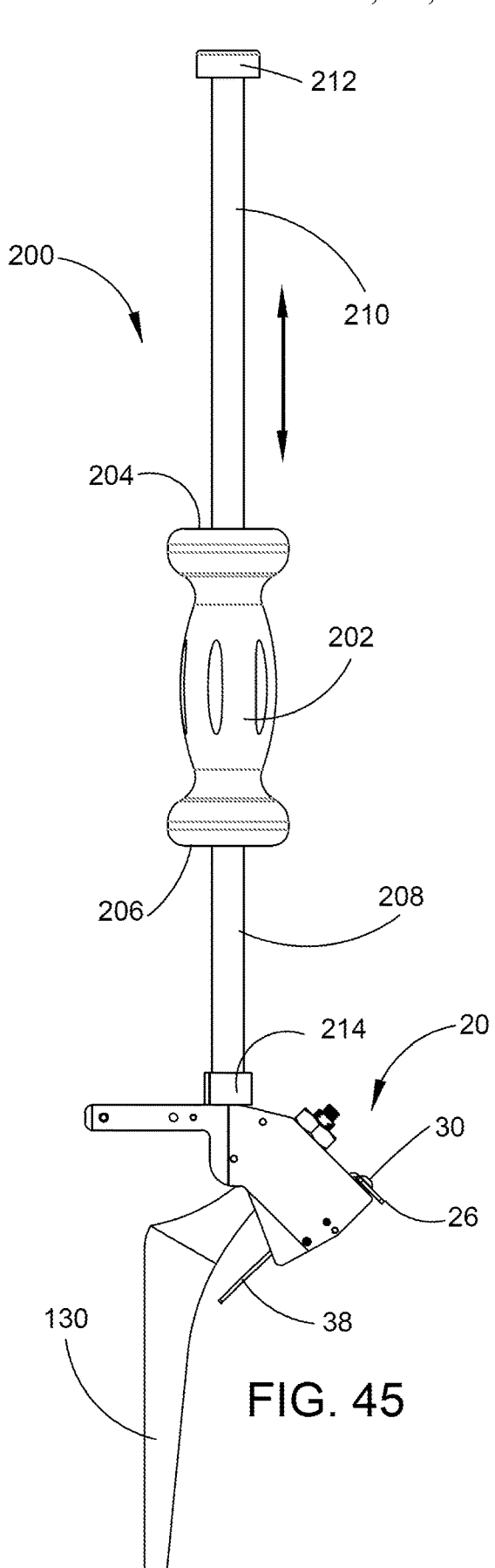
FIG. 45 depicts a side elevational view of a surgical slide hammer attachable to the assembled osteotome blade guide block, here shown in place attached to an assembled surgical osteotome blade guide block.

FIG. 45 depicts a side elevational view of a surgical slide hammer assembly 200 attachable to the assembled osteotome blade guide block, here shown in place attached to an assembled surgical osteotome blade guide block 20. The male threaded attachment member nut 214 is threaded into the female threaded orifice 34 located on the top surface of the assembled surgical osteotome blade guide block 20. In operation, the male threaded attachment member 214 is threaded into the guide block 20 female threaded orifice 34, then the handle is moved upwardly (see motion arrow) striking the slide hammer impact cap 212 to extract the implant 130 attached to the guide block assembly 20.

Figure 46:
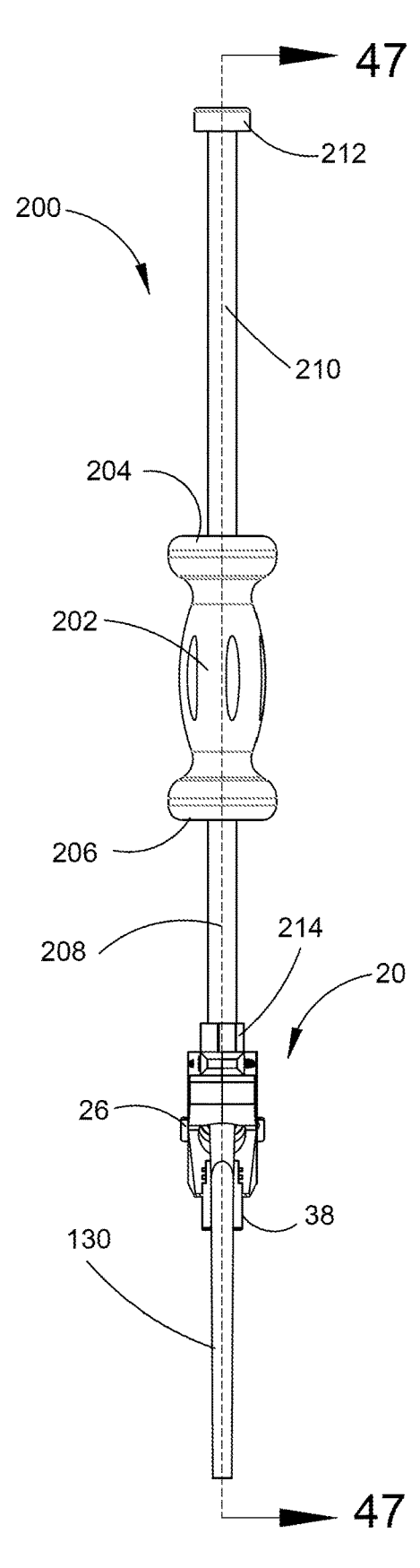
FIG. 46 depicts a rear view of a surgical slide hammer attachable to the assembled osteotome blade guide block, here shown in place attached to an assembled surgical osteotome blade guide block.

FIG. 46 depicts a rear view of a surgical slide hammer assembly 200 attachable to the assembled osteotome blade guide block, here shown in place attached to an assembled surgical osteotome blade guide block 20. The male threaded attachment member nut 214 is threaded into the female threaded orifice 34 located on the top surface of the assembled surgical osteotome blade guide block 20. In operation, the male threaded attachment member 214 is threaded into the guide block 20 female threaded orifice 34, then the handle is moved upwardly striking the slide hammer impact cap 212 to extract the implant 130 attached to the guide block assembly 20.

Figure 47:
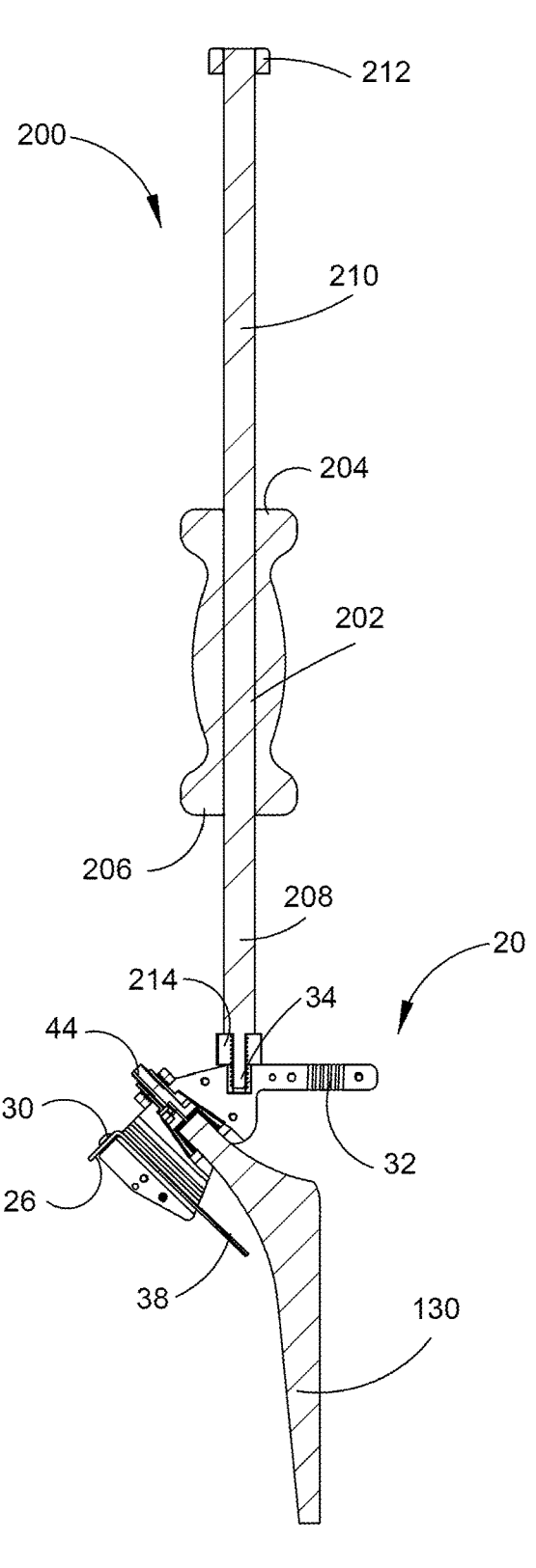
FIG. 47 depicts a cross-sectional view of the surgical slide hammer attachable to the assembled osteotome blade guide block, here shown in place attached to an assembled surgical osteotome blade guide block of FIG. 46.

FIG. 47 depicts a cross-sectional view of the surgical slide hammer assembly 200 attachable to the assembled osteotome blade guide block 20, here shown in place attached to an assembled surgical osteotome blade guide block 20 of FIG. 46. In this cross-sectional view, it is clearly shown that the male threaded attachment member nut 214 is threaded into the female threaded orifice 34 located on the top surface of the assembled surgical osteotome blade guide block 20. Once attached, the slide hammer handle 202 slides upward to impact the end cap 212 and the momentum pulls the guide block 20 and stem trunnion securing member 44 affixed to the implant 130 up and out of the femur during revision surgery.

Figure 48:
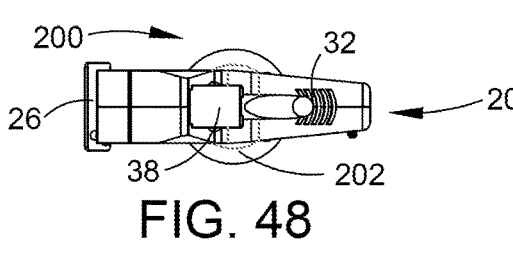
FIG. 48 depicts a bottom view of the surgical slide hammer attachable to the assembled osteotome blade guide block, here shown in place attached to an assembled surgical osteotome blade guide block.

FIG. 48 depicts a bottom view of the surgical slide hammer assembly 200 attachable to the assembled osteotome blade guide block 20, here shown in place attached to an assembled surgical osteotome blade guide block 20. This bottom view shows the slide hammer handle 202 and more detail of the guide block 20 with guide plate upper section 26 and guide plate lower section 38 as well as the rearward guide slots 32.

Figure 49:
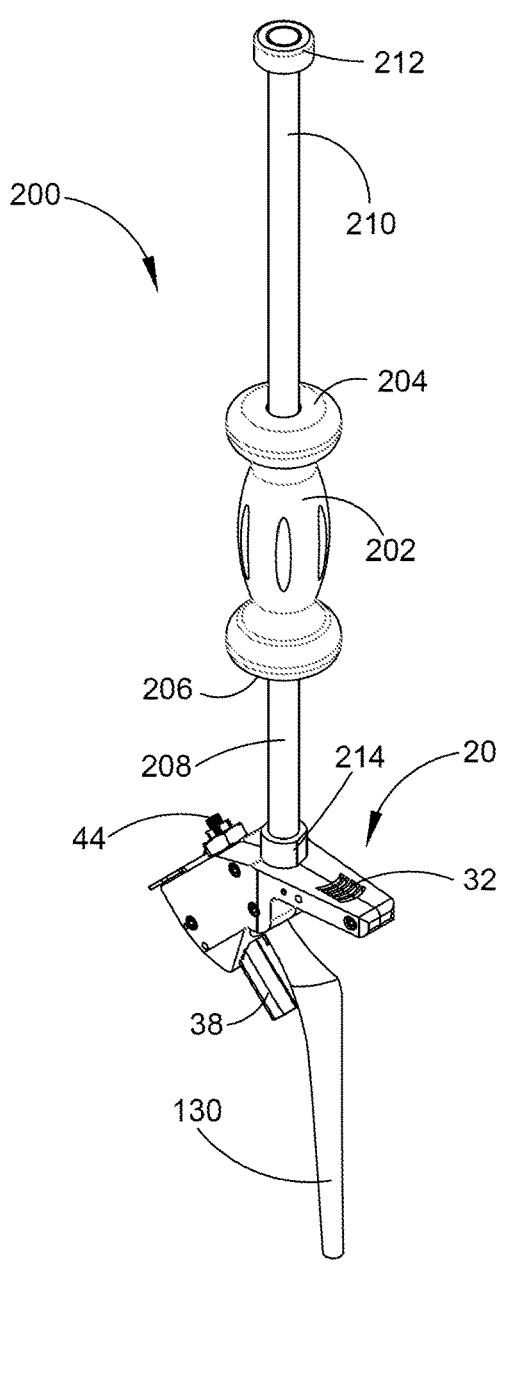
FIG. 49 depicts a top, side elevational and perspective view of a surgical slide hammer attachable to the assembled osteotome blade guide block, here shown in place attached to an assembled surgical osteotome blade guide block.

FIG. 49 depicts a top, side elevational and perspective view of a surgical slide hammer assembly 200 attachable to the assembled osteotome blade guide block 20, here shown in place attached to an assembled surgical osteotome blade guide block 20. This view more clearly shows the slide hammer handle 202 and impact end cap 212, as well as greater detail of the guide block 20 showing the attached slide hammer threaded nut 214 and the trunnion securing member 44 as well as guide plate lower section 38.

Figure 50:
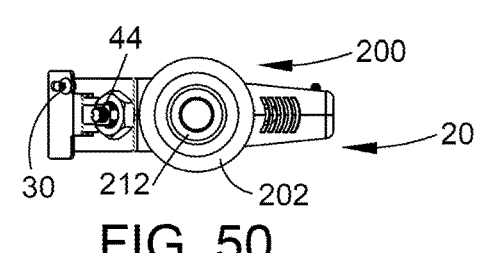
FIG. 50 depicts a top plan view of the surgical slide hammer attachable to the assembled osteotome blade guide block, here shown in place attached to an assembled surgical osteotome blade guide block.

FIG. 50 depicts a top plan view of the surgical slide hammer assembly 200 attachable to the assembled osteotome blade guide block 20, here shown in place attached to an assembled surgical osteotome blade guide block 20. This top plan view more clearly shows the slide hammer handle 202 and impact end cap 212, as well as greater detail of the guide block 20 showing the adjustment screw 30, and the trunnion securing member 44.

Figure 51:
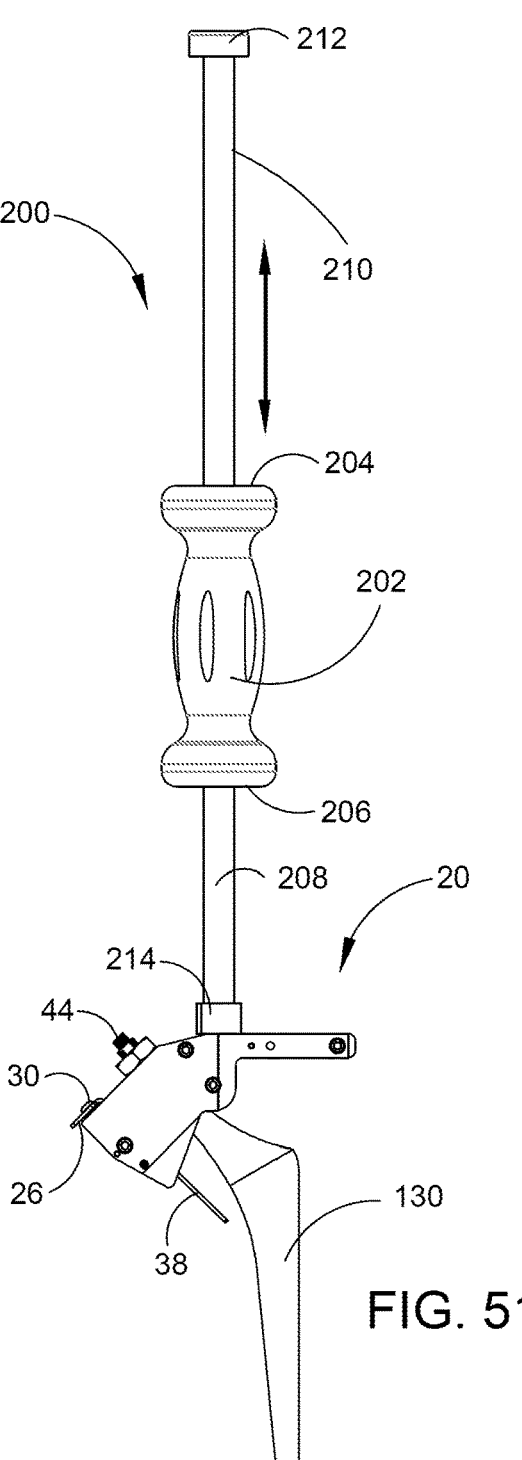
FIG. 51 depicts a side elevational view of the surgical slide hammer attachable to the assembled osteotome blade guide block, here shown in place attached to an assembled surgical osteotome blade guide block.

FIG. 51 depicts a side elevational view of the surgical slide hammer assembly 200 attachable to the assembled osteotome blade guide block 20, here shown in place attached to an assembled surgical osteotome blade guide block 20. This view more clearly shows the slide hammer handle 202 and impact end cap 212, as well as greater detail of the guide block 20 showing the attached slide hammer threaded nut 214 and the trunnion securing member 44 as well as guide plate lower section 38. In operation, the male threaded attachment member 214 is threaded into the guide block 20 female threaded orifice 34, then the handle is moved upwardly (see motion arrow) striking the slide hammer impact cap 212 to extract the implant 130 attached to the guide block assembly 20. Therefore, once attached, the slide hammer handle 202 slides upward to impact the end cap 212 and the momentum pulls the guide block 20 and stem trunnion securing member 44 affixed to the implant 130 up and out of the femur during revision surgery.

Figures 52, 53:
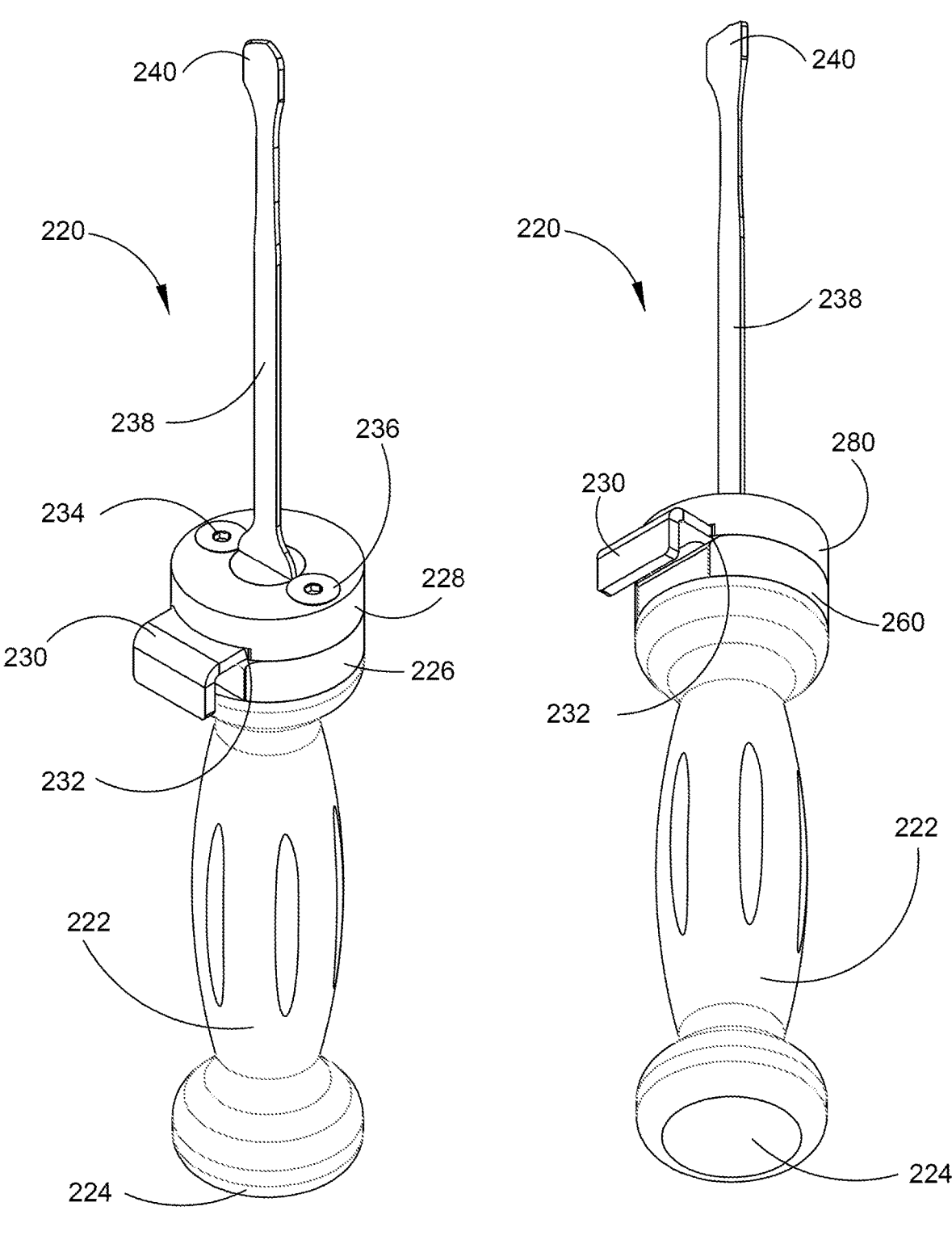
FIG. 52 depicts a top, side elevational and perspective view of a surgical blade locking osteotome handle assembly having a surgical osteotome blade inserted therein and showing the locking lever in the outward locked position which secures the surgical osteotome blade therein.
FIG. 53 depicts a bottom, side elevational and perspective view of a surgical blade locking osteotome handle assembly having a surgical osteotome blade inserted therein and showing the locking lever in the outward locked position which secures the surgical osteotome blade therein.

FIG. 52 depicts a top, side elevational and perspective view of a surgical blade locking osteotome handle assembly 220 having a surgical osteotome blade 238 inserted therein, and showing the locking lever 230 in the outward locked or open position which secures the surgical osteotome blade therein in the open position. The surgical blade locking osteotome handle assembly 220 comprises a handle 222 having an impact lower end 224 and a two-part locking chamber consisting of lower locking chamber 226 and upper locking chamber 228. The locking chamber houses a locking lever 230 which is inserted into locking lever slot 232. The locking chamber sections 226 and 228 are retained to the handle using two retaining screws 234 and 236. In this FIG. 52, the osteotome blade 238 having a cutting edge 240 is inserted into the locking handle assembly 220 and the locking lever 230 is in the outward locked position which secures the surgical osteotome blade therein in the open position. To unlock the osteotome blade 238 in the locking chamber 226 and 228 the locking lever 230 would be pushed inward in the closed or unlocked position, allowing the osteotome blade 238 to be inserted or removed (see FIGS. 54-58).

FIG. 53 depicts a bottom, side elevational and perspective view of a surgical blade locking osteotome handle assembly 220 having a surgical osteotome blade 238 inserted therein, and showing the locking lever 230 in the outward locked or open position which secures the surgical osteotome blade therein in the open position. The surgical blade locking osteotome handle assembly 220 comprises a handle 222 having an impact lower end 224 and a two-part locking chamber consisting of lower locking chamber 226 and upper locking chamber 228. The locking chamber houses a locking lever 230 which is inserted into locking lever slot 232. The locking chamber sections 226 and 228 are retained to the handle using two retaining screws 234 and 236. In this FIG. 53, the osteotome blade 238 having a cutting edge 240 is inserted into the locking handle assembly 220 and the locking lever 230 is in the outward open or locked position, allowing the osteotome blade 238 to be secured within the handle. To unlock the osteotome blade 238 in the locking chamber 226 and 228 the locking lever 230 would be pushed inward which would release the surgical osteotome blade (see FIGS. 54-58). In this way, various surgical osteotome blades are readily removed and replaced within the handle 220, then locked into place for various surgical procedures.

Figure 54:
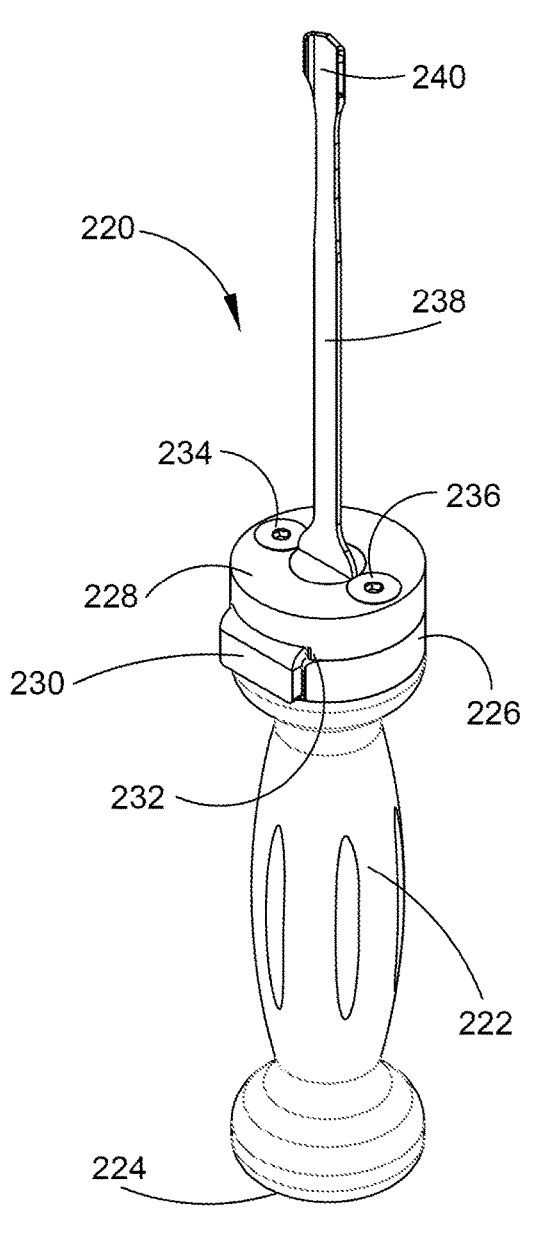
FIG. 54 depicts a top, side elevational and perspective view of a surgical blade locking osteotome handle assembly having a surgical osteotome blade inserted therein and showing the locking lever in the inward unlocked position which enables the surgical osteotome blade to be inserted and removed.

FIG. 54 depicts a top, side elevational and perspective view of a surgical blade locking osteotome handle assembly 220 having a surgical osteotome blade 238 inserted therein, and showing the locking lever 230 in the inward pushed in unlocked position, which would allow for insertion and removal of a surgical osteotome blade. Here, as shown, the locking lever 230 has been pushed into the locking lever slot 232. In this way, the osteotome blade 238 is unlocked within the handle 222 for subsequent insertion and removal for use in surgical procedures as required.

Figure 55:
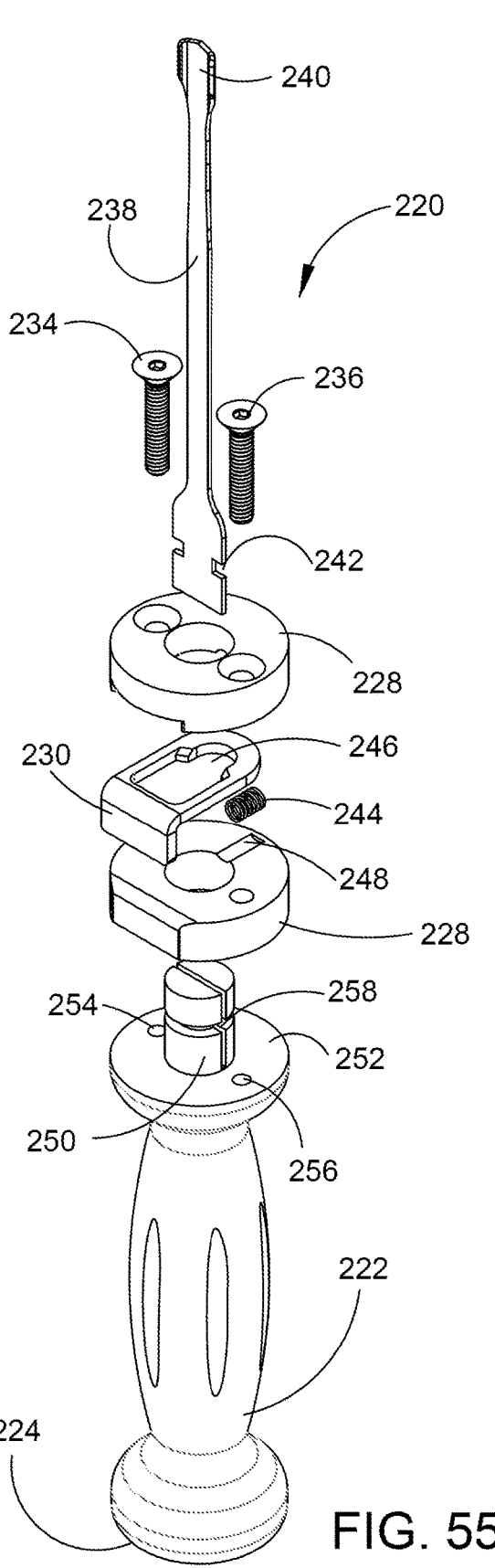
FIG. 55 depicts a top, side elevational and perspective exploded view of a surgical blade locking osteotome handle assembly having a surgical osteotome blade inserted therein and showing the locking lever in the inward unlocked position which enables the surgical osteotome blade to be inserted and removed.

FIG. 55 depicts a top, side elevational and perspective exploded view of a surgical blade locking osteotome handle assembly 220 having a surgical osteotome blade 238 inserted therein and showing the locking lever 230 in the inward pushed in unlocked position, which would allow for insertion and removal of a surgical osteotome blade. This exploded view illustrates the inner workings detail of the locking handle 220. The two locking chamber parts 226 and 228 house the locking lever 230 and a locking lever spring 244 located in a locking lever spring groove 248 machined within and integral to the lower chamber half 228. Locking lever 230 includes a frame defining a central opening which presses against locking lever spring 244 when assembled. Handle 222 has an upper surface 252, a mounting post 250 and retaining screw orifices 254 and 256. The mounting post includes grooves 258 which allow the osteotome blade to be inserted and locked into place by the locking lever 230 when the locking lever 230 is in the outward opened position (all the way out). In operation, the osteotome blade 238 includes locking slots 242 which are securely locked into place by locking lever 230 when locking lever 230 is in the outward position or all the way out of the locking slot 232 formed by the two-part locking chamber 226 and 228. The locking lever 230 is under pressure by the locking lever spring 244 and remains in the outward locking position due to that pressure exerted by the locking lever spring 244 when in use by a surgeon.

Figures 56, 57, 58:
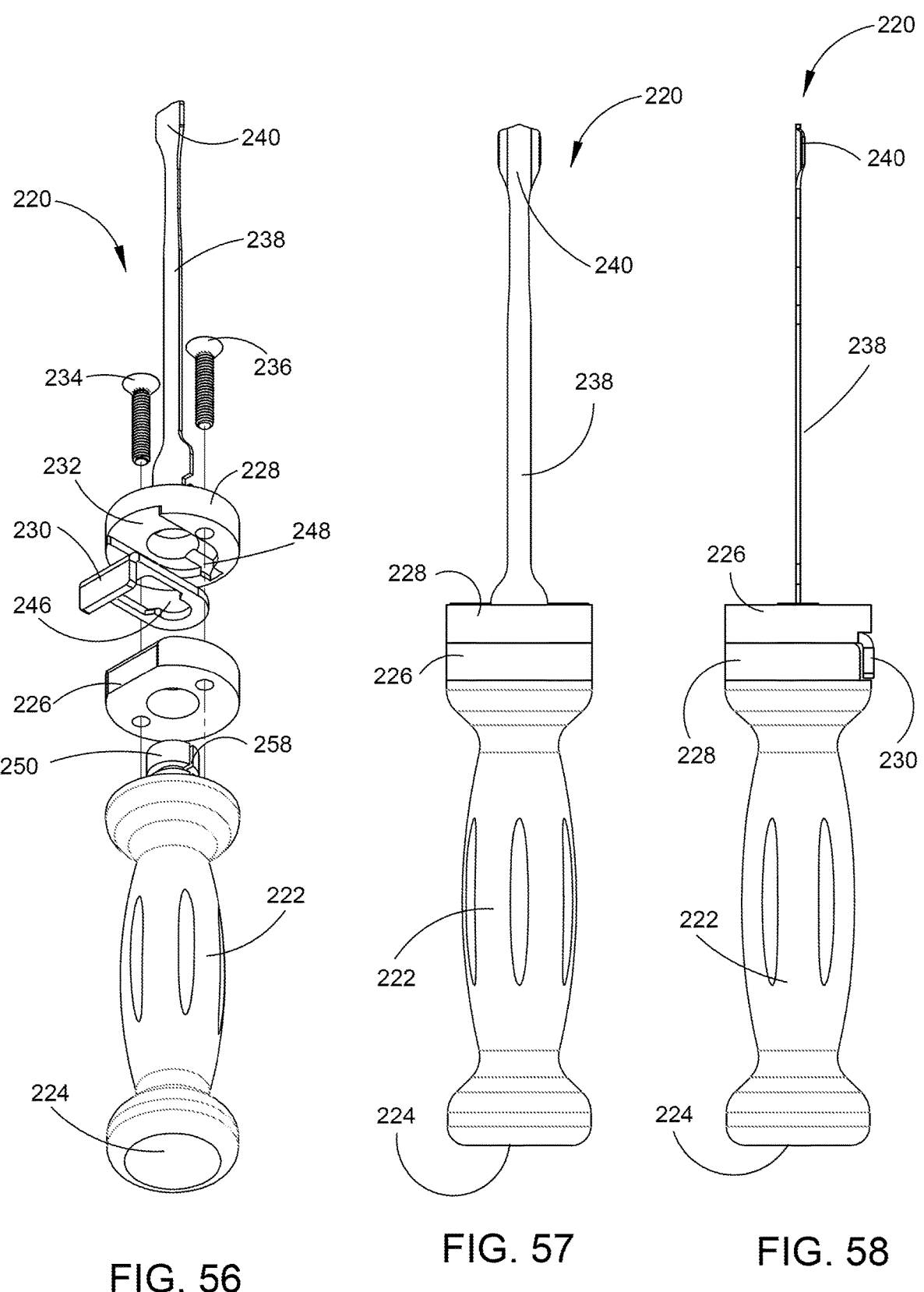
FIG. 56 depicts a bottom, side elevational and perspective exploded view of a surgical blade locking osteotome handle assembly having a surgical osteotome blade inserted therein and showing the locking lever in the inward unlocked position which enables the surgical osteotome blade to be inserted and removed.
FIG. 57 depicts a front view of a surgical blade locking osteotome handle assembly having a surgical osteotome blade inserted therein.
FIG. 58 depicts a side elevational view of a surgical blade locking osteotome handle assembly having a surgical osteotome blade inserted therein and showing the locking lever in the inward unlocked position which enables the surgical osteotome blade to be inserted and removed.

FIG. 56 depicts a bottom, side elevational and perspective exploded view of a surgical blade locking osteotome handle assembly having a surgical osteotome blade inserted therein and showing the locking lever 230 in the inward pushed in unlocked position, which would allow for insertion and removal of a surgical osteotome blade. Again, this exploded view illustrates the inner workings detail of the locking handle 220. The two locking chamber parts 226 and 228 house the locking lever 230 and a locking lever spring 244 located in a locking lever spring groove 248 machined within and integral to the lower chamber half 228. Locking lever 230 includes a frame defining a central opening which presses against locking lever spring 244 when assembled. Handle 222 has an upper surface 252, a mounting post 250 and retaining screw orifices 254 and 256. The mounting post includes grooves 258 which allow the osteotome blade to be inserted and locked into place by the locking lever 230 when the locking lever 230 is in the outward opened position (all the way out). In operation, the osteotome blade 238 includes locking slots 242 which are securely locked into place by locking lever 230 when locking lever 230 is in the outward position or all the way out of the locking slot 232 formed by the two-part locking chamber 226 and 228. The locking lever 230 is under pressure by the locking lever spring 244 and remains in the outward locking position due to that pressure exerted by the locking lever spring 244 when in use by a surgeon.

FIG. 57 depicts a front view of a surgical blade locking osteotome handle assembly 220 having a surgical osteotome blade 238 inserted therein and showing the locking lever (not seen in this view) in the inward pushed in or unlocked position (not shown), which would allow for insertion and removal of a surgical osteotome blade.

FIG. 58 depicts a side elevational view of a surgical blade locking osteotome handle assembly 220 having a surgical osteotome blade 238 inserted therein and showing the locking lever 230 in the inward pushed in unlocked position, which would allow for insertion and removal of a surgical osteotome blade. In operation, the locking lever 230 would be pushed in, the blade removed and or inserted, then the locking lever spring 244 pressure would allow for the locking lever 230 to return automatically to the locked or outward position. In this way, the osteotome blade 238 is locked within the handle 222 in its normal locked configuration (the locking lever is all the way out), then the locking lever 230 is pushed inward to unlock the surgical blades for subsequent insertion and removal for use in surgical procedures as required. Therefore, surgical osteotome blades are readily removed and replaced using the surgical blade locking osteotome handle assembly 220 as required by the stage or need of the surgeon during surgical procedures.

Figures 59, 60, 61, 62:
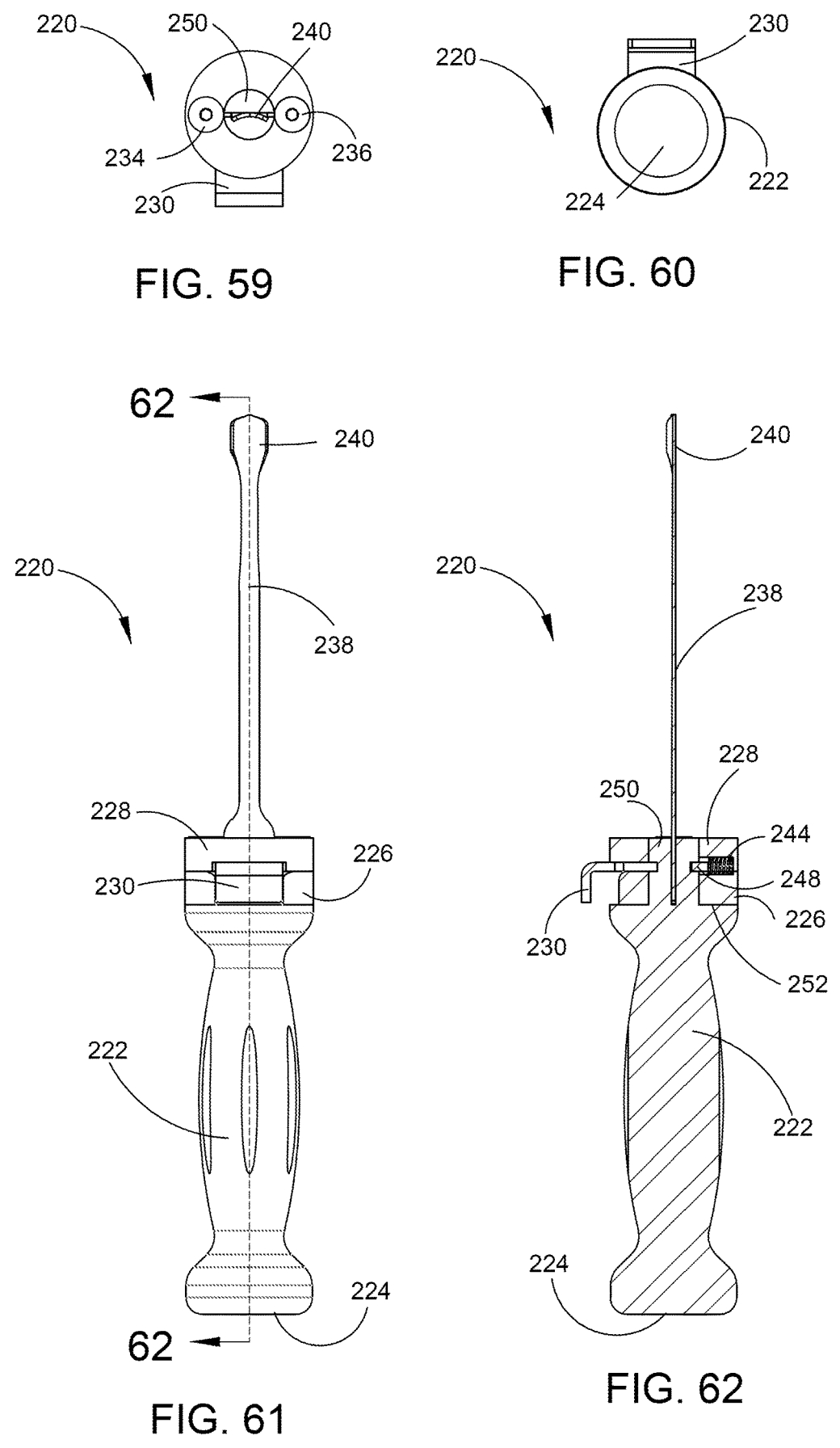

FIG. 59 depicts a top plan view of a surgical blade locking osteotome handle assembly 220 having a surgical osteotome blade 240 inserted therein and illustrating the locking lever 230 in the open or locked position. In this view, the retaining screws 234 and 236, as well as the mounting post 250 and the open positioned locking lever 230 are clearly shown.

FIG. 60 depicts a bottom view of a surgical blade locking osteotome handle assembly 220 having a surgical osteotome blade (not seen here) inserted therein. In this view the handle 222 impact base 224 is clearly shown. In operation, the handle 222 can be used to insert a surgical osteotome blade to cut bone, and when the bone is difficult to cut, then the impact end 224 can be manually hammered, either by hand or by the use of a surgical hammer, to allow the surgeon to cut bone more readily and quickly.

FIG. 61 depicts a front view of a surgical blade locking osteotome handle assembly 220 having a surgical osteotome blade 238 inserted therein.

FIG. 62 depicts a cross-sectional view of the surgical blade locking osteotome handle assembly 220 having a surgical osteotome blade 238 inserted therein, as shown in FIG. 61. In this cross-sectional view the mounting post 250 is seen having the lower locking chamber half 226 and the upper locking chamber half 228 assembled thereon. The two halves 226 and 228 define a groove in which the locking lever spring 244 is located. The locking lever 230 is shown having the locking lever spring 244 forcing the locking lever in the open or locked position. When the locking lever 230 is open or in the locked position the locking lever 230 locks the blade end into the handle by making contact with the slots within the surgical blade locking plate (described below).

Figure 63:
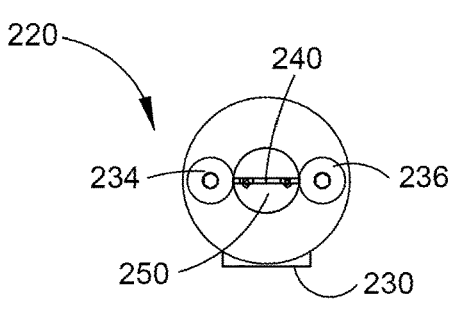
FIG. 63 depicts a top view of a surgical blade locking osteotome handle assembly having a surgical osteotome blade inserted therein and showing the locking lever in the inward unlocked position which enables the surgical osteotome blade to be inserted and removed.

FIG. 63 depicts a top view of a surgical blade locking osteotome handle assembly 220 having a surgical osteotome blade 238 inserted therein and showing the locking lever 230 in the pushed inward or unlocked position. When the locking lever 230 is in this pushed in or unlocked position, surgical osteotome blades 238 are readily inserted and removed. This view is similar to the view in FIG. 59, and it shows like parts as those shown in FIG. 59 (see FIG. 59).

Figure 64:
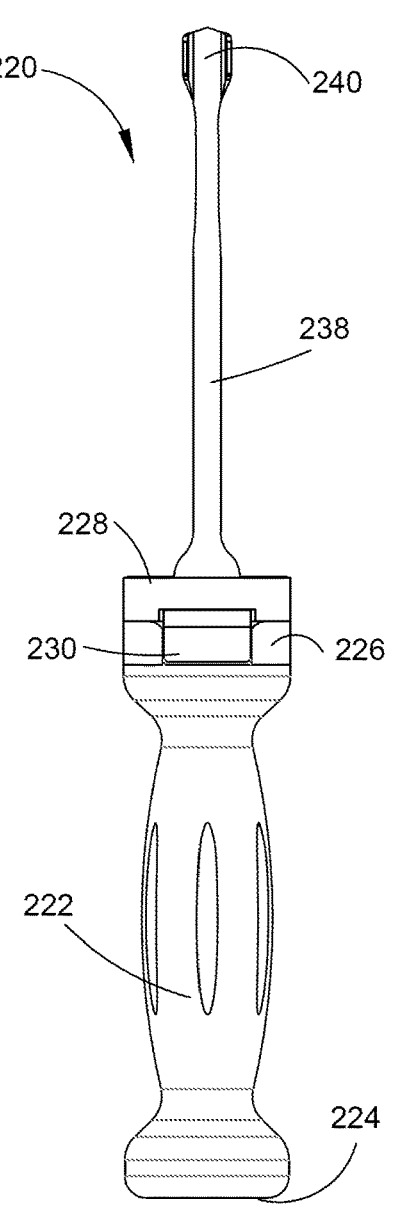
FIG. 64 depicts a front view of a surgical blade locking osteotome handle assembly having a surgical osteotome blade inserted therein and showing the locking lever in the inward unlocked position which enables the surgical osteotome blade to be inserted and removed.

FIG. 64 depicts a front view of a surgical blade locking osteotome handle assembly 220 having a surgical osteotome blade 238 inserted therein and showing the locking lever 230 in the pushed inward or unlocked position. When the locking lever 230 is in this pushed in or unlocked position, surgical osteotome blades 238 are readily inserted and removed. This view is similar to the view in FIG. 61, and it shows like parts as those shown in FIG. 61 (see FIG. 61).

Figure 65:
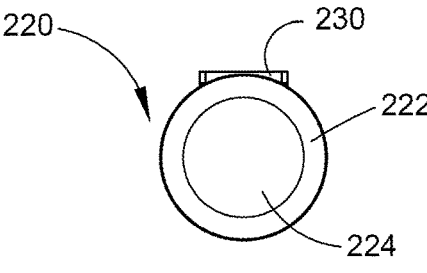
FIG. 65 depicts a bottom view of a surgical blade locking osteotome handle assembly having a surgical osteotome blade inserted therein and showing the locking lever in the closed position.

FIG. 65 depicts a bottom view of a surgical blade locking osteotome handle assembly 220 having a surgical osteotome blade 238 inserted therein and showing the locking lever 230 in the pushed inward or unlocked position. When the locking lever 230 is in this pushed in or unlocked position, surgical osteotome blades 238 are readily inserted and removed. This view is similar to the view in FIG. 60, and it shows like parts as those shown in FIG. 60 (see FIG. 60).

Figure 66:
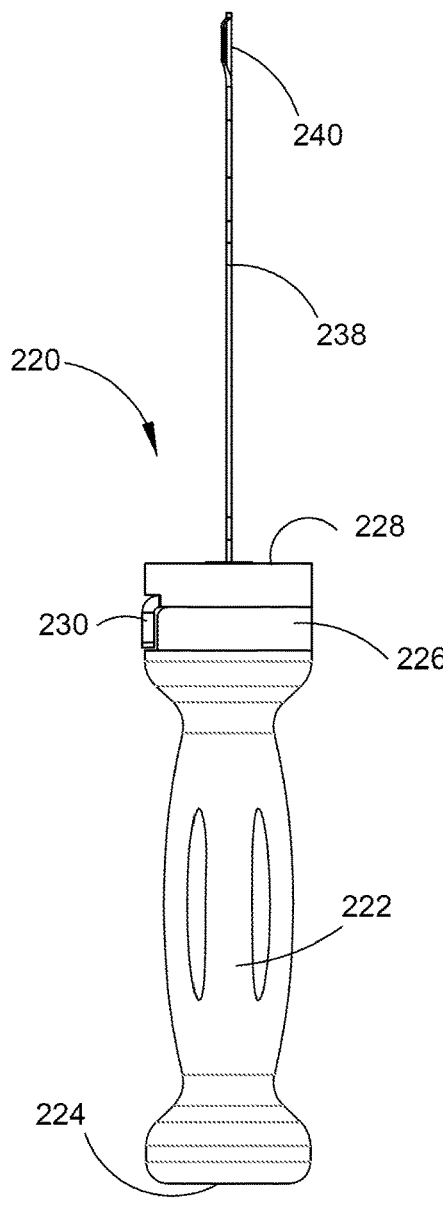
FIG. 66 depicts a side elevational view of a surgical blade locking osteotome handle assembly having a surgical osteotome blade inserted therein and showing the locking lever in the inward unlocked position which enables the surgical osteotome blade to be inserted and removed.

FIG. 66 depicts a side elevational view of a surgical blade locking osteotome handle assembly 220 having a surgical osteotome blade 238 inserted therein and showing the locking lever 230 in the pushed inward or unlocked position. When the locking lever 230 is in this pushed in or unlocked position, surgical osteotome blades 238 are readily inserted and removed. This view is similar, but in an opposite orientation from, the view in FIG. 58, and it shows like parts as those shown in FIG. 58 (see FIG. 58).

Figures 67, 68:
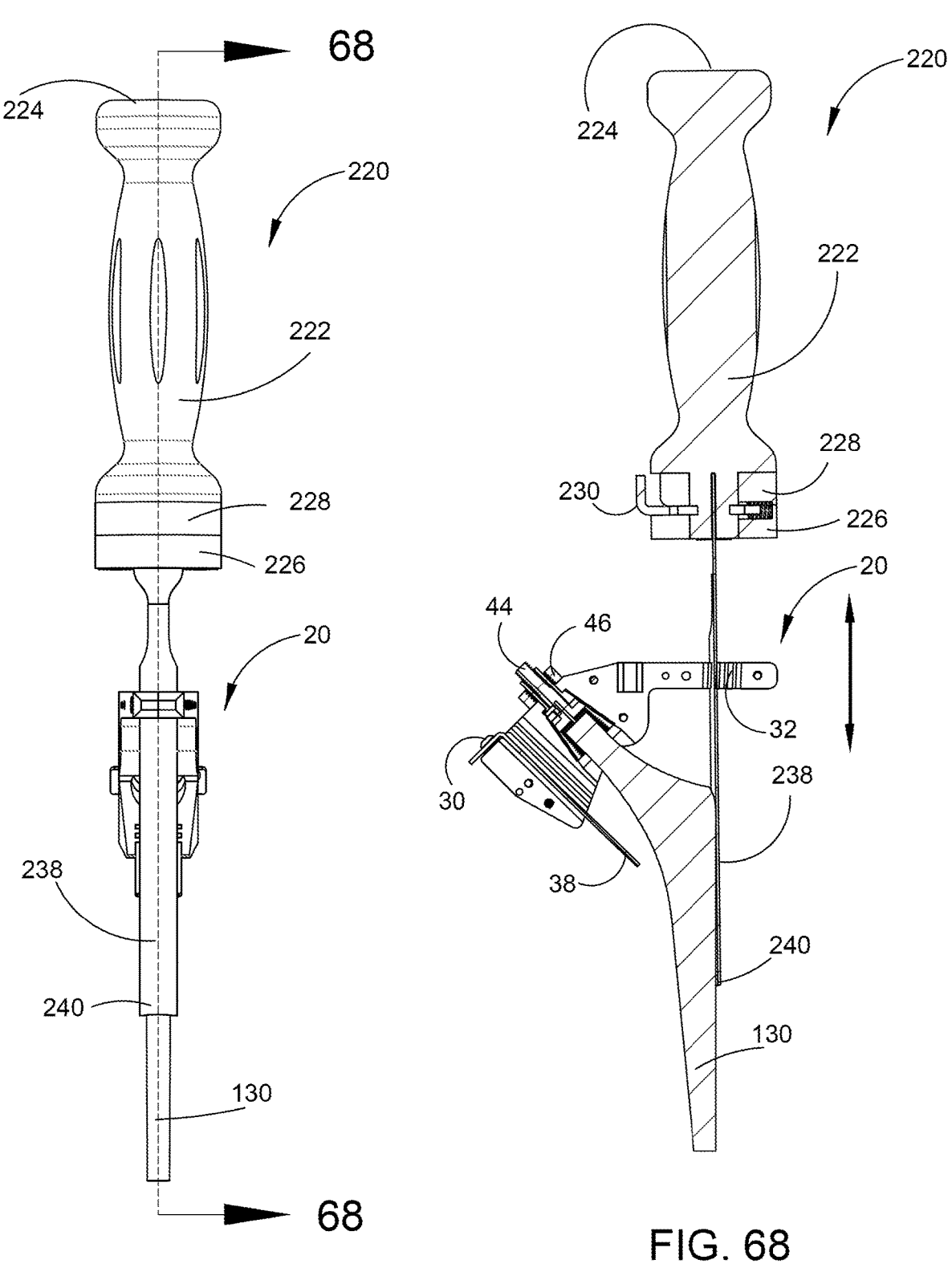
FIG. 67 depicts a cross-sectional side elevational view of a surgical blade locking osteotome handle assembly having a surgical osteotome blade inserted therein, here shown in place attached to a surgical osteotome blade guide block assembly.
FIG. 68 depicts a rear view of a surgical blade locking osteotome handle assembly having a surgical osteotome blade inserted therein, here shown in place attached to a surgical osteotome blade guide block assembly, as shown in FIG. 67.

FIG. 67 depicts a rear view of a surgical blade locking osteotome handle assembly 220 having a surgical osteotome blade 238 inserted therein, here shown in place attached to a surgical osteotome blade guide block assembly 20. In this view, the surgical osteotome blade guide block assembly 20 is attached to an implant 130 and is being used to guide the osteotome blade 238 down through the guide block rearward guide slots (see greater detail of this in FIG. 68) in order to cut the shoulder section of implant 130 away from the bone (not shown).

FIG. 68 depicts a cross-sectional side elevational view of a surgical blade locking osteotome handle assembly 220 having a surgical osteotome blade 238 inserted therein, here shown in place attached to a surgical osteotome blade guide block assembly 20, as shown in FIG. 67. Recall that surgical osteotome blade guide block assembly 20 comprises a lower guide plate 38, a guide plate adjustment screw 30 and a trunnion securing member 44 securely held to the surgical osteotome blade guide block assembly 20 by nut 46. The plurality of rearward guide slots 32 are also clearly seen here. Based on the size of the implant 130, the surgeon chooses a single slot within the plurality of rearward guide slots 32 to extend the blade 238 downwardly, which blade 238 has been secured to the handle 222 with locking lever 230 in the outward or locked position. In this way, the lateral shoulder of the implant 130 is cut away from the bone (not shown) to be released in a revision surgery procedure. The combination of using the osteotome blade 238 secured within the handle assembly 220 and extending the blade 238 downwardly through the guide slot to cut the lateral shoulder of the implant 130 makes for a very efficient and time saving revision surgery resulting in significantly improved patient outcomes.

Figures 69, 70, 71:
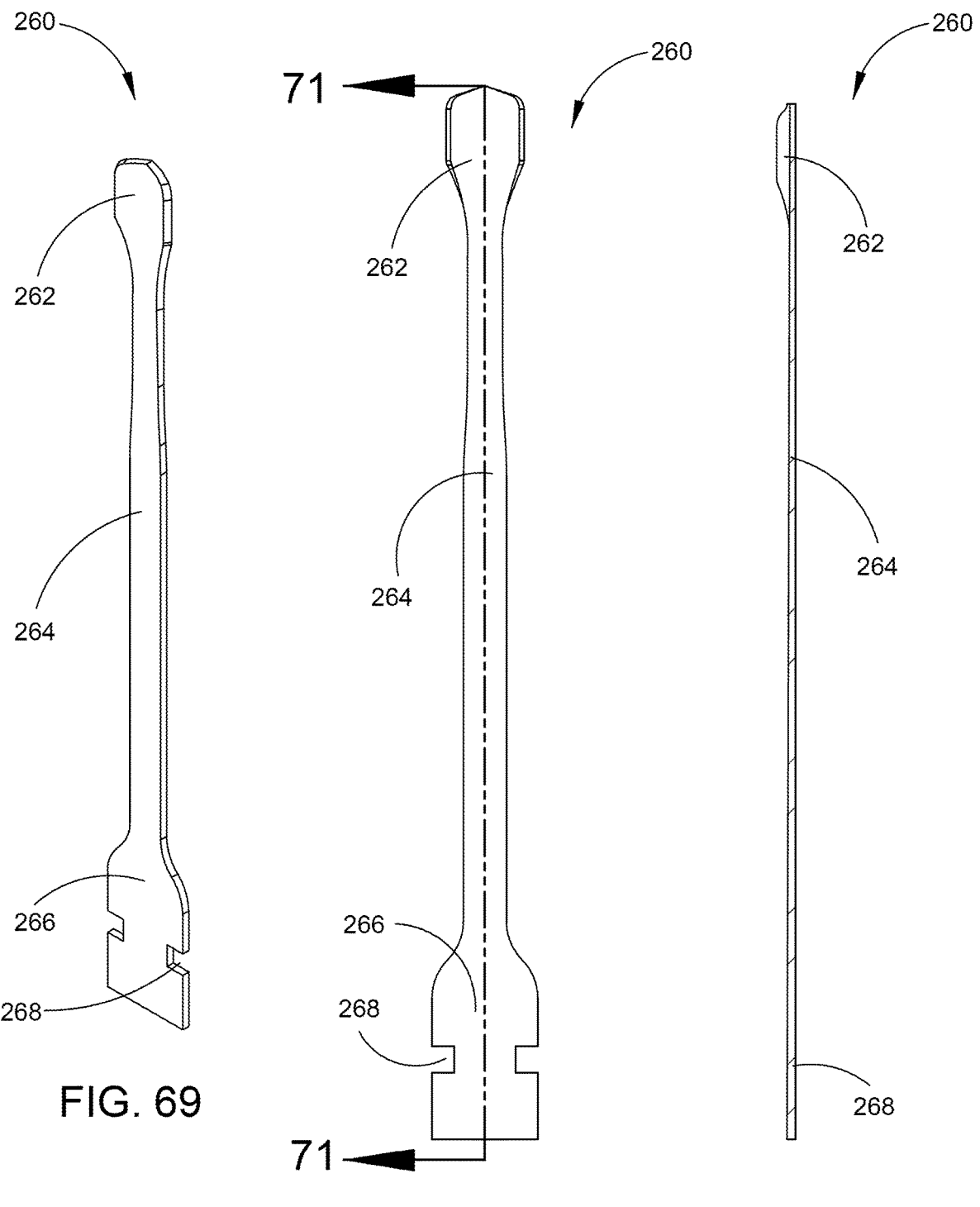
FIG. 69 depicts a top, side elevational and perspective view of a flexible medial calcar osteotome blade having a spoon-shaped cutting edge.
FIG. 70 depicts a front view of a flexible medial calcar osteotome blade having a spoon-shaped cutting edge.
FIG. 71 depicts a cross-sectional view of the flexible medial calcar osteotome blade having a spoon-shaped cutting edge, shown in FIG. 70.

FIG. 69 depicts a top, side elevational and perspective view of a flexible medial calcar osteotome blade 260 having a spoon-shaped cutting edge 262. The flexible medial calcar osteotome blade 260 having a spoon-shaped cutting edge 262 also includes the following features: a blade shaft 264 and a blade insertion plate 266 distal to the spoon-shaped cutting edge 262. The blade insertion plate 266 defines one or more blade locking slots 268 therein. These blade locking slots 268 allow the flexible medial calcar osteotome blade 260 having a spoon-shaped cutting edge 262 to be securely locked into the surgical blade locking osteotome handle assembly 220 (see detail above). The spoon-shaped cutting edge 262 is both flexible and includes a uniquely designed curvature with sharpened spoon-shaped cutting edges to make cutting the medial calcar implant surface from the bone more efficient. What's the difference between a surgical chisel and an osteotome blade? An osteotome is an orthopedic instrument that is typically used for cutting bone. A surgical chisel is used for shaping bone. Functionally, the primary difference is that a chisel has one beveled edge, while an osteotome has two beveled edges. Additionally, the flexible medial calcar osteotome blade 260 having a spoon-shaped cutting edge 262 can be configured to be an osteotome blade having two of the sharpened cutting edges beveled or configured to be a surgical chisel wherein only one side of the sharpened cutting edge is beveled. Here, in FIG. 69 there is shown flexible medial calcar osteotome blade 260 having a spoon-shaped cutting edge 262 having a chisel cutting edge with only one side beveled. It is anticipated that the same flexible medial calcar osteotome blade 260 having a spoon-shaped cutting edge 262 could be configured as an osteotome blade having both sides of the sharpened cutting edge beveled.

FIG. 70 depicts a front view of a flexible medial calcar osteotome blade 260 having a spoon-shaped cutting edge 262. The flexible medial calcar osteotome blade 260 having a spoon-shaped cutting edge 262 also includes the following features: a blade shaft 264 and a blade insertion plate 266 distal to the spoon-shaped cutting edge 262. The blade insertion plate 266 defines one or more blade locking slots 268 therein. These blade locking slots 268 allow the flexible medial calcar osteotome blade 260 having a spoon-shaped cutting edge 262 to be securely locked into the surgical blade locking osteotome handle assembly 220 (see detail above). The spoon-shaped cutting edge 262 is both flexible and includes a uniquely designed curvature with sharpened spoon-shaped cutting edges to make cutting the medial calcar implant surface from the bone more efficient.

FIG. 71 depicts a cross-sectional view of the flexible medial calcar osteotome blade 260 having a spoon-shaped cutting edge 262, as shown in FIG. 70. The flexible medial calcar osteotome blade 260 having a spoon-shaped cutting edge 262 also includes the following features: a blade shaft 264 and a blade insertion plate 266 distal to the spoon-shaped cutting edge 262. The blade insertion plate 266 defines one or more blade locking slots 268 therein. These blade locking slots 268 allow the flexible medial calcar osteotome blade 260 having a spoon-shaped cutting edge 262 to be securely locked into the surgical blade locking osteotome handle assembly 220 (see detail above). The spoon-shaped cutting edge 262 is both flexible and includes a uniquely designed curvature with sharpened spoon-shaped cutting edges to make cutting the medial calcar implant surface from the bone more efficient.

Figures 72, 73, 74, 75, 76, 77:
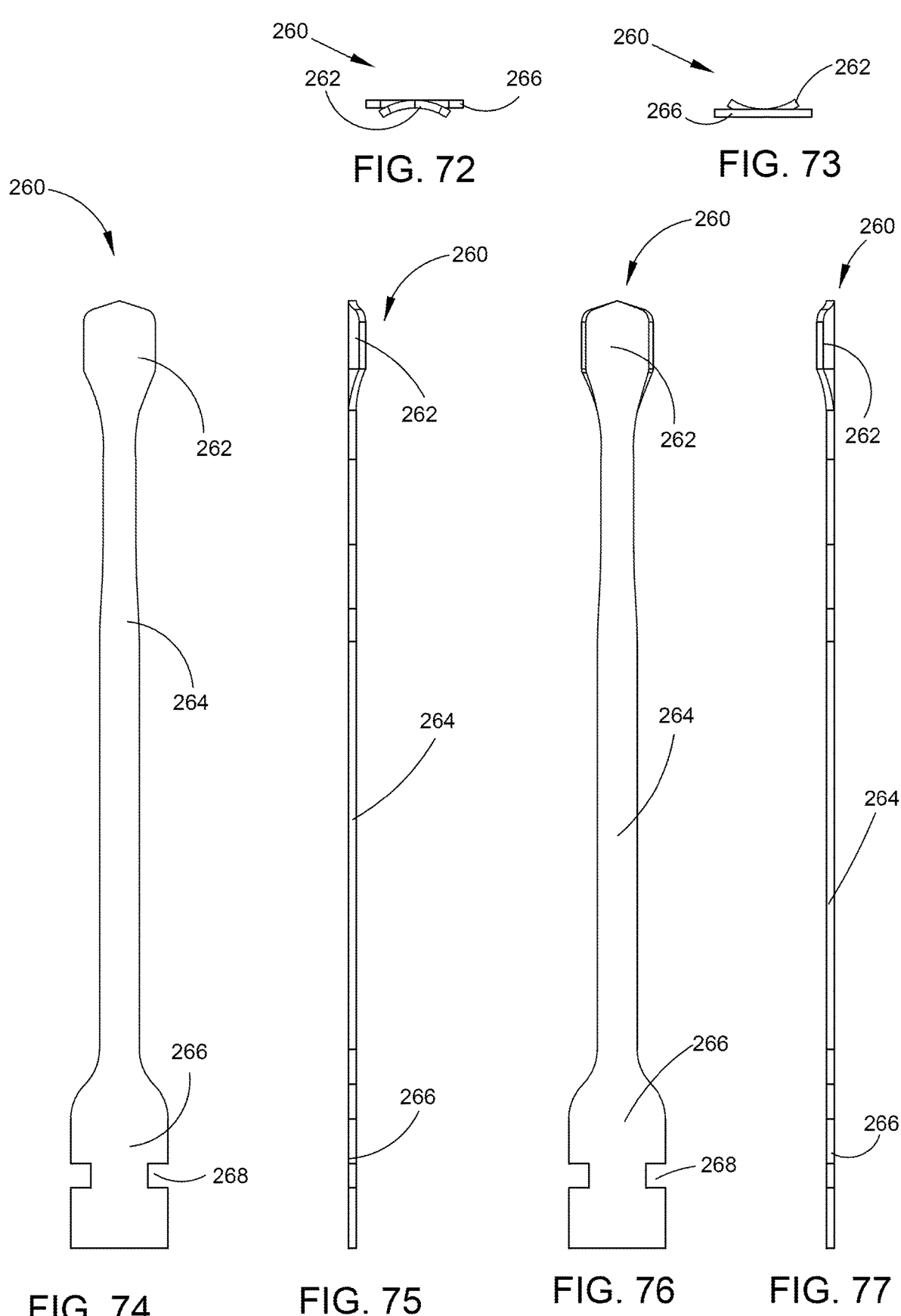
FIG. 72 depicts a top plan view of a flexible medial calcar osteotome blade having a spoon-shaped cutting edge.
FIG. 73 depicts a bottom view of a flexible medial calcar osteotome blade having a spoon-shaped cutting edge.
FIG. 74 depicts a rear view of a flexible medial calcar osteotome blade having a spoon-shaped cutting edge.
FIG. 75 depicts a left side elevational view of a flexible medial calcar osteotome blade having a spoon-shaped cutting edge.
FIG. 76 depicts a front view of a flexible medial calcar osteotome blade having a spoon-shaped cutting edge.
FIG. 77 depicts a right side elevational view of a flexible medial calcar osteotome blade having a spoon-shaped cutting edge, illustrating the opposite side from FIG. 75.

FIG. 72 depicts a top plan view of a flexible medial calcar osteotome blade 260 having a spoon-shaped cutting edge 262 and a blade insertion plate 266.

FIG. 73 depicts a bottom view of a flexible medial calcar osteotome blade 260 having a spoon-shaped cutting edge 262 and a blade insertion plate 266.

FIG. 74 depicts a rear view of a flexible medial calcar osteotome blade 260 having a spoon-shaped cutting edge 262. The flexible medial calcar osteotome blade 260 having a spoon-shaped cutting edge 262 also includes the following features: a blade shaft 264 and a blade insertion plate 266 distal to the spoon-shaped cutting edge 262. The blade insertion plate 266 defines one or more blade locking slots 268 therein. These blade locking slots 268 allow the flexible medial calcar osteotome blade 260 having a spoon-shaped cutting edge 262 to be securely locked into the surgical blade locking osteotome handle assembly 220 (see detail above). The spoon-shaped cutting edge 262 is both flexible and includes a uniquely designed curvature with sharpened spoon-shaped cutting edges to make cutting the medial calcar implant surface from the bone more efficient.

FIG. 75 depicts a left side elevational view of a flexible medial calcar osteotome blade 260 having a spoon-shaped cutting edge 262. The flexible medial calcar osteotome blade 260 having a spoon-shaped cutting edge 262 also includes the following features: a blade shaft 264 and a blade insertion plate 266 distal to the spoon-shaped cutting edge 262. The blade insertion plate 266 defines one or more blade locking slots 268 therein. These blade locking slots 268 allow the flexible medial calcar osteotome blade 260 having a spoon-shaped cutting edge 262 to be securely locked into the surgical blade locking osteotome handle assembly 220 (see detail above). The spoon-shaped cutting edge 262 is both flexible and includes a uniquely designed curvature with sharpened spoon-shaped cutting edges to make cutting the medial calcar implant surface from the bone more efficient.

FIG. 76 depicts a front view of a flexible medial calcar osteotome blade 260 having a spoon-shaped cutting edge 262. The flexible medial calcar osteotome blade 260 having a spoon-shaped cutting edge 262 also includes the following features: a blade shaft 264 and a blade insertion plate 266 distal to the spoon-shaped cutting edge 262. The blade insertion plate 266 defines one or more blade locking slots 268 therein. These blade locking slots 268 allow the flexible medial calcar osteotome blade 260 having a spoon-shaped cutting edge 262 to be securely locked into the surgical blade locking osteotome handle assembly 220 (see detail above). The spoon-shaped cutting edge 262 is both flexible and includes a uniquely designed curvature with sharpened spoon-shaped cutting edges to make cutting the medial calcar implant surface from the bone more efficient.

FIG. 77 depicts a right side elevational view of a flexible medial calcar osteotome blade 260 having a spoon-shaped cutting edge 262, illustrating the opposite side from FIG. 75. The flexible medial calcar osteotome blade 260 having a spoon-shaped cutting edge 262 also includes the following features: a blade shaft 264 and a blade insertion plate 266 distal to the spoon-shaped cutting edge 262. The blade insertion plate 266 defines one or more blade locking slots 268 therein. These blade locking slots 268 allow the flexible medial calcar osteotome blade 260 having a spoon-shaped cutting edge 262 to be securely locked into the surgical blade locking osteotome handle assembly 220 (see detail above). The spoon-shaped cutting edge 262 is both flexible and includes a uniquely designed curvature with sharpened spoon-shaped cutting edges to make cutting the medial calcar implant surface from the bone more efficient.

Figures 78, 79, 80, 81, 82, 83:
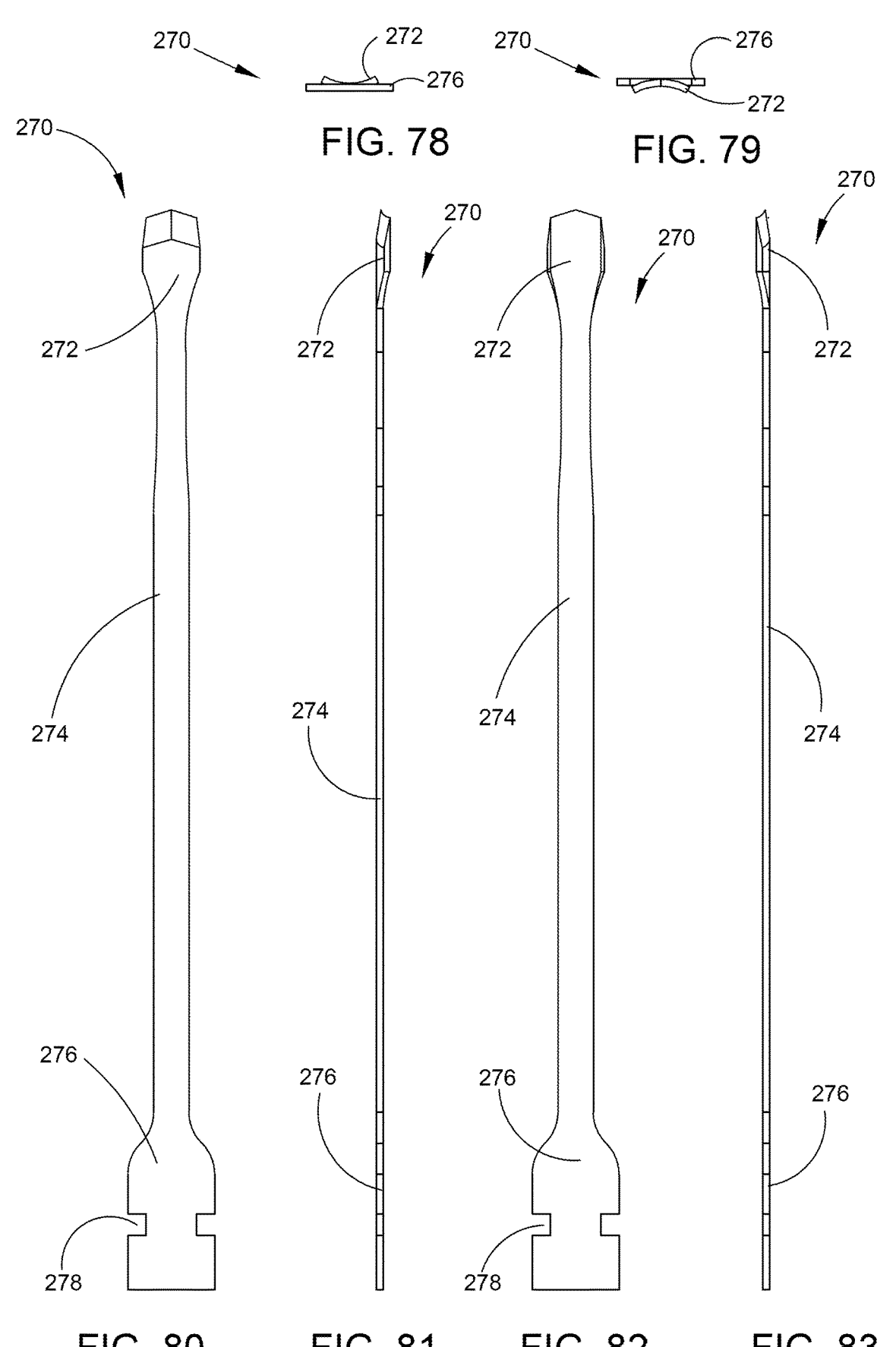
FIG. 78 depicts a bottom view of a flexible medial calcar osteotome blade having a spoon-shaped cutting edge and an elongated blade shaft.
FIG. 79 depicts a top plan view of a flexible medial calcar osteotome blade having a spoon-shaped cutting edge and an elongated blade shaft.
FIG. 80 depicts a rear view of a flexible medial calcar osteotome blade having a spoon-shaped cutting edge and an elongated blade shaft.
FIG. 81 depicts a left side elevational view of a flexible medial calcar osteotome blade having a spoon-shaped cutting edge and an elongated blade shaft.
FIG. 82 depicts a front view of a flexible medial calcar osteotome blade having a spoon-shaped cutting edge and an elongated blade shaft.
FIG. 83 depicts a right side elevational view of a flexible medial calcar osteotome blade having a spoon-shaped cutting edge and an elongated blade shaft.

FIG. 78 depicts a bottom view of an elongated flexible medial calcar osteotome blade 270 having a narrower spoon-shaped cutting edge 272 and an elongated blade shaft 274, as compared to the flexible medial calcar osteotome blade 260 having a spoon-shaped cutting edge 262 and shorter blade shaft 264 shown in FIGS. 69-77.

FIG. 79 depicts a top plan view of a flexible medial calcar osteotome blade 270 having a narrower spoon-shaped cutting edge 272 and an elongated blade shaft 274, as compared to the flexible medial calcar osteotome blade 260 having a spoon-shaped cutting edge 262 and shorter blade shaft 264 shown in FIGS. 69-77.

FIG. 80 depicts a rear view of a flexible medial calcar osteotome blade 270 having a narrower spoon-shaped cutting edge 272 and an elongated blade shaft 274, as compared to the flexible medial calcar osteotome blade 260 having a spoon-shaped cutting edge 262 and shorter blade shaft 264 shown in FIGS. 69-77. The elongated flexible medial calcar osteotome blade 270 having a narrower spoon-shaped cutting edge 272 and an elongated blade shaft 274 also includes the following features: an elongated blade shaft 274 and a blade insertion plate 276 distal to the narrower spoon-shaped cutting edge 272. The blade insertion plate 276 defines one or more blade locking slots 278 therein. These blade locking slots 278 allow the flexible medial calcar osteotome blade 270 having a spoon-shaped cutting edge 272 to be securely locked into the surgical blade locking osteotome handle assembly 220 (see detail above). The narrower spoon-shaped cutting edge 272 is both flexible and includes a uniquely designed curvature with sharpened spoon-shaped cutting edges to make cutting the medial calcar implant surface from the bone more efficient. What's the difference between a surgical chisel and an osteotome blade? An osteotome is an orthopedic instrument that is typically used for cutting bone. A surgical chisel is used for shaping bone. Functionally, the primary difference is that a chisel has one beveled edge, while an osteotome has two beveled edges. Additionally, the flexible medial calcar osteotome blade 270 having a spoon-shaped cutting edge 272 can be configured to be an osteotome blade having two of the sharpened cutting edges beveled or configured to be a surgical chisel wherein only one side of the sharpened cutting edge is beveled. Here, in FIG. 80 there is shown flexible medial calcar osteotome blade 270 having a spoon-shaped cutting edge 272 having a chisel cutting edge with only one side beveled. It is anticipated that the same flexible medial calcar osteotome blade 270 having a spoon-shaped cutting edge 272 could be configured as an osteotome blade having both sides of the sharpened cutting edge beveled. Since osteotome blades includes surgical chisels, from this point forward the osteotome blade/surgical chisels will be referred to simply as osteotome blades.

FIG. 81 depicts a left side elevational view of a flexible medial calcar osteotome blade 270 having a narrower spoon-shaped cutting edge 272 and an elongated blade shaft 274, as compared to the flexible medial calcar osteotome blade 260 having a spoon-shaped cutting edge 262 and shorter blade shaft 264 shown in FIGS. 69-77. The elongated flexible medial calcar osteotome blade 270 having a narrower spoon-shaped cutting edge 272 and an elongated blade shaft 274 also includes the following features: an elongated blade shaft 274 and a blade insertion plate 276 distal to the narrower spoon-shaped cutting edge 272. The blade insertion plate 276 defines one or more blade locking slots 278 therein.

FIG. 82 depicts a front view of a flexible medial calcar osteotome blade 270 having a narrower spoon-shaped cutting edge 272 and an elongated blade shaft 274, as compared to the flexible medial calcar osteotome blade 260 having a spoon-shaped cutting edge 262 and shorter blade shaft 264 shown in FIGS. 69-77. The elongated flexible medial calcar osteotome blade 270 having a narrower spoon-shaped cutting edge 272 and an elongated blade shaft 274 also includes the following features: an elongated blade shaft 274 and a blade insertion plate 276 distal to the narrower spoon-shaped cutting edge 272. The blade insertion plate 276 defines one or more blade locking slots 278 therein.

FIG. 83 depicts a right side elevational view of a flexible medial calcar osteotome blade 270 having a narrower spoon-shaped cutting edge 272 and an elongated blade shaft 274, as compared to the flexible medial calcar osteotome blade 260 having a spoon-shaped cutting edge 262 and shorter blade shaft 264 shown in FIGS. 69-77. The elongated flexible medial calcar osteotome blade 270 having a narrower spoon-shaped cutting edge 272 and an elongated blade shaft 274 also includes the following features: an elongated blade shaft 274 and a blade insertion plate 276 distal to the narrower spoon-shaped cutting edge 272. The blade insertion plate 276 defines one or more blade locking slots 278 therein.

FIG. 84 depicts a top, side elevational and perspective view of a flexible medial calcar osteotome blade 270 having a narrower spoon-shaped cutting edge 272 and an elongated blade shaft 274, as compared to the flexible medial calcar osteotome blade 260 having a spoon-shaped cutting edge 262 and shorter blade shaft 264 shown in FIGS. 69-77. The elongated flexible medial calcar osteotome blade 270 having a narrower spoon-shaped cutting edge 272 and an elongated blade shaft 274 also includes like parts as those previously shown in FIGS. 78-83.

FIG. 85 depicts a front view of a flexible medial calcar osteotome blade 270 having a narrower spoon-shaped cutting edge 272 and an elongated blade shaft 274, as compared to the flexible medial calcar osteotome blade 260 having a spoon-shaped cutting edge 262 and shorter blade shaft 264 shown in FIGS. 69-77. The elongated flexible medial calcar osteotome blade 270 having a narrower spoon-shaped cutting edge 272 and an elongated blade shaft 274 also includes like parts as those previously shown in FIGS. 78-83.

FIG. 86 depicts a cross-sectional view of the flexible medial calcar osteotome blade 270 having a narrower spoon-shaped cutting edge 272 and an elongated blade shaft 274, as compared to the flexible medial calcar osteotome blade 260 having a spoon-shaped cutting edge 262 and shorter blade shaft 264 shown in FIGS. 69-77. The elongated flexible medial calcar osteotome blade 270 having a narrower spoon-shaped cutting edge 272 and an elongated blade shaft 274 also includes like parts as those previously shown in FIGS. 78-83.

Figures 87, 88, 89:
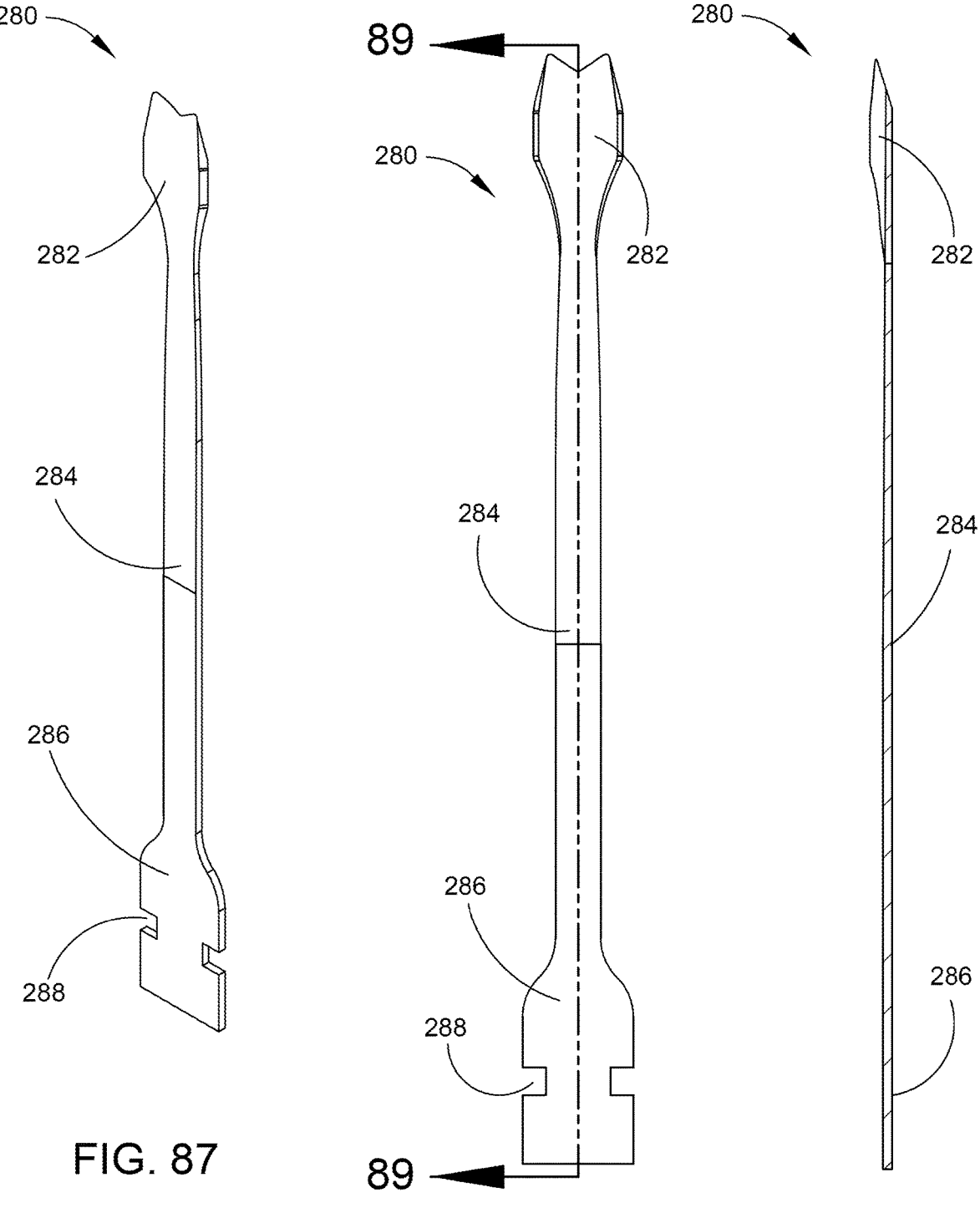
FIG. 87 depicts a top, side elevational and perspective view of a flexible medial calcar osteotome blade having a spork-shaped cutting edge and an elongated blade shaft.
FIG. 88 depicts a front view of a flexible medial calcar osteotome blade having a spork-shaped cutting edge and an elongated blade shaft.
FIG. 89 depicts a cross-sectional view of the flexible medial calcar osteotome blade having a spork-shaped cutting edge and an elongated blade shaft, shown in FIG. 88.

FIG. 87 depicts a top, side elevational and perspective view of a flexible medial calcar osteotome blade 280 having a spork-shaped cutting edge 282. The flexible medial calcar osteotome blade 280 having a spork-shaped cutting edge 282 also includes the following features: a blade shaft 284 and a blade insertion plate 286 distal to the spork-shaped cutting edge 282. The blade insertion plate 286 defines one or more blade locking slots 288 therein. These blade locking slots 288 allow the flexible medial calcar osteotome blade 280 having a spork-shaped cutting edge 282 to be securely locked into the surgical blade locking osteotome handle assembly 220 (see detail above). What's the difference between a surgical chisel and an osteotome blade? An osteotome is an orthopedic instrument that is typically used for cutting bone. A surgical chisel is used for shaping bone. Functionally, the primary difference is that a chisel has one beveled edge, while an osteotome has two beveled edges. Additionally, the flexible medial calcar osteotome blade 280 having a spoon-shaped cutting edge 282 can be configured to be an osteotome blade having two of the sharpened cutting edges beveled or configured to be a surgical chisel wherein only one side of the sharpened cutting edge is beveled. Here, in FIG. 87 there is shown flexible medial calcar osteotome blade 280 having a spoon-shaped cutting edge 282 having a chisel cutting edge with only one side beveled. It is anticipated that the same flexible medial calcar osteotome blade 280 having a spoon-shaped cutting edge 282 could be configured as an osteotome blade having both sides of the sharpened cutting edge beveled.

FIG. 88 depicts a front view of a flexible medial calcar osteotome blade 280 having a spork-shaped cutting edge 282. The flexible medial calcar osteotome blade 280 having a spork-shaped cutting edge 282 also includes the following features: a blade shaft 284 and a blade insertion plate 286 distal to the spork-shaped cutting edge 282. The blade insertion plate 286 defines one or more blade locking slots 288 therein. These blade locking slots 288 allow the flexible medial calcar osteotome blade 280 having a spork-shaped cutting edge 282 to be securely locked into the surgical blade locking osteotome handle assembly 220 (see detail above).

FIG. 89 depicts a cross-sectional view of the flexible medial calcar osteotome blade 280 having a spork-shaped cutting edge 282, as shown in FIG. 88. The flexible medial calcar osteotome blade 280 having a spork-shaped cutting edge 282 also includes the following features: a blade shaft 284 and a blade insertion plate 286 distal to the spork-shaped cutting edge 282. The blade insertion plate 286 defines one or more blade locking slots 288 therein. These blade locking slots 288 allow the flexible medial calcar osteotome blade 280 having a spork-shaped cutting edge 282 to be securely locked into the surgical blade locking osteotome handle assembly 220 (see detail above). The spork-shaped cutting edge 282 is both flexible and includes a uniquely designed curvature with sharpened spork-shaped cutting edges to make cutting the medial calcar implant surface from the bone significantly more efficient.

Figures 90, 91, 92, 93, 94, 95:
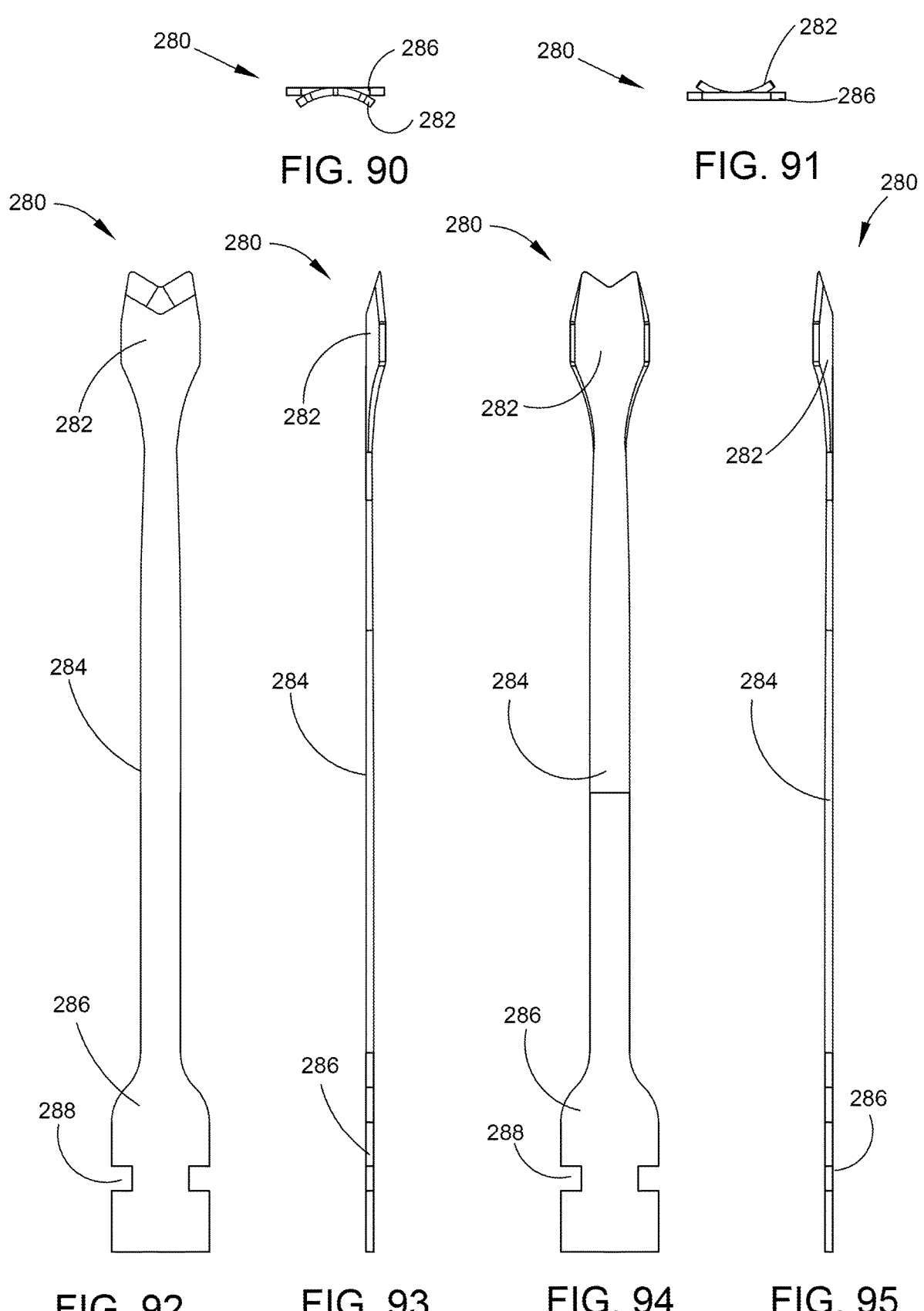
FIG. 90 depicts a top plan view of a flexible medial calcar osteotome blade having a spork-shaped cutting edge.
FIG. 91 depicts a bottom view of a flexible medial calcar osteotome blade having a spork-shaped cutting edge.
FIG. 92 depicts a rear view of a flexible medial calcar osteotome blade having a spork-shaped cutting edge.
FIG. 93 depicts a left side elevational view of a flexible medial calcar osteotome blade having a spork-shaped cutting edge.
FIG. 94 depicts a front view of a flexible medial calcar osteotome blade having a spork-shaped cutting edge.
FIG. 95 depicts a right side elevational view of a flexible medial calcar osteotome blade having a spork-shaped cutting edge.

FIG. 90 depicts a top plan view of a flexible medial calcar osteotome blade 280 having a spork-shaped cutting edge 282 and a blade insertion plate 286.

FIG. 91 depicts a bottom view of a flexible medial calcar osteotome blade 280 having a spork-shaped cutting edge 282 and a blade insertion plate 286.

FIG. 92 depicts a rear view of a flexible medial calcar osteotome blade 280 having a spork-shaped cutting edge 282, as shown in FIG. 87. The flexible medial calcar osteotome blade 280 having a spork-shaped cutting edge 282 also includes the following features: a blade shaft 284 and a blade insertion plate 286 distal to the spork-shaped cutting edge 282. The blade insertion plate 286 defines one or more blade locking slots 288 therein. What's the difference between a surgical chisel and an osteotome blade? An osteotome is an orthopedic instrument that is typically used for cutting bone. A surgical chisel is used for shaping bone. Functionally, the primary difference is that a chisel has one beveled edge, while an osteotome has two beveled edges. Additionally, the flexible medial calcar osteotome blade 280 having a spork-shaped cutting edge 282 can be configured to be an osteotome blade having two of the sharpened cutting edges beveled or configured to be a surgical chisel wherein only one side of the sharpened cutting edge is beveled. Here, in FIG. 92 there is shown flexible medial calcar osteotome blade 280 having a spork-shaped cutting edge 282 having a chisel cutting edge with only one side beveled. It is anticipated that the same flexible medial calcar osteotome blade 280 having a spork-shaped cutting edge 282 could be configured as an osteotome blade having both sides of the sharpened cutting edge beveled.

FIG. 93 depicts a left side elevational view of a flexible medial calcar osteotome blade 280 having a spork-shaped cutting edge 282, as shown in FIG. 87. The flexible medial calcar osteotome blade 280 having a spork-shaped cutting edge 282 also includes the following features: a blade shaft 284 and a blade insertion plate 286 distal to the spork-shaped cutting edge 282. The blade insertion plate 286 defines one or more blade locking slots 288 therein.

FIG. 94 depicts a front view of a flexible medial calcar osteotome blade 280 having a spork-shaped cutting edge 282, as shown in FIG. 87. The flexible medial calcar osteotome blade 280 having a spork-shaped cutting edge 282 also includes the following features: a blade shaft 284 and a blade insertion plate 286 distal to the spork-shaped cutting edge 282. The blade insertion plate 286 defines one or more blade locking slots 288 therein.

FIG. 95 depicts a right side elevational view of a flexible medial calcar osteotome blade 280 having a spork-shaped cutting edge 282, as shown in FIG. 87. The flexible medial calcar osteotome blade 280 having a spork-shaped cutting edge 282 also includes the following features: a blade shaft 284 and a blade insertion plate 286 distal to the spork-shaped cutting edge 282. The blade insertion plate 286 defines one or more blade locking slots 288 therein.

Figures 96, 97, 98:
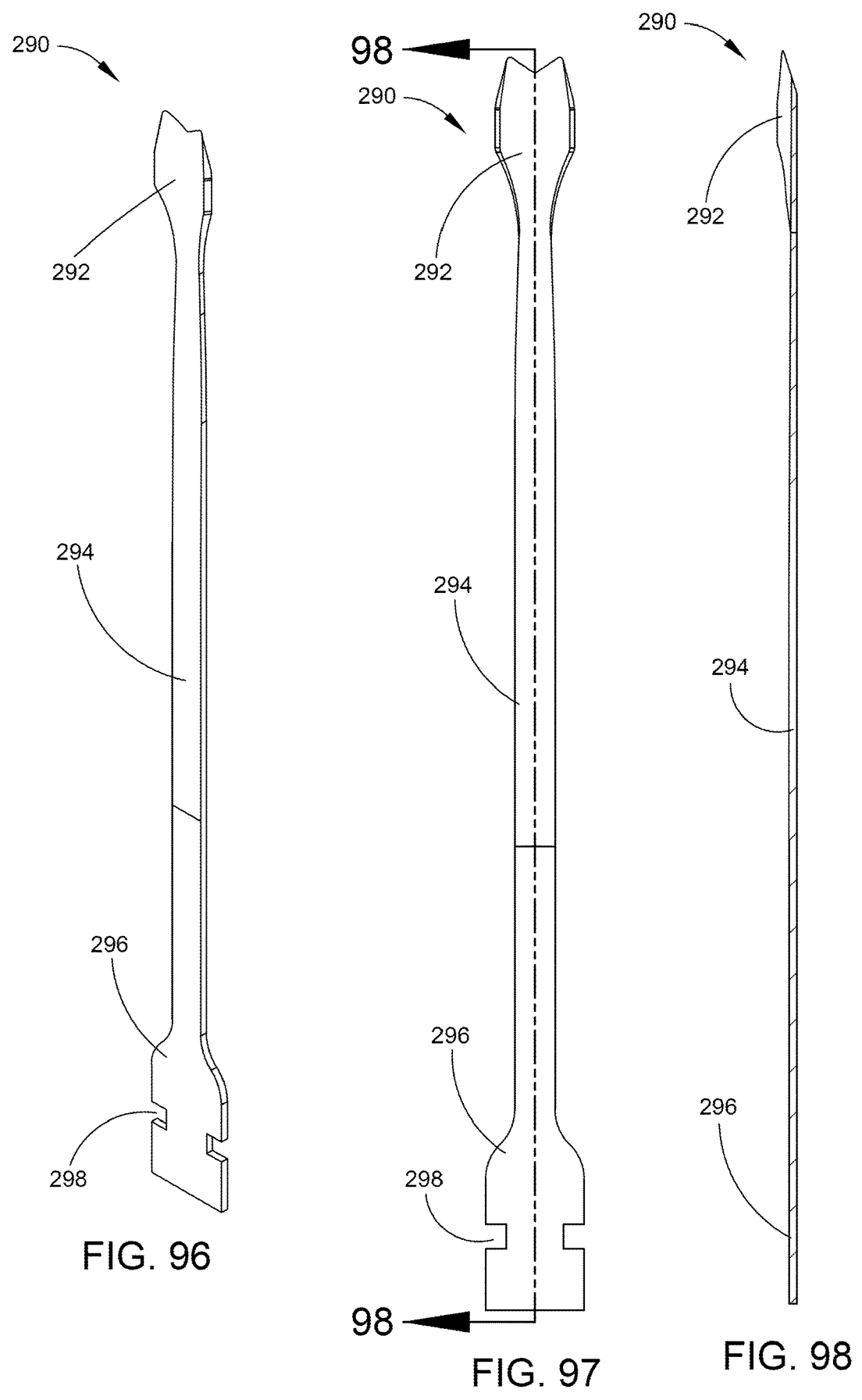

FIG. 96 depicts a top, side elevational and perspective view of a flexible medial calcar osteotome blade 290 having a narrower spork-shaped cutting edge 292 and an elongated blade shaft 294, as compared to the flexible medial calcar osteotome blade 280 having a spork-shaped cutting edge 282 and shorter blade shaft 284 shown in FIGS. 87-95. The elongated flexible medial calcar osteotome blade 290 having a narrower spork-shaped cutting edge 292 and an elongated blade shaft 294 also includes the following features: an elongated blade shaft 294 and a blade insertion plate 296 distal to the narrower spork-shaped cutting edge 292. The blade insertion plate 296 defines one or more blade locking slots 298 therein. These blade locking slots 298 allow the elongated flexible medial calcar osteotome blade 290 having a narrower spork-shaped cutting edge 292 to be securely locked into the surgical blade locking osteotome handle assembly 220 (see detail above). The narrower spoon-shaped cutting edge 292 is both flexible and includes a uniquely designed curvature with sharpened spoon-shaped cutting edges to make cutting the medial calcar implant surface from the bone more efficient.

FIG. 97 depicts a front view of a flexible medial calcar osteotome blade 290 having a narrow spork-shaped cutting edge 292 and an elongated blade shaft 294. The blade insertion plate 296 defines one or more blade locking slots 298 therein. These blade locking slots 298 allow the elongated flexible medial calcar osteotome blade 290 having a narrower spork-shaped cutting edge 292 to be securely locked into the surgical blade locking osteotome handle assembly 220 (see detail above).

FIG. 98 depicts a cross-sectional view of the flexible medial calcar osteotome blade 290 having a narrow spork-shaped cutting edge 292 and an elongated blade shaft 294, as shown in FIG. 97. The flexible medial calcar osteotome blade 290 having a spork-shaped cutting edge 292 also includes the following features: a blade shaft 294 and a blade insertion plate 296 distal to the spork-shaped cutting edge 292.

Figures 99, 100, 101, 102, 103, 104:
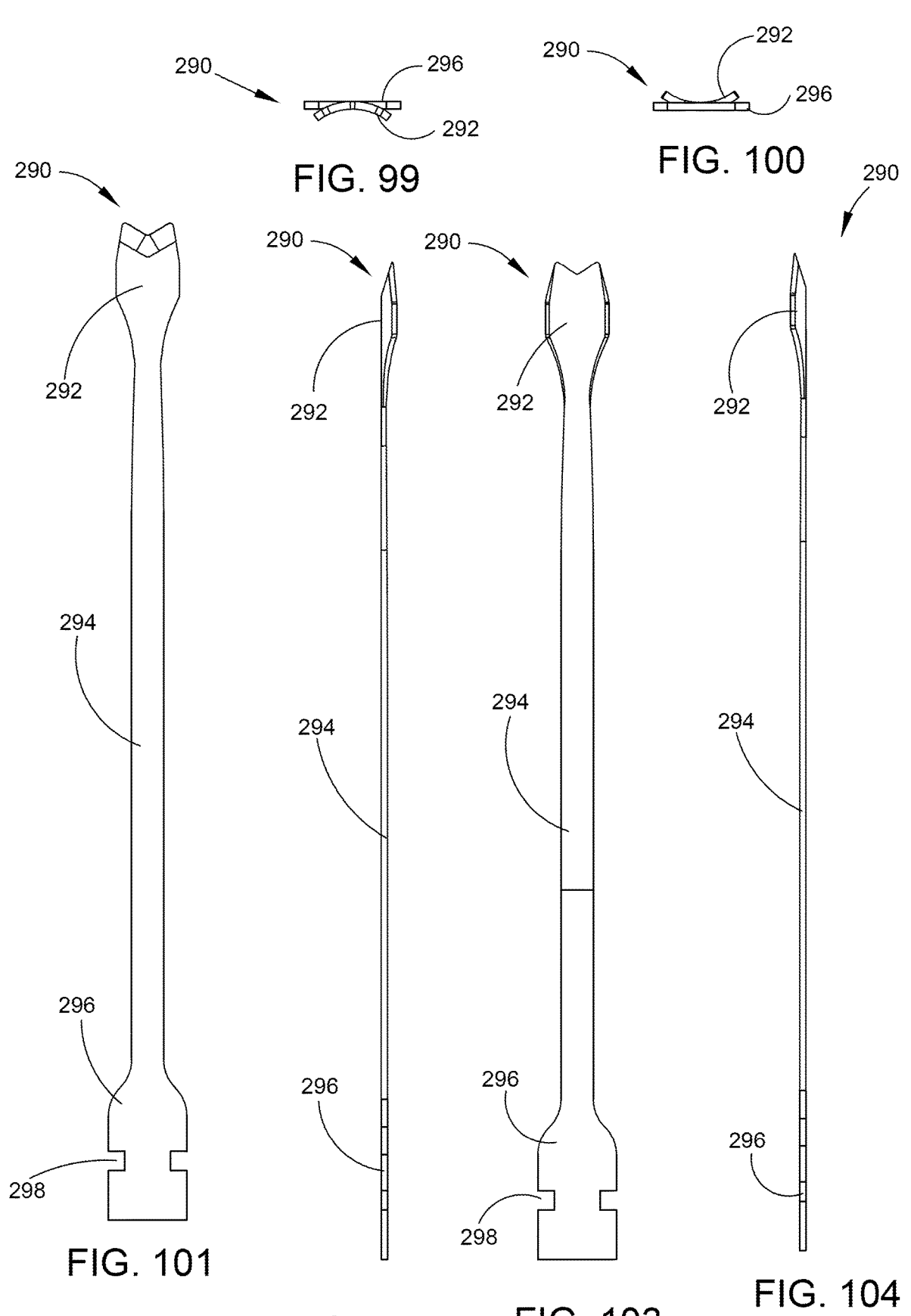
FIG. 99 depicts a top plan view of a flexible medial calcar osteotome blade having a spork-shaped cutting edge and an elongated blade shaft.
FIG. 100 depicts a bottom view of a flexible medial calcar osteotome blade having a spork-shaped cutting edge and an elongated blade shaft.
FIG. 101 depicts a rear view of a flexible medial calcar osteotome blade having a spork-shaped cutting edge and an elongated blade shaft.
FIG. 102 depicts a left side elevational view of a flexible medial calcar osteotome blade having a spork-shaped cutting edge and an elongated blade shaft.
FIG. 103 depicts a front view of a flexible medial calcar osteotome blade having a spork-shaped cutting edge and an elongated blade shaft.
FIG. 104 depicts a right side elevational view of a flexible medial calcar osteotome blade having a spork-shaped cutting edge and an elongated blade shaft.

FIG. 99 depicts a top plan view of a flexible medial calcar osteotome blade 290 having a narrow spork-shaped cutting edge 292 and an elongated blade shaft 294 and showing the position of the narrow spork-shaped cutting edge 292 and the blade insertion plate 296.

FIG. 100 depicts a bottom view of a flexible medial calcar osteotome blade 290 having a narrow spork-shaped cutting edge 292 and an elongated blade shaft 294 and showing the position of the narrow spork-shaped cutting edge 292 and the blade insertion plate 296.

FIG. 101 depicts a rear view of a flexible medial calcar osteotome blade 290 having a narrow spork-shaped cutting edge 292 and an elongated blade shaft 294 and showing the elongated blade shaft 294 as well as the blade insertion plate 296 and one or more blade locking slots 298 therein. What's the difference between a surgical chisel and an osteotome blade? An osteotome is an orthopedic instrument that is typically used for cutting bone. A surgical chisel is used for shaping bone. Functionally, the primary difference is that a chisel has one beveled edge, while an osteotome has two beveled edges. Additionally, the flexible medial calcar osteotome blade 290 having a spork-shaped cutting edge 292 can be configured to be an osteotome blade having two of the sharpened cutting edges beveled or configured to be a surgical chisel wherein only one side of the sharpened cutting edge is beveled. Here, in FIG. 101 there is shown flexible medial calcar osteotome blade 290 having a spork-shaped cutting edge 292 having a chisel cutting edge with only one side beveled. It is anticipated that the same flexible medial calcar osteotome blade 290 having a spork-shaped cutting edge 292 could be configured as an osteotome blade having both sides of the sharpened cutting edge beveled.

FIG. 102 depicts a left side elevational view of a flexible medial calcar osteotome blade 290 having a narrow spork-shaped cutting edge 292 and an elongated blade shaft 294 and showing the elongated blade shaft 294 as well as the blade insertion plate 296.

FIG. 103 depicts a front view of a flexible medial calcar osteotome blade having a spork-shaped cutting edge and an elongated blade shaft. The blade insertion plate 286 defines one or more blade locking slots 288 therein. These blade locking slots 288 allow the flexible medial calcar osteotome blade 280 having a spork-shaped cutting edge 282 to be securely locked into the surgical blade locking osteotome handle assembly 220 (see detail above). The spork-shaped cutting edge 282 is both flexible and includes a uniquely designed curvature with sharpened spork-shaped cutting edges to make cutting the medial calcar implant surface from the bone significantly more efficient.

FIG. 104 depicts a right side elevational view of a flexible medial calcar osteotome blade 290 having a narrow spork-shaped cutting edge 292 and an elongated blade shaft 294 and showing the elongated blade shaft 294 as well as the blade insertion plate 296.

Figures 105, 106, 107, 108, 109, 110:
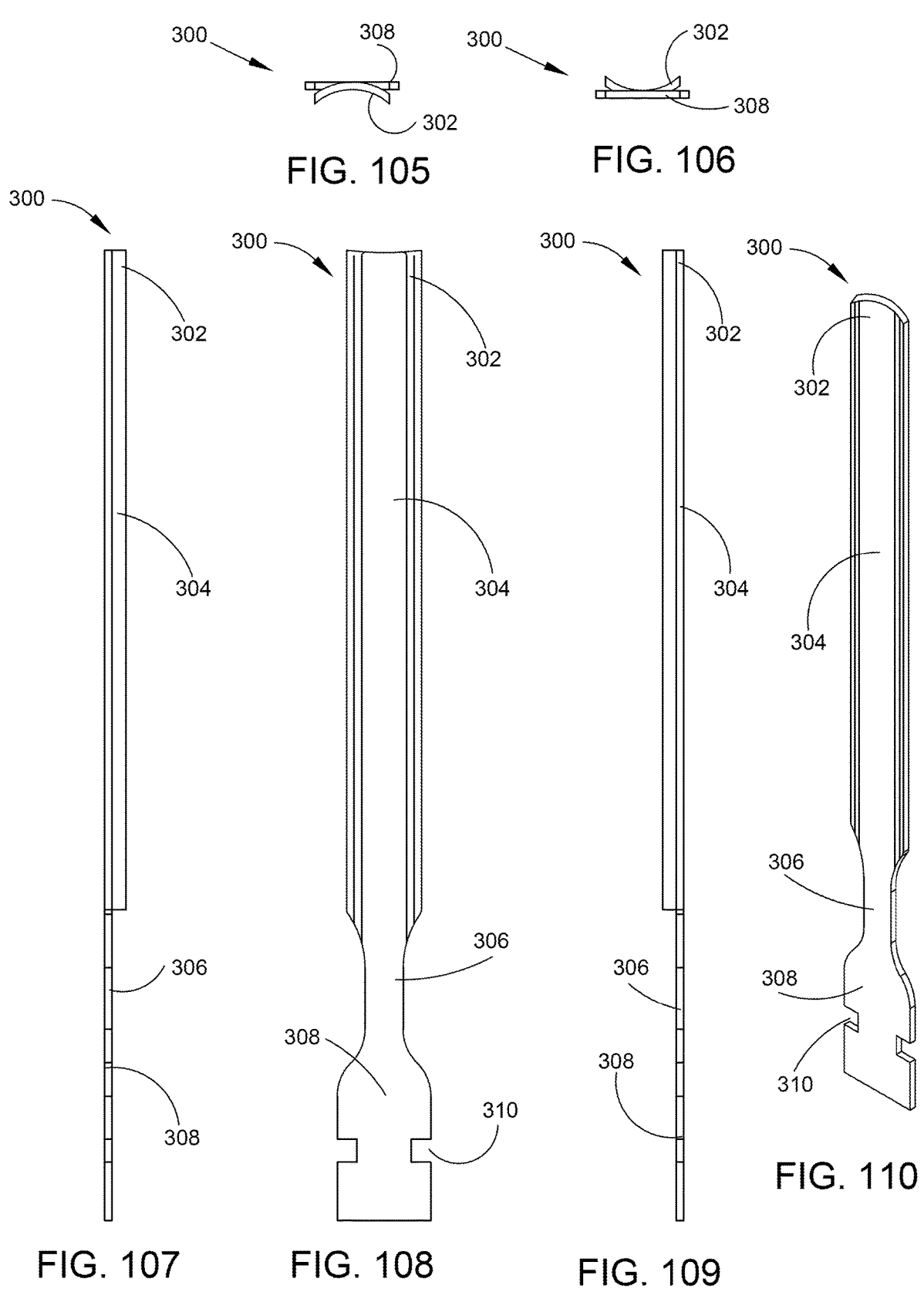
FIG. 105 depicts a top plan view of a curved lateral shoulder release osteotome blade.
FIG. 106 depicts a bottom view of a curved lateral shoulder release osteotome blade.
FIG. 107 depicts a left side elevational view of a curved lateral shoulder release osteotome blade.
FIG. 108 depicts a front view of a curved lateral shoulder release osteotome blade.
FIG. 109 depicts a right side elevational view of a curved lateral shoulder release osteotome blade.
FIG. 110 depicts a top, side elevational and perspective view of a curved lateral shoulder release osteotome blade.

FIG. 105 depicts a top plan view of a curved lateral shoulder release osteotome blade 300 illustrating the curved cutting edge 302 and the flat blade insertion plate 308.

FIG. 106 depicts a bottom view of a curved lateral shoulder release osteotome blade 300 illustrating the curved cutting edge 302 and the flat blade insertion plate 308.

FIG. 107 depicts a left side elevational view of a curved lateral shoulder release osteotome blade 300 illustrating the curved cutting edge 302. Additional features of the curved lateral shoulder release osteotome blade 300 include a blade shaft 304 having a blade shaft narrow section 306 before reaching the blade insertion plate 308.

FIG. 108 depicts a front view of a curved lateral shoulder release osteotome blade 300 illustrating the curved cutting edge 302. Additional features of the curved lateral shoulder release osteotome blade 300 include a curved blade shaft 304 having a flat blade shaft narrow section 306 before reaching the flat blade insertion plate 308. One or more blade locking slots 310 are located within the blade insertion plate 308.

FIG. 109 depicts a right side elevational view of a curved lateral shoulder release osteotome blade 300 illustrating the curved cutting edge 302. Additional features of the curved lateral shoulder release osteotome blade 300 include a curved blade shaft 304 having a flat blade shaft narrow section 306 before reaching the flat blade insertion plate 308.

FIG. 110 depicts a top, side elevational and perspective view of a curved lateral shoulder release osteotome blade 300 illustrating the curved cutting edge 302. Additional features of the curved lateral shoulder release osteotome blade 300 include a curved blade shaft 304 having a flat blade shaft narrow section 306 before reaching the flat blade insertion plate 308. One or more blade locking slots 310 are located within the blade insertion plate 308.

Figures 111, 112, 113:
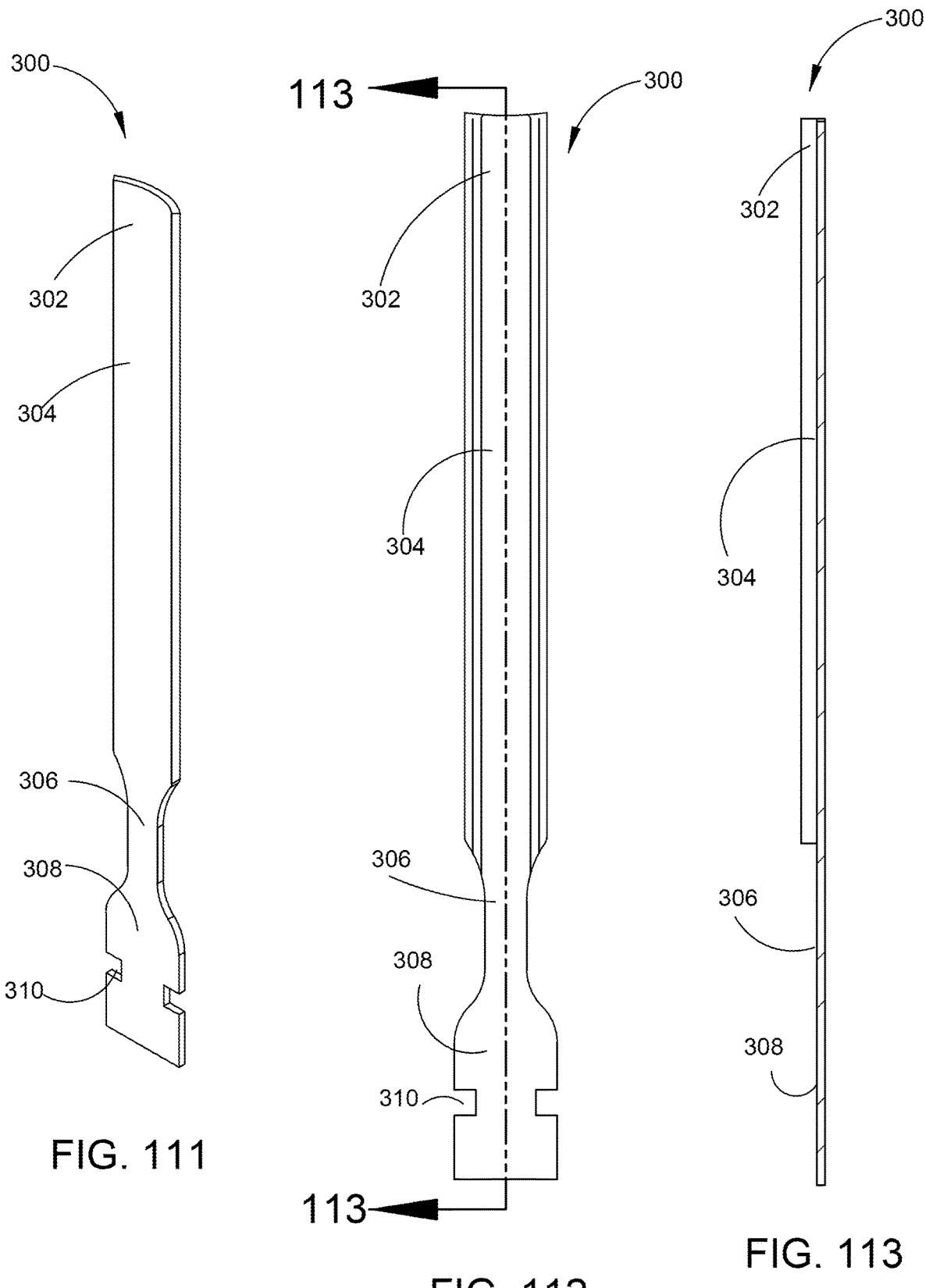
FIG. 111 depicts a top, side elevational and perspective view of a curved lateral shoulder release osteotome blade.
FIG. 112 depicts a front view of a curved lateral shoulder release osteotome blade.
FIG. 113 depicts a cross-sectional view of the curved lateral shoulder release osteotome blade, as shown in FIG. 112.

FIG. 111 depicts a top, side elevational and perspective view of a curved lateral shoulder release osteotome blade 300 illustrating the curved cutting edge 302. Additional features of the curved lateral shoulder release osteotome blade 300 include a curved blade shaft 304 having a flat blade shaft narrow section 306 before reaching the flat blade insertion plate 308. One or more blade locking slots 310 are located within the flat blade insertion plate 308.

FIG. 112 depicts a front view of a curved lateral shoulder release osteotome blade 300 illustrating the curved cutting edge 302. Clearly seen are the additional features of the curved lateral shoulder release osteotome blade 300 including a curved blade shaft 304 having a flat blade shaft narrow section 306 before reaching the blade insertion plate 308, and one or more blade locking slots 310 are located within the flat blade insertion plate 308.

FIG. 113 depicts a cross-sectional view of the curved lateral shoulder release osteotome blade 300, illustrating the curved cutting edge 302, as shown in FIG. 112. Clearly seen are the additional features of the curved lateral shoulder release osteotome blade 300 including a curved blade shaft 304 having a blade shaft narrow section 306 before reaching the blade insertion plate 308.

Figures 114, 115, 116, 117, 118, 119:
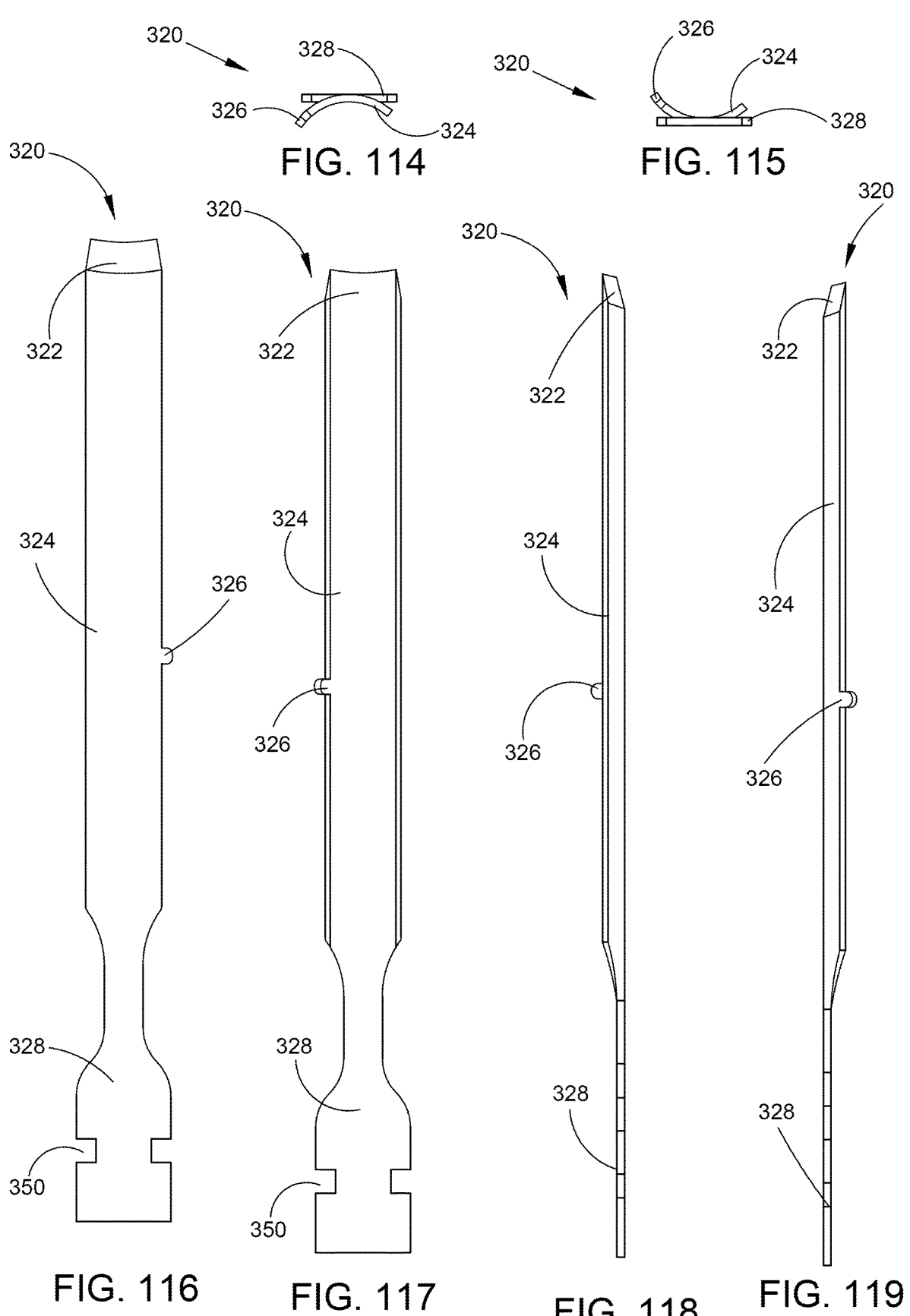
FIG. 114 depicts a top plan view of a curved lateral shoulder release osteotome blade having a protruding stop feature on the blade shaft.
FIG. 115 depicts a bottom view of a curved lateral shoulder release osteotome blade having a protruding stop feature on the blade shaft.
FIG. 116 depicts a rear view of a curved lateral shoulder release osteotome blade having a protruding stop feature on the blade shaft.
FIG. 117 depicts a front view of a curved lateral shoulder release osteotome blade having a protruding stop feature on the blade shaft.
FIG. 118 depicts a right side elevational view of a curved lateral shoulder release osteotome blade having a protruding stop feature on the blade shaft.

FIG. 114 depicts a top plan view of an alternate embodiment of a curved lateral shoulder release osteotome blade 320 having a protruding stop 326 feature on the curved blade shaft 324. In this view the blade insertion plate 328 can also be clearly seen.

FIG. 115 depicts a bottom view of a curved lateral shoulder release osteotome blade 320 having a protruding stop 326 feature on the curved blade shaft 324. In this view the blade insertion plate 328 can also be clearly seen.

FIG. 116 depicts a rear view of a curved lateral shoulder release osteotome blade 320 having a protruding stop 326 feature on the curved blade shaft 324. The protruding stop feature 326 is located approximately half way down the curved blade shaft 324 between the cutting edge 322 and the blade insertion plate 328. The curved blade shaft 324 also has a narrowing section above the blade insertion plate 328. Additional features of the blade insertion plate 328 include one or more blade locking slots 350 located within the blade insertion plate 328. What's the difference between a surgical chisel and an osteotome blade? An osteotome is an orthopedic instrument that is typically used for cutting bone. A surgical chisel is used for shaping bone. Functionally, the primary difference is that a chisel has one beveled edge, while an osteotome has two beveled edges. Additionally, the curved lateral shoulder release osteotome blade 320 having a protruding stop 326 feature on the curved blade shaft can be configured to be an osteotome blade having two of the sharpened cutting edges beveled or configured to be a surgical chisel wherein only one side of the sharpened cutting edge is beveled. Here, in FIG. 116 there is shown a curved lateral shoulder release osteotome blade 320 having a protruding stop 326 feature on the curved blade shaft 324 having a chisel cutting edge with only one side beveled. It is anticipated that the same curved lateral shoulder release osteotome blade 320 having a protruding stop 326 feature on the curved blade shaft 324 could be configured as an osteotome blade having both sides of the sharpened cutting edge beveled.

FIG. 117 depicts a front view of a curved lateral shoulder release osteotome blade 320 having a protruding stop 326 feature on the curved blade shaft 324. Again, the protruding stop feature 326 is located approximately half way down the curved blade shaft 324 between the cutting edge 322 and the blade insertion plate 328. The curved blade shaft 324 also has a narrowing section above the blade insertion plate 328. Additional features of the blade insertion plate 328 include one or more blade locking slots 350 located within the blade insertion plate 328.

FIG. 118 depicts a right side elevational view of a curved lateral shoulder release osteotome blade 320 having a protruding stop feature 326 on the curved blade shaft 324. This right side elevational view illustrates the location of the protruding stop feature 326 in relation to the position of the cutting edge 322 and the blade insertion plate 328.

FIG. 119 depicts a left side elevational view of a curved lateral shoulder release osteotome blade 320 having a protruding stop feature 326 on the blade shaft. This left side elevational view also better illustrates the location of the protruding stop feature 326 in relation to the position of the cutting edge 322 and the blade insertion plate 328.

Figures 120, 121, 122:
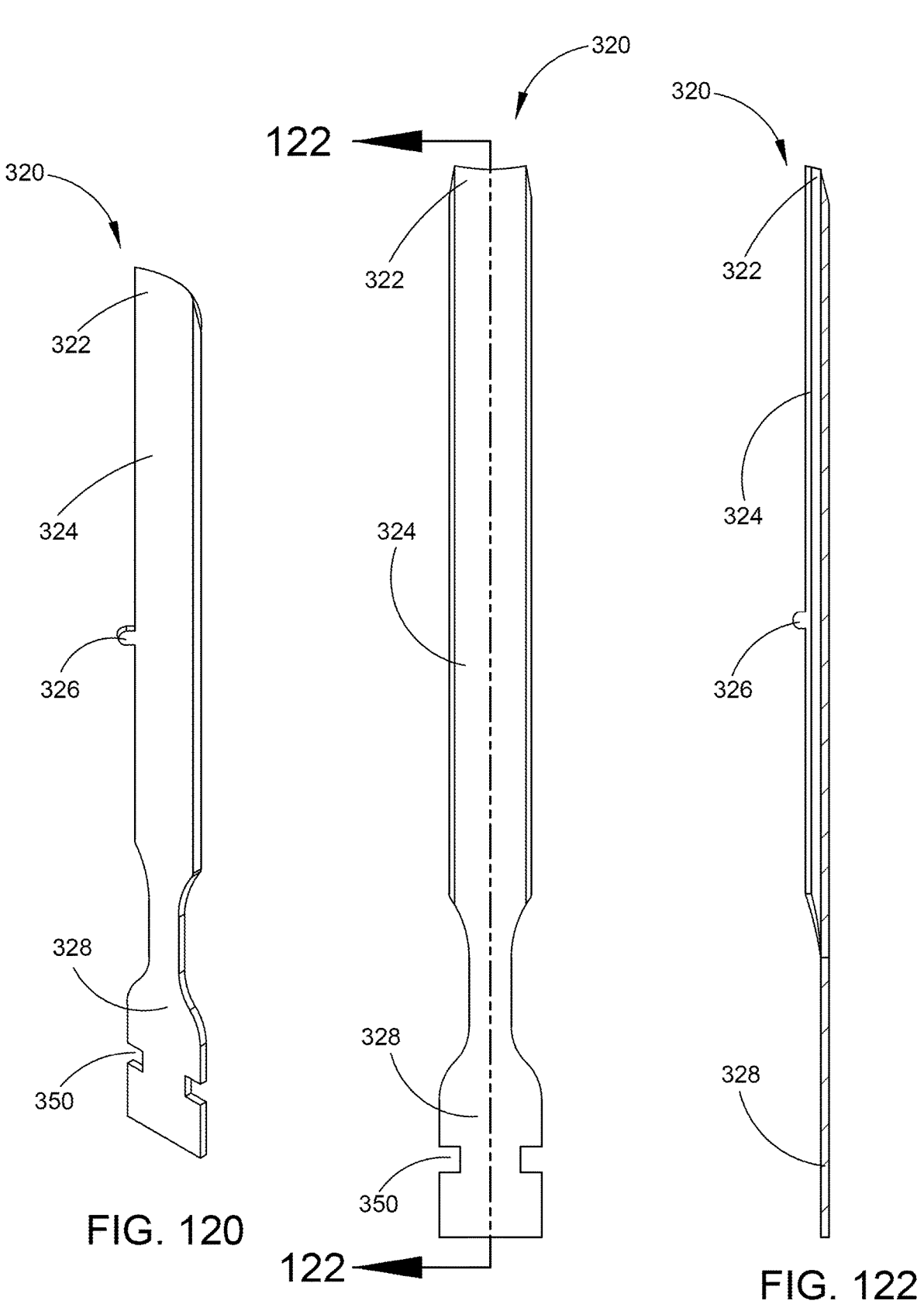

FIG. 120 depicts a top, side elevational and perspective view of a curved lateral shoulder release osteotome blade 320 having a protruding stop feature 326 on the blade shaft. This top, side elevational and perspective view also better illustrates the location of the protruding stop feature 326 in relation to the position of the cutting edge 322 and the blade insertion plate 328. The protruding stop feature 326 is located approximately half way down the curved blade shaft 324 between the cutting edge 322 and the blade insertion plate 328. The curved blade shaft 324 also has a narrowing section above the blade insertion plate 328. Additional features of the blade insertion plate 328 include one or more blade locking slots 350 located within the blade insertion plate 328. In operation, the curved lateral shoulder release osteotome blade 320 is first locked into the handle assembly 220 then inserted into one of the plurality of rearward guide slots 32 within the guide block assembly 20. The surgeon then puts downward pressure on the handle assembly 220 thereby causing the curved lateral shoulder release osteotome blade 320 to extend downward and cut the lateral shoulder of an implant 130 during revision surgery (see FIG. 68). In FIG. 68 the surgical blade 238 shown is equivalent to the curved lateral shoulder release osteotome blade 320 shown here in FIG. 120. In this way, the lateral shoulder of the implant is released from the bone, leaving the medial calcar and the anterior and posterior sides to be released for extraction of the implant 130 from the bone.

FIG. 121 depicts a front view of a curved lateral shoulder release osteotome blade 320 having a protruding stop feature 326 on the blade shaft, and this view also better illustrates the location of the protruding stop feature 326 in relation to the position of the cutting edge 322 and the blade insertion plate 328. The protruding stop feature 326 is located approximately half way down the curved blade shaft 324 between the cutting edge 322 and the blade insertion plate 328. The curved blade shaft 324 also has a narrowing section above the blade insertion plate 328. Additional features of the blade insertion plate 328 include one or more blade locking slots 350 located within the blade insertion plate 328, having a protruding stop feature on the blade shaft.

FIG. 122 depicts a cross-sectional view of the curved lateral shoulder release osteotome blade 320 having a protruding stop feature 326 on the curved blade shaft 324, as shown in FIG. 121. This cross-sectional view illustrates the location of the blade cutting edge 322, the curved blade shaft 324 having a narrow section, the blade insertion plate 328 and the location of the protruding stop feature 326 in relation to the position of the cutting edge 322 and the blade insertion plate 328.

Figures 123, 124, 125:
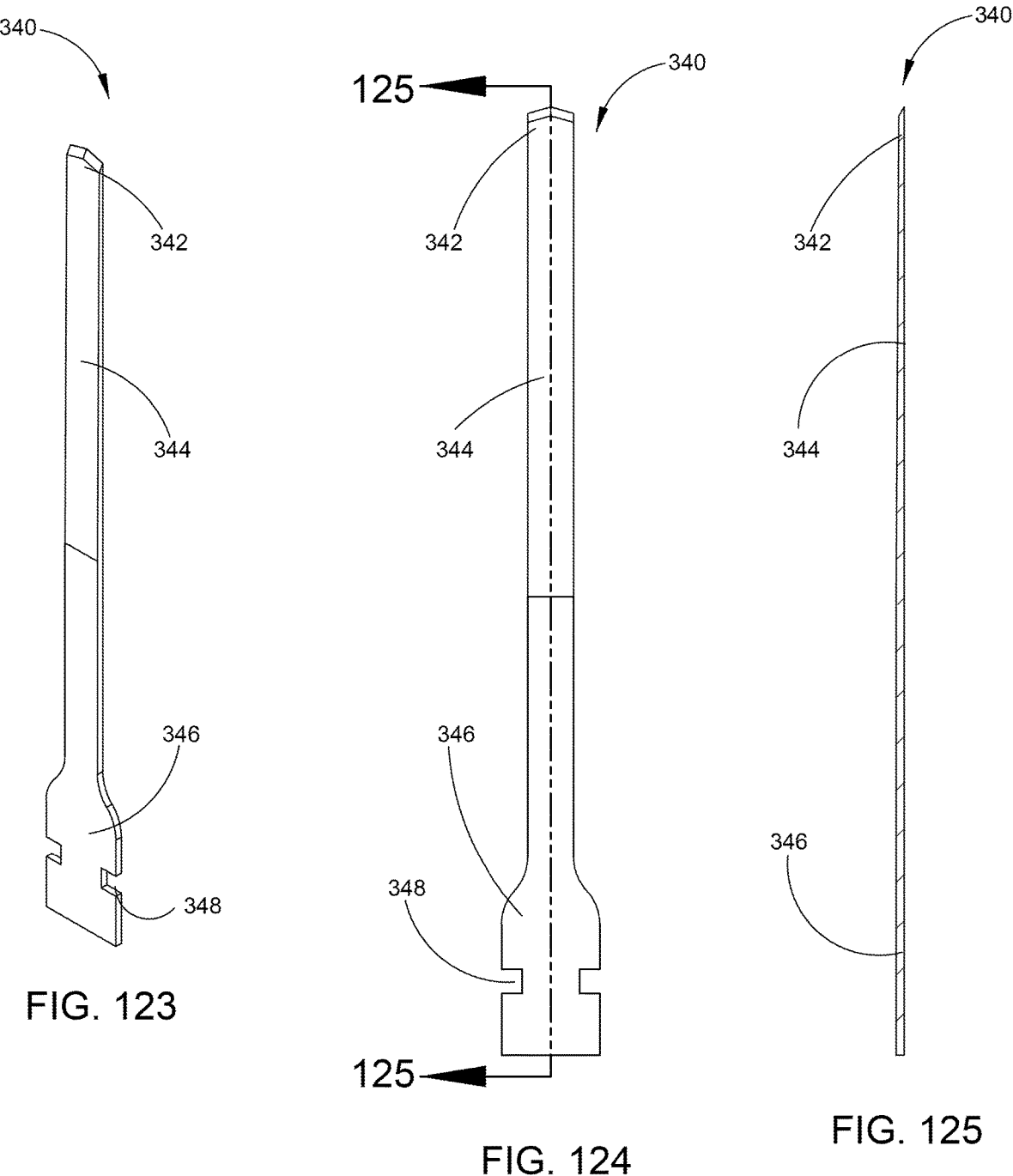

FIG. 123 depicts a top, side elevational and perspective view of a general purpose release chisel osteotome blade 340. The general purpose release chisel osteotome blade 340 is flat, semi-rigid and has the following features: a sharpened chisel shaped pointed cutting edge 342, a flat chisel blade shaft 344 and a blade insertion plate 346 having one or more blade locking slots 348 therein.

FIG. 124 depicts a front view of a general purpose release chisel osteotome blade 340, and again illustrating the location the following features: a sharpened chisel shaped pointed cutting edge 342, a flat chisel blade shaft 344 and a blade insertion plate 346 having one or more blade locking slots 348 therein.

FIG. 125 depicts a cross-sectional view of the general purpose release chisel osteotome blade 340, as shown in FIG. 124. The general purpose release chisel osteotome blade 340 includes a sharpened chisel shaped pointed cutting edge 342, a flat chisel blade shaft 344 and a blade insertion plate 346 as seen in this FIG. 125.

FIG. 126 depicts a top plan view of a general purpose release chisel osteotome blade 340 showing the sharpened chisel shaped cutting edge 342 located at the top of the general purpose release chisel osteotome blade 340.

FIG. 127 depicts a bottom view of a general purpose release chisel osteotome blade 340 showing the blade insertion plate 346 located at the bottom of the general purpose release chisel osteotome blade 340.

FIG. 128 depicts a rear view of a general purpose release chisel osteotome blade 340. The general purpose release chisel osteotome blade 340 is flat, semi-rigid and has the following features: a sharpened chisel shaped pointed cutting edge 342, a flat chisel blade shaft 344 and a blade insertion plate 346 having one or more blade locking slots 348 therein.

FIG. 129 depicts a left side elevational view of a general purpose release chisel osteotome blade 340. Here illustrating the location of a sharpened chisel shaped pointed cutting edge 342, a flat chisel blade shaft 344 and a blade insertion plate 346.

FIG. 130 depicts a front view of a general purpose release chisel osteotome blade The general purpose release chisel osteotome blade 340 is flat, semi-rigid and has the following features: a sharpened chisel shaped pointed cutting edge 342, a flat chisel blade shaft 344 and a blade insertion plate 346 having one or more blade locking slots 348 therein.

FIG. 131 depicts a right side elevational view of a general purpose release chisel osteotome blade 340. Here illustrating the location of a sharpened chisel shaped pointed cutting edge 342, a flat chisel blade shaft 344 and a blade insertion plate 346.

FIG. 132 depicts a top, side elevational and perspective view of an anterior and posterior osteotome blade 350 having a sharpened pointed cutting edge 352, a left side sharpened curved cutting edge 358, wherein said left side curvature defines a blade protrusion section 356 on the left side of the cutting blade, and a right side sharpened straight cutting edge 354. The additional features of the anterior and posterior osteotome blade 350 include a blade shaft 360, and a blade insertion plate 362 having one or more blade locking slots 364 therein.

FIG. 133 depicts a front view of an anterior and posterior osteotome blade 350 having a sharpened pointed cutting edge 352, a left side sharpened curved cutting edge 358, clearly showing said left side curvature defining a blade protrusion section 356 on the left side of the cutting blade, and a right side sharpened straight cutting edge 354, as well as the features of the anterior and posterior osteotome blade 350 include a blade shaft 360, and a blade insertion plate 362 having one or more blade locking slots 364 therein.

FIG. 134 depicts a cross-sectional view of the anterior and posterior osteotome blade 350, as shown in FIG. 133. Here the sharpened pointed cutting edge 352, the blade shaft 360 and the blade insertion plate 362 are all seen within this cross-sectional view.

FIG. 135 depicts a top plan view of an anterior and posterior osteotome blade 350 illustrating the location of the sharpened pointed cutting edge 352 and the right side sharpened straight cutting edge 354.

FIG. 136 depicts a bottom view of an anterior and posterior osteotome blade 350 illustrating the location of the blade protrusion section 356 and the blade insertion plate 362.

FIG. 137 depicts a rear view of an anterior and posterior osteotome blade 350 having a sharpened pointed cutting edge 352, left side sharpened curved cutting edge, here showing the backside of same 368, and a right side sharpened straight cutting edge, here showing the backside of same 366. The additional features of the anterior and posterior osteotome blade 350 are also seen here including a blade shaft 360, and a blade insertion plate 362 having one or more blade locking slots 364 therein.

FIG. 138 depicts a left side elevational view of an anterior and posterior osteotome blade 350 showing the sharpened pointed cutting edge 352, the left side sharpened curved cutting edge 358 and the blade insertion plate 362.

FIG. 139 depicts a front view of an anterior and posterior osteotome blade 350 having a sharpened pointed cutting edge 352, a left side curved cutting edge 358, wherein said left side curvature defines a blade protrusion section 356 on the left side of the cutting blade, and a right side straight cutting edge 354. The additional features of the anterior and posterior osteotome blade 350 include a blade shaft 360, and a blade insertion plate 362 having one or more blade locking slots 364, all seen herein.

FIG. 140 depicts a right side elevational view of an anterior and posterior osteotome blade 350 showing the sharpened pointed cutting edge 352, the right side straight cutting edge 354, the blade shaft 360 and the blade insertion plate 362.

FIG. 141 depicts a top, side elevational and perspective view of an anterior and posterior osteotome blade 370 having pointed sharpened top cutting edge 372, a right side curved cutting edge 378, wherein said right side curvature defines a blade protrusion section 376 on the right side of the cutting blade, and a left side straight cutting edge 374, which is configured as the mirror image of the blades shown in FIGS. 132-140. Additional features of the anterior and posterior osteotome blade 370 include a blade shaft 380, an blade insertion plate 382 and one or more blade locking slots 384 located within the blade insertion plate 382. In operation, the locking slots 384 are used to lock the blade into place in a osteotome blade handle assembly 220 (see above FIGS. 52-66).

FIG. 142 depicts a front view of an anterior and posterior osteotome blade 370 having pointed sharpened top cutting edge 372, a right side curved cutting edge 378, wherein said right side curvature defines a blade protrusion section 376 on the right side of the cutting blade, and a left side straight cutting edge 374, which is configured as the mirror image of the blades shown in FIGS. 132-140. Additional features of the anterior and posterior osteotome blade 370 include a blade shaft 380, a blade insertion plate 382 and one or more blade locking slots 384 located within the blade insertion plate 382.

FIG. 143 depicts a cross-sectional view of the anterior and posterior osteotome blade 370 having pointed sharpened top cutting edge 372, a right side curved cutting edge 378, as shown in FIG. 142. The cross-sectional view illustrates the pointed sharpened top cutting edge 372, the left side straight cutting edge 374, the blade shaft 380 and the blade insertion plate 382.

FIG. 144 depicts a top plan view of an anterior and posterior osteotome blade 370 showing the right side curved cutting edge 378 and the blade insertion plate 382.

FIG. 145 depicts a bottom view of an anterior and posterior osteotome blade 370 showing the blade insertion plate 382 and the blade protrusion section 376 on the right side of the cutting blade.

FIG. 146 depicts a rear view of an anterior and posterior osteotome blade 370 having a sharpened pointed cutting edge 372, right side sharpened curved cutting edge 378 (not shown here, see FIG. 142), here showing the backside of same 386, and a left side sharpened straight cutting edge 374 (not shown here, see FIG. 142), here showing the backside of same 388. The additional features of the anterior and posterior osteotome blade 370 are also seen here including a blade shaft 380, and a blade insertion plate 382 having one or more blade locking slots 384 therein.

FIG. 147 depicts a left side elevational view of an anterior and posterior osteotome blade 370 having pointed sharpened top cutting edge 372, a right side curved cutting edge 378, as shown in FIG. 142. The cross-sectional view illustrates the pointed sharpened top cutting edge 372, the left side straight cutting edge 374, the blade shaft 380 and the blade insertion plate 382.

FIG. 148 depicts a front view of an anterior and posterior osteotome blade 370 having pointed sharpened top cutting edge 372, a right side curved cutting edge 378, wherein said right side curvature defines a blade protrusion section 376 on the right side of the cutting blade, and a left side straight cutting edge 374, which is configured as the mirror image of the blades shown in FIGS. 132-140. Additional features of the anterior and posterior osteotome blade 370 include a blade shaft 380, a blade insertion plate 382 and one or more blade locking slots 384 located within the blade insertion plate 382.

FIG. 149 depicts a right side elevational view of an anterior and posterior osteotome blade 370 having pointed sharpened top cutting edge 372. Also seen in this view is a right side curved cutting edge 378 and a blade insertion plate 382.

FIG. 150 depicts a front view of an osteotome blade locking handle assembly 220 having a flexible medial calcar spoon-shaped blade 260 attached thereto, with the flexible medial calcar spoon-shaped blade 260 extending through, and being guided by the guide block assembly 20 and cutting the medial calcar from an implanted femoral stem 130. This FIG. 150 illustrates the system using like parts shown in FIGS. 1-149. Once the guide block assembly 20 is adjusted for the size and shape of the implant, using the upper guide plate 26, the lower guide plate 38 and held securely by the guide plate adjustment screw 30, the blade can be moved downwardly (see direction arrow) to cut the implant 130 from the bone (not shown). The flexible medial calcar spoon-shaped blade 260 is secured to the osteotome handle assembly 220 and flexes as it passes downward along the contour of the implant medial calcar.

FIG. 151 depicts a top, side elevational and perspective view of an osteotome blade locking handle assembly 220 having a flexible medial calcar spoon-shaped blade 260 attached thereto, with the flexible medial calcar spoon-shaped blade 260 extending through, and being guided by the guide block assembly 20 and cutting the medial calcar from an implanted femoral stem. This FIG. 150 illustrates the system using like parts shown in FIGS. 1-149. Before insertion of the blade 260, the guide block is secured to the trunnion of the implant using trunnion securing member 44 and the guide plate 38 is adjusted for the size and contour of the implant medial calcar surface. Following cutting the implant from the bone, the slide hammer assembly 200 is threaded into the guide block 20 and with upward striking motion, the implant is extracted upwardly away from the bone.

FIG. 152 depicts a rear view of an osteotome blade locking handle assembly 220 having a flexible medial calcar spoon-shaped blade 260 attached thereto, with the flexible medial calcar spoon-shaped blade 260 extending through, and being guided by the guide block assembly 20 and cutting the medial calcar from an implanted femoral stem 130. This FIG. 152 illustrates the system using like parts shown in FIGS. 1-149. The cutting edge 262 of with the flexible medial calcar spoon-shaped blade 260, secured by osteotome handle assembly 220 is guided by the adjusted guide block assembly 20 to cut along the contour of the medial calcar of the implant 130. Later, the lateral shoulder of the implant is cut away from the bone using a curved lateral shoulder release blade, see FIGS. 67 and 68. Furthermore, the anterior and posterior implant surfaces are cut from the bone using the osteotome blades described in FIGS. 132-149. The same osteotome blade locking handle assembly 220 is used in each bone cutting operation as the various osteotome blades are readily removed and replaced as required during revision surgery procedures.

FIG. 153 depicts a cross-sectional view of the osteotome blade locking handle 220 having a flexible medial calcar spoon-shaped blade attached thereto, with the flexible medial calcar spoon-shaped blade 260 extending through, and being guided by the guide block assembly 20 and cutting the medial calcar from an implanted femoral stem 130, as shown in FIG. 152. This FIG. 153 illustrates the system using like parts shown in FIGS. 1-149. In this view it is clearly evident that the guide block assembly 20 is adjusted for the size and shape of the implant, using the upper guide plate 26, the lower guide plate 38 and held securely by the guide plate adjustment screw 30. Also shown here, in FIG. 153, is the locking handle 222 and the locking lever 230 securing the blade 260 in place for moving the flexible medial calcar spoon-shaped blade 260 in the downward or upward direction (see direction arrow). The cutting edge 262 of with the flexible medial calcar spoon-shaped blade 260, secured by osteotome handle assembly 220 is guided by the adjusted guide block assembly 20 to cut along the contour of the medial calcar of the implant 130. In this case, the implant is non-collared, but it should be understood that the Joint Revision Surgery System and method described herein works equally well to extract collared implants.

FIG. 154 depicts a front view of an osteotome blade locking handle assembly 220 having a flexible medial calcar spoon-shaped blade 260 attached thereto, with the flexible medial calcar spork-shaped blade 280 extending through, and being guided by the guide block assembly 20 and cutting the medial calcar from an implanted femoral stem 130. This FIG. 154 illustrates the system using like parts shown in FIGS. 1-149. Once the guide block assembly 20 is adjusted for the size and shape of the implant, using the upper guide plate 26, the lower guide plate 38 and held securely by the guide plate adjustment screw 30, the blade can be moved downwardly (see direction arrow) to cut the implant 130 from the bone (not shown). The flexible medial calcar spork-shaped blade 280 is secured to the osteotome handle assembly 220 and flexes as it passes downward along the contour of the implant medial calcar, cutting the implant 130 away from the bone using cutting edge 282.

FIG. 155 depicts a top, side elevational and perspective view of an osteotome blade locking handle assembly 220 having a flexible medial calcar spork-shaped blade 280 attached thereto, with the flexible medial calcar spork-shaped blade 280 extending through, and being guided by the guide block assembly 20 and cutting the medial calcar from an implanted femoral stem. This FIG. 155 illustrates the system using like parts shown in FIGS. 1-149. Before insertion of the flexible medial calcar spork-shaped blade 280, the guide block is secured to the trunnion of the implant using trunnion securing member 44 and the guide plate 38 is adjusted for the size and contour of the implant medial calcar surface. Following cutting the implant from the bone, the slide hammer assembly 200 (not shown) is threaded into the guide block 20 at female threaded orifice 34, and with upward striking motion, the implant is extracted upwardly away from the bone FIG. 156 depicts a rear view of an osteotome blade locking handle assembly 220 having a flexible medial calcar spoon-shaped blade 260 attached thereto, with the flexible medial calcar spoon-shaped blade 260 extending through, and being guided by the guide block assembly 20 and cutting the medial calcar from an implanted femoral stem 130. This FIG. 156 illustrates the system using like parts shown in FIGS. 1-149. The cutting edge 262 of with the flexible medial calcar spoon-shaped blade 260, secured by osteotome handle assembly 220 is guided by the adjusted guide block assembly 20 to cut along the contour of the medial calcar of the implant 130. Later, the lateral shoulder of the implant is cut away from the bone using a curved lateral shoulder release blade, see FIGS. 67 and 68. Furthermore, the anterior and posterior implant surfaces are cut from the bone using the osteotome blades described in FIGS. 132-149. The same osteotome blade locking handle assembly 220 is used in each bone cutting operation as the various osteotome blades are readily removed and replaced as required during revision surgery procedures.

FIG. 157 depicts a cross-sectional view of the osteotome blade locking handle 220 having a flexible medial calcar spork-shaped blade 280 attached thereto, with the flexible medial calcar spoon-shaped blade 280 extending through, and being guided by the guide block assembly 20 and cutting the medial calcar from an implanted femoral stem 130, as shown in FIG. 156. This FIG. 157 illustrates the system using like parts shown in FIGS. 1-149. In this view it is clearly evident that the guide block assembly 20 is adjusted for the size and shape of the implant, using the upper guide plate 26, the lower guide plate 38 and held securely by the guide plate adjustment screw 30. Also shown here, in FIG. 153, is the locking handle 222 and the locking lever 230 securing the flexible medial calcar spoon-shaped blade 280 in place for moving the blade 260 in the downward or upward direction (see direction arrow). The cutting edge 282 of with the flexible medial calcar spoon-shaped blade 280, secured by osteotome handle assembly 220 is guided by the adjusted guide block assembly 20 to cut along the contour of the medial calcar of the implant 130. Following cutting the implant from the bone, the slide hammer assembly 200 is threaded into the guide block 20 and with upward striking motion, the implant is extracted upwardly away from the bone. In this case, the implant is non-collared, but it should be understood that the Joint Revision Surgery System and method described herein works equally well to extract collared implants. This FIG. 157 then illustrates the four primary components of the system working together to efficiently extract an implant in significantly less time, with significantly less blood loss, and therefore with significantly improved revision surgery patient outcomes.

In summary, the four primary components, namely: (1) the guide block assembly 20; (2) the osteotome blade locking handle assembly 220; (3) the slide hammer; and (4) the various flexible medial calcar osteotome blades, the lateral shoulder release blade, the anterior and posterior blades and the general purpose release chisel of the Joint Revision Surgery System and Method all work synergistically together to make extraction of an implant more efficient, less time consuming and with significantly less blood loss by the patient, all of which result in improved patient outcomes. Moreover, this system can be adjusted for any size and shape of implant to be extracted, including collared and non-collared prostheses. The guide block assembly 20 embodiment of the joint revision surgery system and method 10A wherein an assembled osteotome blade guide block 20 having an adjustable L-shaped osteotome blade guide plate 26 and 38, can be adjusted in two separate ways. First, the adjustment plate retaining screw 30 can be threaded outwardly (lifted) or threaded inwardly (lowered) to retract or extend the lower adjustment plate 38 towards or away from the stem. Second, the adjustment plate retaining screw 30 can be removed altogether and the guide plate lower section 38 shifted to a different guide slot within the plurality of guide slots 36, with that guide slot being closer or farther away from the stem to be extracted. One or both of the aforementioned guide plate adjustments can be made to successfully guide a cutting blade down to a stem of varying size, and in this way the guide block assembly 20 can accommodate varying sized stems to be removed during revision surgery. Moreover, both a collared and non-collared stem can be extracted by making the appropriate adjustments to the length and distance of the adjustable guide plate. Regarding the various osteotome blades and surgical chisels described herein, an osteotome is an orthopedic instrument that is typically used for cutting bone. A surgical chisel is used for shaping bone. Functionally, the primary difference is that a chisel has one beveled edge, while an osteotome has two beveled edges. Additionally, the flexible medial calcar osteotome blade having a spoon-shaped and spork-shaped cutting edges can be configured to be an osteotome blade having two of the sharpened cutting edges beveled or configured to be a surgical chisel wherein only one side of the sharpened cutting edge is beveled. This is also an aspect of the present invention, wherein all of the blades disclosed and described herein can be configured as either osteotome blades or surgical chisels, can be flexible or rigid, and can be curved and compound curved (curved in two planes).

In addition to the two-piece construction of the assembled surgical osteotome blade guide block 20, it is anticipated that the surgical osteotome blade guide block assembly 20 of the present invention could be manufactured and formed in one piece by being molded or computer numerical control (CNC) formed from a piece of material, including but not limited to metal, plastic, wood, ceramic and composite. Likewise, it is anticipated that the stem trunnion securing member of the present invention could be manufactured and formed in one or two pieces by being molded or computer numerical control (CNC) formed from one or two pieces of material, including but not limited to metal, plastic, wood, ceramic and composite.

In joint revision surgery, the extraction of an implanted prosthesis, like a femoral stem presents a challenging problem to the surgeon. The present invention makes the process of extraction significantly easier, quicker, more efficient and much less damaging to the patient. To summarize, the following are the 12 steps of the surgical procedure utilizing the Joint Revision Surgery Apparatus 10A to extract a femoral stem, according to the present invention:

Steps of the Femoral Stem Extraction Procedure Utilizing Guide Block Assembly 20 of Embodiment 10A (Adjustable Guide Plate Method).

1. Approach the hip in the surgeons preference, i.e. anterior, posterior, or lateral.

2. Release the soft tissue and dislocate the hip. Remove the femoral head. Remove soft tissue as needed to expose the bone implant interface. Use a Lambotte osteotome to define the bone implant interface. If a collared stem is found remove a small portion of bone below the collar to allow the flexible osteotome access to the stem below the collar.

3. Next using the anterior and posterior side specific osteotomes advance the anterior and posterior osteotome blades down the anterior and posterior surfaces of the implant to release the anterior and posterior surfaces of the implant from the bone.

4. After the anterior and posterior surfaces are released then choose the appropriate trunnion securing member adaptor.

5. Tighten the guide block trunnion securing member to the stem trunnion and secure the trunnion securing member to the guide block using the securing nut.

6. Next choose the appropriate slot to place the adjustable guide plate into. After the correct slot has been chosen then thread the screw into the block and adjust the guide plate to the appropriate depth.

7. Next advance the flexible medial calcar osteotome blade down the calcar. Adjust the guide plate as needed as the blade is advanced to cut the medial calcar implant surface away from the bone.

8. Remove the flexible medial calcar osteotome blade.

9. Next choose the correct slot laterally and advance the curved lateral shoulder release osteotome blade until the lateral shoulder is released from the bone.

10. Thread the slide hammer into the threaded orifice on the upper surface of the guide block assembly.

11. Move the slide hammer handle upwardly slapping it against the upper impact cap until the implant is fully released.

12. Extract the implant by upward movement of the slide hammer.

The Joint Revision Surgery Osteotome Blades and Surgical Chisel Blades components 10A, 20, 100, 140, 200, 220, 260, 270, 280, 290, 300, 320, 340, 350 and 370 shown in the drawings and described in detail herein disclose arrangements of elements of particular construction and configuration for illustrating preferred embodiments of structure and method of operation of the present design. It is to be understood, however, that elements of different construction and configuration and other arrangements thereof, other than those illustrated and described may be employed for providing Joint Revision Surgery Osteotome Blades and Surgical Chisel Blades components 10A, 20, 100, 140, 200, 220, 260, 270, 280, 290, 300, 320, 340, 350 and 370 in accordance with the spirit of this application, and such changes, alternations and modifications as would occur to those skilled in the art are considered to be within the scope of this application as broadly defined in the appended claims.

While certain embodiments of the inventions have been described, these embodiments have been presented by way of example only, and are not intended to limit the scope of the disclosure. Indeed, the novel methods and systems described herein may be embodied in a variety of other forms. Furthermore, various omissions, substitutions and changes in the systems and methods described herein may be made without departing from the spirit of the disclosure. For example, one portion of one of the embodiments described herein can be substituted for another portion in another embodiment described herein. The accompanying claims and their equivalents are intended to cover such forms or modifications as would fall within the scope and spirit of the disclosure. Accordingly, the scope of the present inventions is defined only by reference to the appended claims.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can." "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

Further, the purpose of the foregoing abstract is to enable the U.S. Patent and Trademark Office, foreign patent offices worldwide and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

I claim:

1. A joint revision surgery medial calcar osteotome blade comprising:
   (a) a cutting edge the blade having a longitudinal axis and a curvature about the longitudinal axis, such that the cutting edge is disposed symmetrically about the longitudinal axis, and further wherein said cutting edge is beveled on both sides;
   (b) a flexible blade shaft; and
   (c) a blade insertion plate including two blade locking slots.

2. The joint revision surgery medial calcar osteotome blade according to claim 1, wherein said blade terminates in a pointed tip that lies on the longitudinal axis.

3. The joint revision surgery medial calcar osteotome blade according to claim 2, wherein said flexible blade shaft is straight.

4. The joint revision surgery medial calcar osteotome blade according to claim 2, wherein said flexible blade shaft is elongated along a longitudinal axis of the blade.

5. The joint revision surgery medial calcar osteotome blade according to claim 1, wherein said cutting edge comprises a first cutting edge portion and a second cutting edge portion disposed symmetrically about the longitudinal axis of the blade wherein a point on the first cutting edge portion and a point on the second cutting edge portion are symmetrically located about the longitudinal axis and are located distal to the pointed tip of the blade centrally located on the longitudinal axis of the blade.

6. The joint revision surgery medial calcar osteotome blade according to claim 5, wherein said flexible blade shaft is elongated along a longitudinal axis of the blade.

\* \* \* \* \*